(12) United States Patent
Hendsbee et al.

(10) Patent No.: US 9,865,819 B2
(45) Date of Patent: Jan. 9, 2018

(54) NITROGEN ANNULATED PERYLENE DIIMIDES FOR USE AS ELECTRON TRANSPORT MATERIALS IN ORGANIC ELECTRONIC DEVICES

(71) Applicant: UTI Limited Partnership, Calgary (CA)

(72) Inventors: Arthur D. Hendsbee, Calgary (CA); Jon-Paul Sun, Halifax (CA); Gregory C. Welch, Calgary (CA); Ian G. Hill, Halifax (CA); Seth McAfee, Calgary (CA); Jonathan Cann, Calgary (CA)

(73) Assignee: UTI Limited Partnership, Calgary, Alberta (CA)

( * ) Notice: Subject to any disclaimer, the term of this patent is extended or adjusted under 35 U.S.C. 154(b) by 0 days.

(21) Appl. No.: 15/615,212

(22) Filed: Jun. 6, 2017

(65) Prior Publication Data
US 2017/0352812 A1    Dec. 7, 2017

Related U.S. Application Data

(60) Provisional application No. 62/346,460, filed on Jun. 6, 2016, provisional application No. 62/346,504, filed on Jun. 6, 2016.

(51) Int. Cl.
| | |
|---|---|
| *C07D 471/18* | (2006.01) |
| *H01L 31/00* | (2006.01) |
| *H01L 51/00* | (2006.01) |
| *C07D 471/16* | (2006.01) |
| *C07D 519/00* | (2006.01) |
| *H01L 51/42* | (2006.01) |
| *H01L 51/05* | (2006.01) |

(52) U.S. Cl.
CPC ........ *H01L 51/0053* (2013.01); *C07D 471/16* (2013.01); *C07D 519/00* (2013.01); *H01L 51/0068* (2013.01); *H01L 51/0071* (2013.01); *H01L 51/0072* (2013.01); *H01L 51/0558* (2013.01); *H01L 51/4253* (2013.01)

(58) Field of Classification Search
CPC .............................. C07D 471/18; H01L 31/00
USPC .................................... 546/31; 136/263, 252
See application file for complete search history.

(56) References Cited

FOREIGN PATENT DOCUMENTS

| | | |
|---|---|---|
| CN | 104892629 | 9/2015 |
| WO | 2016/016498 | 2/2016 |

OTHER PUBLICATIONS

Acikbas, Y. et al.(Feb. 2016) "Optical Characterization of an N, N'-Dicyclohexyl-3, 4:9, 10-Perylene bis(Dicarboximide) Langmuir-Blodgett Film for the Determination of Volatile Organic Compounds," Anal. Lett., 46(16):2573-2586, DOI: 10.1080/00032719.2015.1122028

Cann, J. et al. (Feb. 2017) "N-Annulated perylene diimide dimers: acetylene linkers as a strategy for controlling structural conformation and the impact on physical, electronic, optical and photovoltaic properties," J. Materials Chem. C, 5, 2017-2083.

Centore, R. et al. (2012) "Perylene Diimides Functionalized with N-Thiadiazole Substituents: Synthesis and Electronic Properties in OFET Devices," Org. Electron., 13, 2083-2093.

Chen, W. et al. (Apr. 2015)"A Perylene Diimide (PDI)-Based Small Molecule with Tetrahedral Configuration as a Non-Fullerene Acceptor for Organic Solar Cells," J. Mater. Chem. C, 3, 4698-4705.

Chen, Z. et al. (2007) "Photoluminescence and Conductivity of Self-Assembled π-π Stacks of Perylene Bisimide Dyes," Chem. Eur. J., 13, 436-449.

Dayneko et al. (2017, published Dec. 2016) "Fullerene-free polymer solar cells processed from non-halogenated solvents in air with PCE of 4.8%," Chem Comm, 53, 1164-1167.

Demmig, S. et al. (1988) "Leichtlösliche, Lichtechte Perylen-Fluoreszenzfarbstoffe," Chem. Ber.,121, 225-230; Eng. Title: "Very Soluble and Photostable Perylene Fluorescent Dyes." In German with English Abstract.

Doval, D. A. et al. (2012) "Amphiphilic Dynamic NDI and PDI Probes: Imaging Microdomains in Giant Unilamellar Vesicles," Org. Biomol. Chem.,10, 6087-6093.

Dwivedi, A. K. et al. (Nov. 2014) "Assembly Modulation of PDI Derivative as a Supramolecular Fluorescence Switching Probe for Detection of Cationic Surfactant and Metal Ions in Aqueous Media," ACS Appl. Mater. Interfaces, 6, 21369-21379.

Feng, X. et al. (2012) "A Turn-on Fluorescent Sensor for Pyrophosphate Based on the Disassembly of Cu2+-Mediated Perylene Diimide Aggregates," ACS Appl. Mater. Interfaces, 4, 614-618.

Fernandez-Lazaro, F. et al. (May 2016) "Perylenediimides as Non-Fullerene Acceptors in Bulk-Heterojunction Solar Cells (BHJSCs)," J. Mater. Chem. A, 4, 9336-9346.

Freeman, A. W. et al. (2005) "Triphenylphosphine-Mediated Reductive Cyclization of 2-Nitrobiphenyls: A Practical and Convenient Synthesis of Carbazoles," J. Org. Chem, 70, 5014-5019.

Hariharan, P. S. et al. (2016, published Nov. 2015) "Perylene Diimide Based Fluorescent Dyes for Selective Sensing of Nitroaromatic Compounds: Selective Sensing in Aqueous Medium Across Wide pH Range," J. Fluoresc. 2016, 26, 395-401.

Hartnett, P. E. et al. (Oct. 2014) "Slip-Stacked Perylenediimides as an Alternative Strategy for High Efficiency Nonfullerene Acceptors in Organic Photovoltaics," J. Am. Chem. Soc.,136, 16345-16356.

Hendsbee, A.D. et al. (Mar. 2017) "N-annulated perylene diimide dimers: the effect of thiophene bridges on physical, electronic, optical, and photovoltaic properties," Sustainable Energy & Fuels, 1, 1137-1147.

Hendsbee, A.D. et al. (Sep. 2016) "Synthesis, Self-Assembly, and Solar Cell Performance of N-Annulated Perylene Diimide Non-Fullerene Acceptors," Chem. Mater, 28, 7098-7109.

(Continued)

*Primary Examiner* — Charanjit Aulakh
(74) *Attorney, Agent, or Firm* — Lathrop Gage LLP

(57) ABSTRACT

PDI derivatives useful as opto-electronically active materials or for the synthesis of such materials. Certain compounds herein function as efficient electron acceptors and are useful as electron active components of electronic devices.

20 Claims, 21 Drawing Sheets

(56) References Cited

OTHER PUBLICATIONS

Hendsbee, A. D. et al. (Jul. 2105) "Phthalimide-Based [Small Pi]-Conjugated Small Molecules with Tailored Electronic Energy Levels for Use as Acceptors in Organic Solar Cells," J. Mater. Chem. C, 3, 8904-8915.

Hendsbee, A. D. et al. (Jan. 2014) "Electron Deficient Diketopyrrolopyrrole Dyes for Organic Electronics: Synthesis by Direct Arylation, Optoelectronic Characterization, and Charge Carrier Mobility," J. Mater. Chem. A, 2 (12), 4198-4207.

Huang, Y. et al. (Jun. 2014) "Probing the Sensory Property of Perylenediimide Derivatives in Hydrazine Gas: Core-Substituted Aromatic Group Effect," ACS Appl. Mater. Interfaces, 6, 9307-9313.

Hüttner, S. et al. (2008) "N-Type Organic Field Effect Transistors from Perylene Bisimide Block Copolymers and Homopolymers," Appl. Phys. Lett., 92, 093302.

Jiang, W. et al., (2014, published on line Oct. 2013) "Bay-Linked Perylene Bisimides as Promising Non-Fullerene Acceptors for Organic Solar Cells," Chem. Commun., 50, 1024-1026.

Kozma, E. et al. (2013) "Perylene Diimides Based Materials for Organic Solar Cells," Dyes Pigm. 2013, 98, 160-179.

Langhals, H. et al. (2000) "Novel Fluorescent Dyes by the Extension of the Core of Perylenetetracarboxylic Bisimides," Eur. J. Org. Chem., 365-380.

Li, M. et al., (Oct. 2014) "Achieving Balanced Intermixed and Pure Crystalline Phases in PDI-Based Non-Fullerene Organic Solar Cells via Selective Solvent Additives," Phys. Chem. Chem. Phys., 16, 26917-26928.

Li, J. et al. (2006) "Poly(2,7-Carbazole) and Perylene Tetracarboxydiimide: A Promising Donor/acceptor Pair for Polymer Solar Cells," J. Mater. Chem., 16, 96-100.

Lin, Y. et al. (May 2014) "A Twisted Dimeric Perylene Diimide Electron Acceptor for Efficient Organic Solar Cells," Adv. Energy Mater. 2014, 4, 1400420 (Lin__2014a).

Lin, Y. et al. (Mar. 2014) "A Star-Shaped Perylene Diimide Electron Acceptor for High-Performance Organic Solar Cells," Adv. Mater. 2014, 26, 5137-5142 (Lin__2014b).

Liu, X. et al. (Sep. 2015) "Pyrene Terminal Functionalized Perylene Diimide as Non-Fullerene Acceptors for Bulk Heterojunction Solar Cells," RSC Adv., 5, 83155-83163.

Liu, K. et al. (Feb. 2014) "A Multifunctional Perylenediimide Derivative (DTPDI) Can Be Used as a Recyclable Specific $Hg^{2+}$ Ion Sensor and an Efficient DNA Delivery Carrier," J. Mater. Chem. B, 2, 2093-2096.

Lüttich, F. et al. (2012) "Interface Properties of OFETs Based on an Air-Stable N-Channel Perylene Tetracarboxylic Diimide Semiconductor," Phys. Status Solidi A, 209, 585-593.

McAfee, S.M. et al. (Jan. 2017) "Simply Complex: The Efficient Synthesis of an Intricate Molecular Acceptor for High-Performance Air-Processed and Air-Tested Fullerene-Free Organic Solar Cells," Chem. Mater., 29, 1309-1314.

McAfee, S. M. et al. (Apr. 2016)"The Optimization of Direct Heteroarylation and Sonogashira Cross-Coupling Reactions as Efficient and Sustainable Synthetic Methods to Access π-Conjugated Materials with Near-Infrared Absorption," ACS Sustainable Chem. Eng., 4, 3504-3517.

McAfee, S. M. et al. (Feb. 2015) "Utility of a Heterogeneous Palladium Catalyst for theSynthesis of a Molecular Semiconductor via Stille, Suzuki, and Direct Heteroarylation Cross-Coupling Reactions," RSC Adv., 5, 26097-26106.

Mei, J. et al. (Aug. 2015) "Side Chain Engineering in Solution-Processable Conjugated Polymers," Chem. Mater. 2014, 26, 604-615.

Meng, D. et al. (2016, published Dec. 2015)"High-Performance Solution-Processed Non-Fullerene Organic Solar Cells Based on Selenophene-Containing Perylene Bisimide Acceptor," J. Am. Chem. Soc., 138, 375-380.

Qian, H. et al. (2009) "Heterocyclic Annelated Di(perylene Bisimide): Constructing Bowl-Shaped Perylene Bisimides by the Combination of Steric Congestion and Ring Strain," J. Org. Chem., 74, 6275-6282.

Qiu, S. et al. (2005) "Facile Synthesis of Carbazole-Containing Semiladder Polyphenylenes for Pure-Blue Electroluminescence," Macromolecules, 38 (16), 67.

Rajasingh, P. et al. (2007) "Selective Bromination of Perylene Diimides under Mild Conditions," J. Org. Chem., 72, 5973-5979.

Sun, D. et al. (Aug. 2015) "Non-Fullerene Acceptor-Based Bulk Heterojunction Organic Solar Cells with Efficiency over 7%," J. Am. Chem. Soc., 137, 11156-11162.

Sun, J.-P. et al. (May 2016) "Perylene Diimide Based All Small-Molecule Organic Solar Cells: Impact of Branched-Alkyl Side Chains on Solubility, Photophysics, Self-Assembly, and Photovoltaic Parameters," Org. Electron., 35, 151-157.

Tilley, A. J. et al. (Apr. 2015) "Thionation Enhances the Electron Mobility of Perylene Diimide for High Performance N-Channel Organic Field Effect Transistors," Adv. Funct. Mater., 25, 3321-3329.

Yan, Q. et al. (Aug. 2013) "Towards Rational Design of Organic Electron Acceptors for Photovoltaics: A Study Based on Perylenediimide Derivatives," Chem. Sci., 4, 4389-4394.

Zang, Y. et al. (Jun. 2014) "Integrated Molecular, Interfacial, and Device Engineering towards High-Performance Non-Fullerene Based Organic Solar Cells," Adv. Mater. 2014, 26, 5708-5714.

Zhan, X. et al. (2011) "Rylene and Related Diimides for Organic Electronics," Adv. Mater., 23, 268-284.

Zhan, X. et al. (2007) "A High-Mobility Electron-Transport Polymer with Broad Absorption and Its Use in Field-Effect Transistors and All-Polymer Solar Cells," J. Am. Chem. Soc., 129, 7246-7247.

Zhang, X. et al. (Nov. 2015) "A Selenophenyl Bridged Perylene Diimide Dimer as an Efficient Solution-Processable Small Molecule Acceptor," Chem. Commun. 2015, 51, 1058-1061.

Zhong, Y. et al. (Oct. 2014) "Efficient Organic Solar Cells with Helical Perylene Diimide Electron Acceptors," J. Am.Chem. Soc., 136, 15215-15221.

Het11    Ar12    Het12

D1    D2    D3

D4    D5 wherein each $R_1$, and each $R_3$ is independently selected from alkyl groups having 1-30 carbon atoms, 1-20 carbon atoms, 1-12 carbon atoms, 1-6 carbon atoms, 1-3 carbon atoms, 1-9 carbon atoms, 3 to 6 carbon atoms.

where each $R_3$ is independently selected from alkyl groups having 1-30 carbon atoms, . 1-20 carbon atoms, 1-12 carbon atoms, 1-6 carbon atoms, 1-3 carbon atoms, 1-9 carbon atoms, 3 to 6 carbon atoms.

where each $R_3$ is independently selected from alkyl groups having 1-30 carbon atoms, . 1-20 carbon atoms, 1-12 carbon atoms, 1-6 carbon atoms, 1-3 carbon atoms, 1-9 carbon atoms, 3 to 6 carbon atoms.

PDI$_2$ 7
LUMO: -3.8
HOMO: -6.0

PDI$_2$AC 15
LUMO: -3.7
HOMO: -5.8

NITROGEN ANNULATED PERYLENE DIIMIDES FOR USE AS ELECTRON TRANSPORT MATERIALS IN ORGANIC ELECTRONIC DEVICES

CROSS-REFERENCE TO RELATED APPLICATIONS

This application claims the benefit of U.S. provisional applications 62/346,460 and 62/346,504, both filed Jun. 6, 2016, each of which applications are incorporated by reference herein in its entirety.

BACKGROUND

Perylene diimide (PDI) based compounds represent an important class of opto-electronically active materials that have found utility in a wide variety of applications. [1] Such applications include active components in organic solar cells (OSC) [2-4], fluorescent probes used in imaging studies [5-7] chemical sensors [8-11] and semiconducting material in organic field effect transistors (OFETs) [12-14]. PDI based materials can be synthesized from relatively inexpensive starting materials, and have appreciable and tunable visible light absorption, strong self-assembly characteristics, and low-lying frontier molecular orbitals, that make them useful as electron transport materials in optoelectronic devices [3,15-19]

OSC's have the potential to provide low-cost, clean energy with minimal environmental impact. [20-22] Reliance on fullerenes as the electron transport material within the active layer of the highest performing devices. [23-27] Soluble POI based materials are being considered as attractive alternatives to fullerenes [17, 28-33]. Functionalized PDI materials exhibit a low lying lowest unoccupied molecular orbital (LUMO) which facilities electron transfer reactions, making them good electron acceptors. Importantly, functionalized PDI derivatives offer several advantages over fullerenes, including: low cost, synthetic modularity and increased light absorption in the visible region.

PDI molecules have been functionalized at the imide position with alkyl groups and at the bay position with aromatic units or certain heteroatoms to improve solubility and tailor self-assembly (Formula A) [3,19,34-37]:

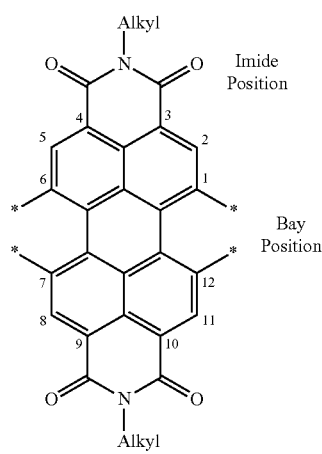

For example, dimerization of the PDI chromophore and incorporation of the heteroatoms S or Se in the bay positions of the PDI framework. [3,36,37] provided a material having a remarkable effect on both its inter- and intramolecular properties, allowing the fabrication of OSCs with PCEs up to 7.1% and 8.4% for the S and Se annulated derivatives, respectively, when paired with tailor-made donor-acceptor type π-conjugated polymers [3,31,32]

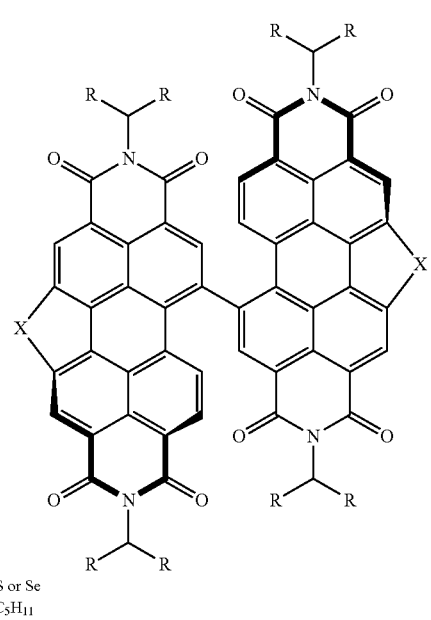

X = S or Se
R = $C_5H_{11}$

Further derivatization of the dimers of Formula B is limited and large branched alkyl chains are required to ensure adequate organic solvent solubility.

A preferred PDI material to be used as an electron acceptor in OSCs will exhibit high solubility in organic solvents to allow for a diverse array of solution processing protocols to be employed, can be prepared by high yielding and scalable synthetic methods using atom-economical and sustainable chemistry practice, employ modular synthesis allowing for preparation of a library of diverse functionalized materials and maintain the key optical and electronic properties of related PDIs, including strong visible light absorption and deep LUMO energy levels. The present disclosure is directed to functionalized PDI materials useful, for example, as electronic acceptors in OSC's, to methods of making such materials as well as to devices made from such materials. More specifically the disclosure relates to nitrogen annulated PDI derivatives, methods of making them and to devices made from such materials.

A popular strategy for modification of the perylene chromophore is to install bromine atoms at the bay positions which can then be used as directing groups in a variety of carbon-carbon bond forming reactions to form 7-extended chromophores. PDI based materials derived from the bromination of the PDI chromophore are promising candidates for the replacement of fullerenes within a bulk heterojunction (BHJ) organic solar cell. A disadvantage of such materials is that they are made using an early bromination step that requires reaction over several days in dichloromethane with elemental bromine. This bromination produces isomeric forms of PDI and is therefore low yielding by nature. In addition, isolation of desired products in the presence of dibrominated isomers requires the use of column chromatography followed by several recrystallizations. The disclosure provides improved methods for the preparation of nitrogen annulated PDI materials.

Langhalls et al. [39] reported the synthesis of certain PDI materials having a heterocyclic pyrrolic unit installed at the bay position of the chromophore. While these materials were synthesized in good yields, they were not explored as electronically active materials to be self-assembled into superstructures useful for charge transport.

SUMMARY

The disclosure relates to certain PDI derivatives useful as opto-electronically active materials or for the synthesis of such materials. Certain compounds herein function as efficient electron acceptors and are useful as electron active components of electronic devices.

In one aspect the disclosure relates to compounds of formula I:

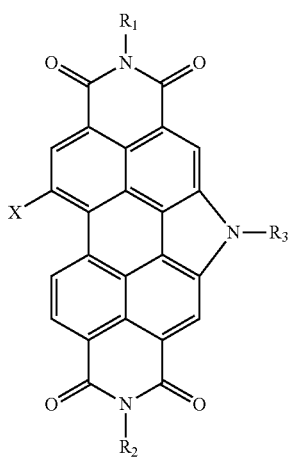

I where:
X is a halogen (F, Cl, Br or I), triflyl ($CF_3$—$SO_2$—O—), tosyl (p-Me-$C_6H_5$—$SO_2$—), mesyl ($CH_3$—$SO_2$—) and more specifically is Br;
$R_1$ and $R_2$ are independently selected from a straight-chain or branched alkyl having 1-30 carbon atoms; and
$R_3$ is selected from a straight-chain or branched alkyl group having 3-30 carbon atoms.

In specific embodiments, $R_1$ and $R_2$ are independently selected from a straight-chain alkyl having 10 or more carbon atoms or a branched chain alkyl having 3 to 20 carbon atoms.

In specific embodiments, $R_1$ and $R_2$ are independently selected from a straight-chain alky having 3 to 9 carbon atoms. In specific embodiments, $R_1$ and $R_2$ are independently selected from a branched-chain alky having 3 to 10 carbon atoms. In specific embodiments, $R_1$ and $R_2$ are the same group. In specific embodiments, $R_1$ and $R_2$ are selected from branched alkyl groups of formula —C(Ra)(Rb), where Ra and Rb are, independently, alkyl groups having 2-10 carbon atoms. In specific embodiments, Ra and Rb are the same alkyl group. In specific embodiments, Ra and Rb are different alkyl groups. In specific embodiments, Ra and Rb are straight-chain alkyl groups.

In specific embodiments, $R_1$ and $R_2$ are independently a 1-ethylpropyl, 1-propylbutyl, 1-butylpentyl, 1-pentylhexyl, 1-hexylheptyl, 1-heptyloctyl, 1-octylnonyl, 1-nonyldecyl, or 2-ethylhexyl.

In specific embodiments, $R_1$ and $R_2$ are the same alkyl group. In specific embodiments, $R_1$ and $R_2$ are different alkyl groups. In specific embodiments, $R_1$ and $R_2$ are both 1-ethylproypl groups.

In specific embodiments, $R_1$ and $R_2$ are independently selected from branched alkyl groups having 3-8 carbon atoms. In specific embodiments, $R_1$ and $R_2$ are the same branched alkyl groups.

In specific embodiments, $R_3$ is independently selected from a straight chain alkyl having 1 to 12, or 1-10 or 4 to 12 or 4 to 10 or 4 to 6 carbon atoms or a branched chain alkyl having 3-12 or 3-10 carbon atoms.

In specific embodiments, $R_3$ is independently a straight-chain alkyl group selected from a methyl, ethyl, propyl, butyl, pentyl, hexyl, heptyl, octyl, nonyl, and decyl group.

In specific embodiments, $R_3$ is independently a branched alkyl group having 3-12 carbon atoms.

In specific embodiments, $R_3$ is independently a branched alkyl group having 6-12 carbon atoms.

In specific embodiments, $R_3$ is independently a branched alkyl group having 3-6 carbon atoms.

In specific embodiments, $R_3$ is independently selected from 1-ethylpropyl, 1-propyl butyl, or 2-ethylhexyl.

The disclosure also relates to compounds of formula II:

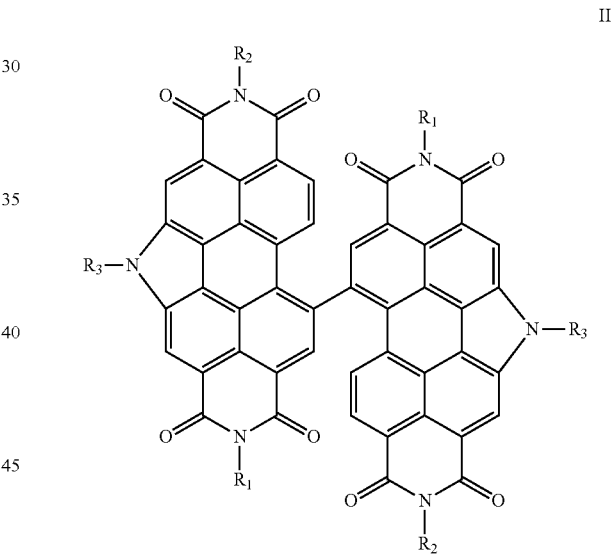

II where $R_1$-$R_3$ are as defined in the compound of formula I, including the various embodiments listed above, and noting that each $R_1$, each $R_2$ and each $R_3$ in the compound may be the same or a different alkyl group.

In specific embodiments, each $R_1$ is the same alkyl group.
In specific embodiments, each $R_2$ is the same alkyl group.
In specific embodiments, each $R_3$ is the same alkyl group.
In specific embodiments, each $R_1$ and each $R_2$ are independently selected from a straight-chain alkyl having 10 or more carbon atoms or a branched chain alkyl having 3 to 20 carbon atoms.

In specific embodiments, each $R_1$ and each $R_2$ are independently a 1-ethylpropyl, 1-propylbutyl, 1-butylpentyl, 1-pentylhexyl, 1-hexylheptyl, 1-heptyloctyl, 1-octylnonyl, 1-nonyldecyl, or 2-ethylhexyl.

In specific embodiments, each $R_1$ and each $R_2$ are the same alkyl group. In specific embodiments, each $R_1$ and each $R_2$ are different alkyl groups. In specific embodiments, each $R_1$ and each $R_2$ are both 1-ethylproypl groups.

In specific embodiments, each $R_1$ and each $R_2$ are independently selected from branched alkyl groups having 3-8 carbon atoms. In specific embodiments, each $R_1$ and each $R_2$ are the same branched alkyl groups.

In specific embodiments, each $R_3$ is independently selected from a straight chain alkyl having 1 to 12, 1-10 or 4 to 12 or 4 to 10 or 4 to 6 carbon atoms or a branched chain alkyl having 3-12 or 3-10 carbon atoms.

In specific embodiments, each $R_3$ is independently a straight-chain alkyl group selected from a methyl, ethyl, propyl, butyl, pentyl, hexyl, heptyl, octyl, nonyl, and decyl group.

In specific embodiments, each $R_3$ is independently a branched alkyl group having 3-12 carbon atoms.

In specific embodiments, each $R_3$ is independently selected from 1-ethylpropyl, 1-propyl butyl, or 2-ethylhexyl.

The disclosure also relates to compounds of formula III:

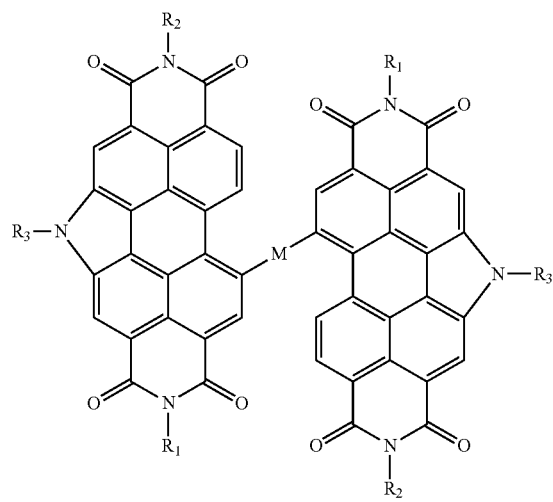

III where $R_1$-$R_3$ are as defined in formula II, and

M is a divalent linking moiety selected from:

an arylene (—Ar—), a heteroarylene (—HAr—), an alkynylene (-≡-), a dialkynylene (-≡-≡-), an organic dye moiety or M is:

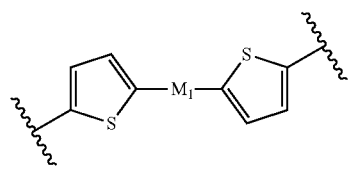

where $M_1$ is an arylene, a heteroarylene, or an organic dye molecule.

The disclosure further relates to compounds of formula IV:

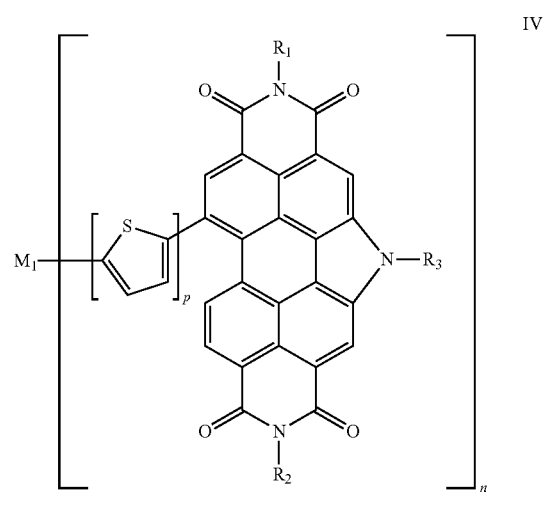

IV where p is 0 or 1 to show the presence or absence of the thiophene, n is 2, 3 or 4 indicating that the $M_1$ group is divalent, trivalent or tetravalent.

Note that M groups differ from $M_1$ groups in that $M_1$ groups do not themselves have thiophene groups.

In specific embodiments of formula IV, p is 0 and n is 2, 3 or 4.

In specific embodiments of formula IV, p is 1 and n is 2, 3 or 4.

In specific embodiments of formula IV, p is 0 and n is 2.

In specific embodiments of formula IV, p is 0 and n is 3.

In specific embodiments of IV, p is 0 and n is 4.

In specific embodiments of formula IV, p is 1 and n is 2.

In specific embodiments of formula IV, p is 1 and n is 3.

In specific embodiments of formula IV, p is 1 and n is 4.

The disclosure additionally provides an electronic device employing an electron acceptor wherein the electron acceptor is one or more compounds of formulas III and IV herein.

The disclosure provides an organic solar cell employing an electron acceptor wherein the electron acceptor is one or more compounds of formulas III and IV herein.

The disclosure provides an organic thin film transistor employing an electron acceptor wherein the electron acceptor is one or more compounds of formulas III and IV herein.

The disclosure provides a redox flow battery which comprises one or more compounds of formulas III or IV herein.

In another aspect, the disclosure relates to a method for preparation of a compound of formula I, where X is bromine (Formula VI), which involves preparation of a compound of formula V and bromination of that compound of formula V:

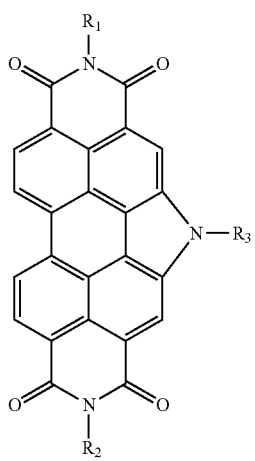

V

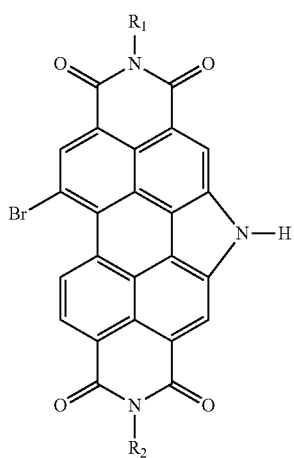

VI

Bromination is carried out in an organic solvent, in which the compound of formula V is at least partially soluble, at room temperature with at least one molar equivalent of Br$_2$ with respect to the compound of formula V. Preferably an excess of bromine is used in the bromination. The amount of bromine used can range from 2 to 150 molar equivalents and more specifically ranges from 25 to 100 molar equivalents with respect to the compound of formula V. Yet more preferably the amount of bromine used ranges from 50 to 100 molar equivalents. The reaction components are mixed until the starting compound of formula V is consumed (about 2 hours). Solvent (e.g., dichloromethane) is removed and the brominated compound is isolated and purified. This method allows for bromination at a later stage in the synthesis compared to previous methods and results in a significant improvement in yield and a reduction in the complexity of purification.

In general any organic solvent in which the reaction components are soluble can be employed. A non-polar or a moderately polar aprotic solvent with dielectric constant of 10 or less can be employed. Crude product can be purified by any silica gel column chromatography employing a hexane to dichloromethane gradient, where compound 6 elutes at about 80% dichloromethane. It will be appreciated that purification steps, such as elution time, can vary dependent upon the substituents on the starting material.

BRIEF DESCRIPTION OF THE DRAWINGS

(FIG. 6A) shows current density-voltage curves, (FIG. 6B) shows external quantum efficiency, (FIG. 6C) shows the normalized absorbance of the best performing blends of compounds (5), (7), and (7b). (FIG. 6D) shows 520-670 nm PL spectra of neat films of the PDI acceptors, as well as blend films with PTB7 under 500 nm excitation. 670-900 nm: PL spectra of neat PTB7 as well as blend films with PDI acceptors under 650 nm excitation.

FIGS. 8A and 8B are absorption spectra in solution and as-cast, respectively, of compound 10-12. FIG. 8C shows cyclic voltammograms for compounds 10-12. FIG. 8D shows the HOMO LUMO energy differences for compounds 10-12.

FIG. 9A shows device architecture and active layer electron affinities and ionization potentials. FIG. 9B Current-voltage curves for as-cast (1) and CHCl₃ SVA, 2-5 min (2) and 10 min (3). FIG. 9C Active layer blend UV-vis profiles: as-cast (1) and 2-5 min (2) and 10 min (3) CHCl₃ SVA. (d) External quantum efficiency profiles for as-cast (1) and 2-5 min (2) and 10 min (3) CHCl₃ SVA.

DETAILED DESCRIPTION

Figure 1A:
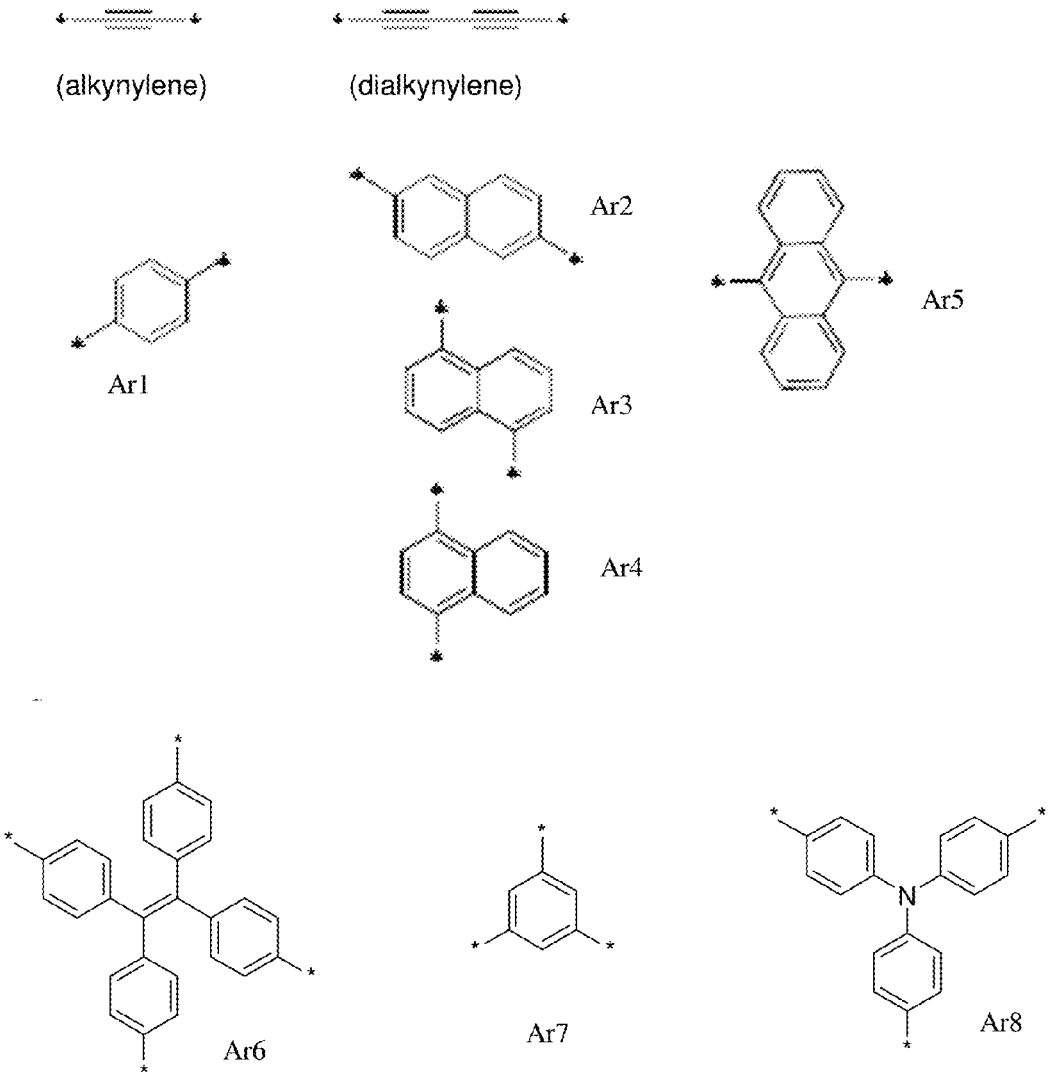
FIGS. 1A-1D illustrate exemplary M and M1 groups for compounds of Formula IV. M and M1 groups in these figures can be unsubstituted, substituted as indicated or substituted with one or more halogen, nitro group or cyano group. For groups AR1-AR8 the group is optionally substituted with one or more halogen, nitro group or cyano group. For groups Ar9-Ar12 the group is optionally substituted with one or more halogen, nitro group or cyano group and more specifically with 1, 2, 4, 6, 8, 10 or 12 such groups as appropriate for a given structure. For groups Het3-Het 12 the group is optionally substituted with one or more halogen, nitro group or cyano group. Groups PDI1 and NDI1 the groups may be unsubstituted or substituted with one or more cyano or nitro group.
Figure 1B:
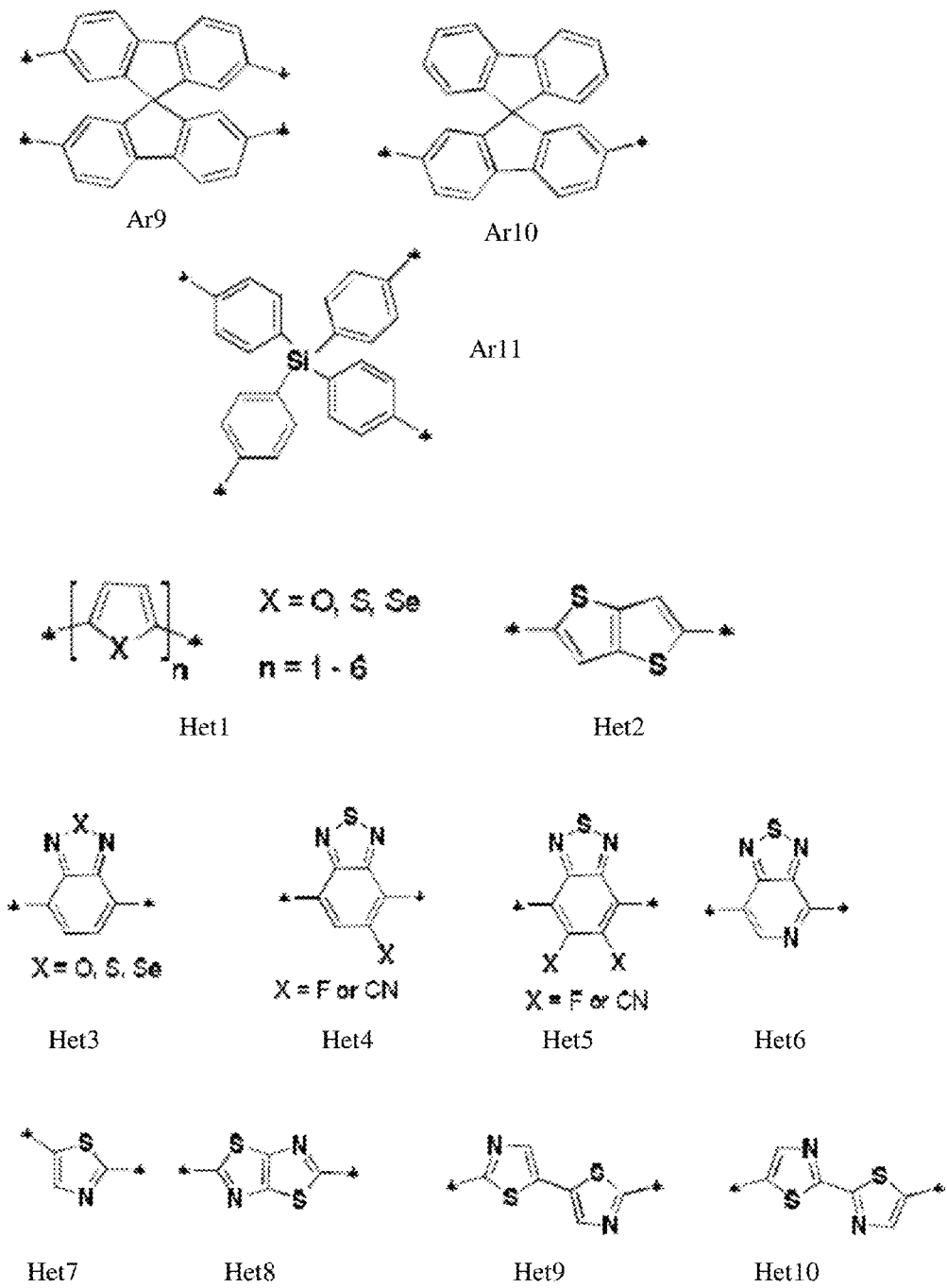
Figure 1C:
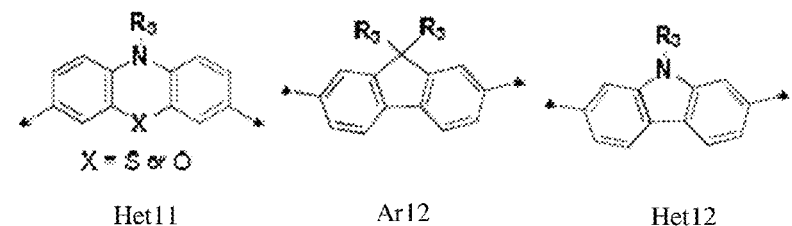
Figure 1C:
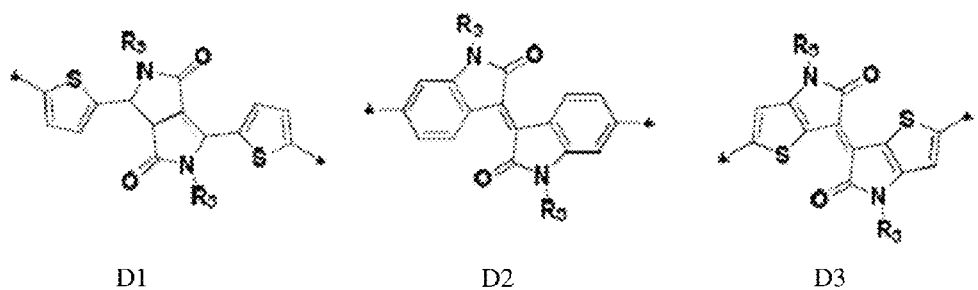
Figure 1C:
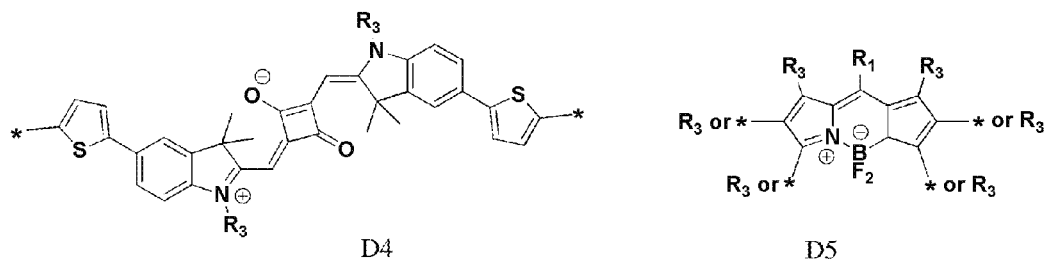

The present disclosure relates to N-annulated PDI materials as illustrated in Formulas herein. It is demonstrated that the inclusion of an alkyl chain at the pyrrolic N atom imparts a significant degree of solubility to the material. This allows for a lower density of aliphatic carbon chains compared to many other PDI materials that have only the imide positions at which to attach solubilizing alkyl chains. The modular effect of the alkyl chain at the pyrrolic N atom on solar cell performance is examined.

Non-brominated N-annulated PDI material of Formula I can be subjected to standard bromination protocols, resulting in a high yield of a novel synthon that can be used to make PDI materials (such as those of Formulas III and IV) analogous to the highly successful PDI electron acceptors currently used in fullerene-free organic solar cells.

N-annulation is used herein to describe incorporation of a nitrogen heteroatom in a 5-member ring formed at one bay position of the perylene core as shown in Formula I.

The term alkyl refers to a monovalent group formally derived from a saturated hydrocarbon group by removal of a hydrogen. An alkyl group has the general formula $C_nH_{2n+1}$. Alkyl groups can be straight-chain (linear) or branched. Alkyl groups herein can have 1-30 carbon atoms and more preferably 1-20 carbon atoms. Branched alkyl groups herein can have 3-30 carbon atoms and more preferably 3-20 carbon atoms. Straight-chain alkyl groups include those having 1-3 carbon atoms, 1-6 carbon atoms, 4-8 carbon atoms, 6-10 carbon atoms, and 6-20 carbon atoms, among other groups of carbon atom range. Straight-chain alkyl groups include methyl, ethyl, propyl, hexyl, heptyl, octyl, nonyl, decyl, dodecyl individually or in any combination. Branched alkyl groups include isopropyl, iso-butyl, sec-butyl, 1-ethylpropyl, 1-propylbutyl, 1-butylpentyl, 1-pentylhexyl, 1 hexylheptyl, 1-heptyloctyl, 1-octylnonyl, 1 nonyldecyl, 2-ethylhexyl individually or in any combination. Branching may occur anywhere along the alkyl chain from the site of attachment of the alkyl group. For example, a branch may occur at the first carbon (as in a 1-ethylpropyl group). The branching can occur for example at the second carbon along the chain (e.g., 2-ethylhexyl). There may be multiple branches along the chain (e.g., 1-ethyl-5-methylhexyl). In specific embodiments, a branched alkyl chain has one branching point which is at the first, second or third carbon from the site of attachment.

A divalent alkyl group is called an alkylene group herein. Such a group is attached between two other moieties by formation of a bond to two carbons in the group. The alkylene group can also be called a linker.

In certain compounds of this disclosure, a divalent, trivalent or tetravalent moiety links two, three or four PDI-derived groups, e.g., Formula III or VI. Divalent moieties useful in compounds of the invention include alkynylene groups, containing 1 triple bond, such as:

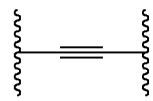 [SMILES: *C#C*]

or dialkynylene groups, containing 2 triple bonds, such as:

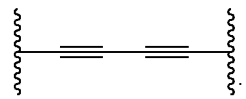

A divalent arylene moiety is derived from an aromatic hydrocarbon formally by removal of two hydrogens. A trivalent arylene moiety is derived from an aromatic hydrocarbon formally by removal of three hydrogens. A tetravalent arylene moiety is derived from an aromatic hydrocarbon formally by removal of four hydrogens. Arylene groups herein include those derived from an aromatic hydrocarbon have one or more aromatic hydrocarbon rings which include those with fused rings. More specifically, the arylene group can include 1, 2, 3 or 4 aromatic rings. In specific embodiments, arylene groups are optionally substituted with one or more alkyl groups, halogens or CN groups.

Divalent moieties include arylene groups having available two sites of attachment:

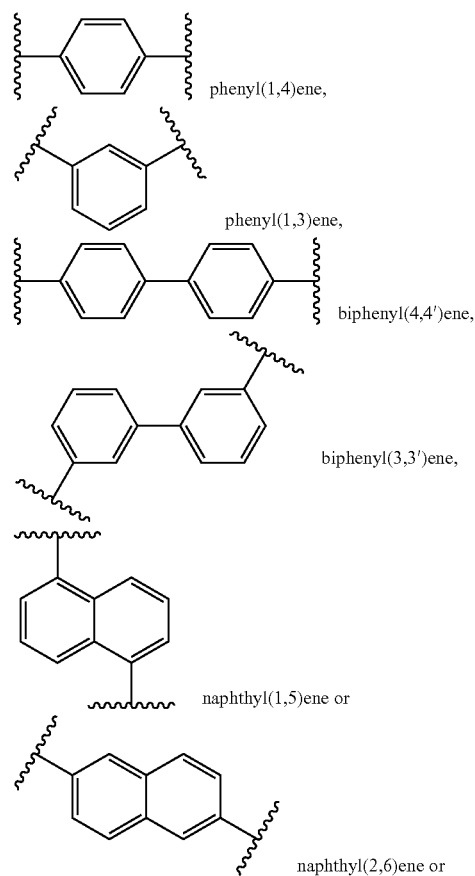

phenyl(1,4)ene, phenyl(1,3)ene, biphenyl(4,4')ene, biphenyl(3,3')ene, naphthyl(1,5)ene or naphthyl(2,6)ene or -continued

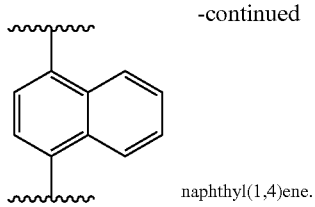

naphthyl(1,4)ene.

Exemplary divalent moieties for M and M1 include linking moieties of formulas:

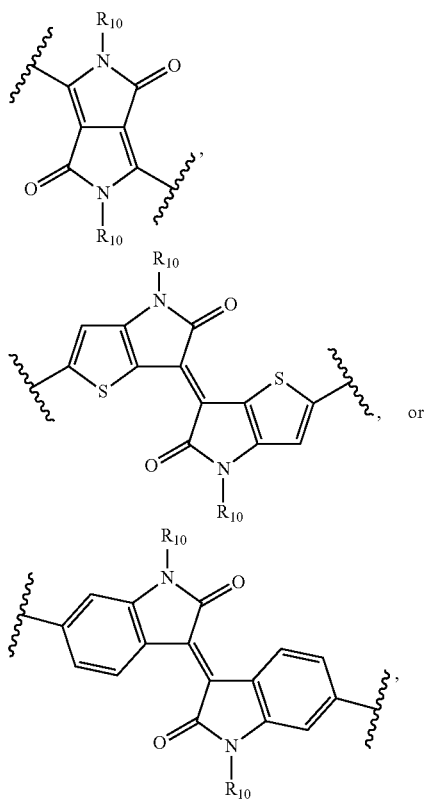

where each $R_{10}$, independently, is a straight-chain alkyl of 1-30 carbon atoms or a branched alkyl of 3-30 carbon atom. More specifically, each $R_{10}$ is a straight-chain alkyl of 6-12 carbon atoms. More specifically, each $R_{10}$ is a straight-chain alkyl having 8-20 carbon atoms. More specifically, each $R_{10}$ is a branched alkyl having 3-6 carbon atoms or 5-8 carbon atoms. More specifically, each $R_{10}$ is a branched alkyl having 6-12 carbon atoms.

An exemplary trivalent aryl moiety includes among others those having one-four aromatic rings and three sites for attachment. An exemplary trivalent aromatic linker is:

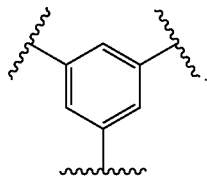 [SMILES: *c1cc(*)cc(*)c1]

A divalent arylene moiety is derived from an aromatic hydrocarbon formally by removal of two hydrogens. A trivalent arylene moiety is derived from an aromatic hydrocarbon formally by removal of three hydrogens. A tetravalent arylene moiety is derived from an aromatic hydrocarbon formally by removal of four hydrogens. Arylene groups herein include those derived from an aromatic hydrocarbon have one or more aromatic hydrocarbon rings which include those with fused rings. More specifically, the arylene group can include 1, 2, 3 or 4 aromatic rings. In specific embodiments, arylene groups are optionally substituted with one or more alkyl groups, halogens or CN groups.

Di-, tri- or tetravalent aromatic linkers include those where the aromatic rings are bonded to each other by one or more single bonds (as in biphenylenes above) and are also exemplified by:

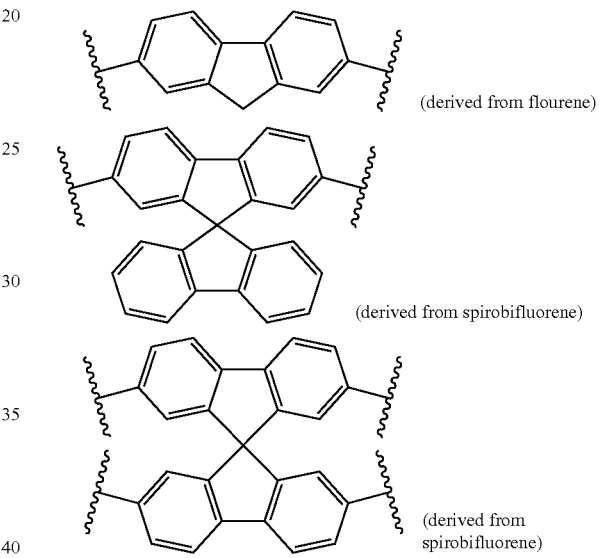

(derived from flourene)

(derived from spirobifluorene)

(derived from spirobifluorene)

Each of the exemplified linkers above is optionally substituted with one or more alkyl groups, halogens, nitro groups or CN groups.

Di-, tri- or tetra valent aromatic linkers include those wherein the aromatic rings are bonded to each other through carbon or a heteroatom (e.g., Si) or a heterocyclic group, for example,

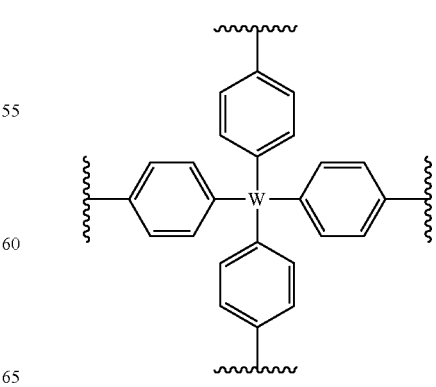

where W is C or Si,

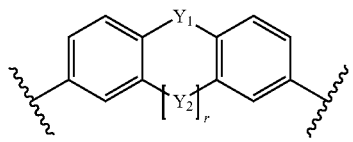

where $Y_1$ is —$NR_4$— or —$C(R_4)_2$, $Y_2$ is —S—, —O—, or —$C(R_4)_2$, r is 0 or 1 to show the presence or absence of $Y_2$ (when $Y_2$ is absent the central ring has 5 carbons), and each $R_4$ independently is hydrogen or an alkyl having 1-30 carbon atoms. In specific embodiments, each $R_4$ is independently hydrogen, a straight-chain alkyl having 1-20 carbon atoms or having 1-10, or having 3-10, or having 1-3 carbon atoms, or having 1-6 carbon atoms, or having 4-8 carbon atoms or a branched alkyl having 3-20 carbon atoms, or 3-12 carbon atoms or 3-8 carbon atoms.

Di-, tri- or tetravalent linkers include those which are derived from heteroaromatic compounds. Heteroaromatic compounds include those having one or more aromatic rings which have at least one heteroatom, e.g., N, O or S. In specific embodiments, heteroaromatic compounds have at least one 5- or 6-member heteroaromatic ring. In a specific embodiment, the heteroaromatic linker can be an oligomer having 1-8 repeats of the heteroaromatic ring(s).

Divalent heteroaromatic linkers include:

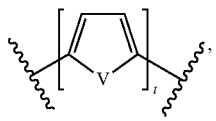

where V is O, S or Se and t is 1, 2, 3, 4, 5, 6, 7 or 8.

Additional exemplary M and M1 groups are illustrated in FIGS. 1A-1D.

It will be appreciated that trivalent and tetravalent moieties or groups illustrated in FIGS. 1A-1D can be converted into divalent groups by substitution of one or two hydrogens, alkyl groups (e.g., a $C_{1-12}$, $C_{1-6}$, $C_{6-12}$, $C_{1-3}$, $C_{3-9}$ or $C_{3-6}$ alkyl group) or another non-hydrogen substituent (e.g., a nitro group, a cyano group or a halogen) at one (for trivalent moieties) or two (for tetravalent moieties) of the possible bonding sites (marked with *) on the moiety. Similarly a tetravalent moiety can be converted to a trivalent moiety.

Figure 1D:
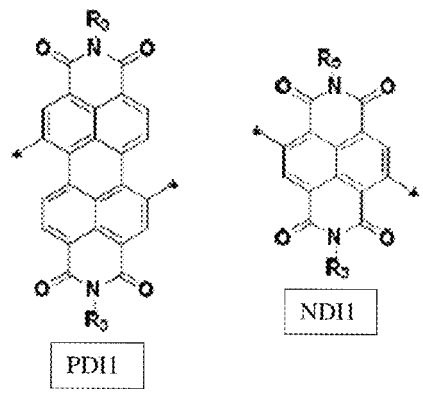
Figure 1D:
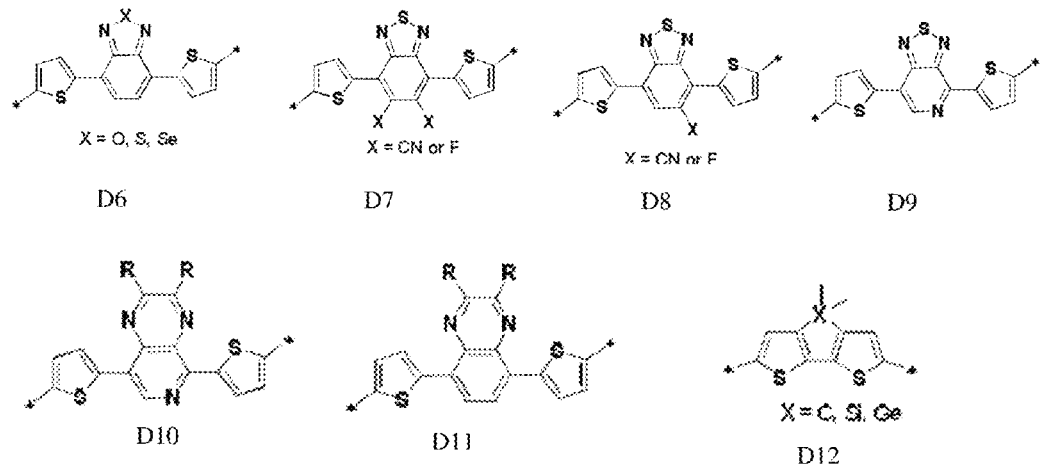

In additional embodiments, M1 is a divalent or tetravalent perylene diimide, such as structure PD1. (FIG. 1D)

In additional embodiments, M1 is a divalent naphthylene diimide, such as structure ND1. (FIG. 1D)

It is noted that compounds of the invention include those where two PDI-derived groups are joined by a single bond.

In specific embodiments of Formula IV:
p is 0 and n is 3;
p is 1 and n is 3;
$M_1$ is Ar7 or Ar8;
$M_1$ is D5;
p is 0 and n is 4;
p is 1 and n is 4;
$M_1$ is Ar6, Ar9 or Ar11;
$M_1$ is D5;
$M_1$ is D1-D5 and $R_3$ in the $M_1$ moiety is a straight-chain alkyl having 1-20 carbon atoms or a branched alkyl having 3-20 carbon atoms;
$M_{1-}$ is D6-D9;
$M_1$ is D10-D12 wherein each R in the $M_1$ moiety is hydrogen or a straight-chain alkyl group having 1-20 carbon atoms or a branched alkyl having 3-20 carbon atoms; $M_1$ is D1-D5 or D10-D12 and $R_3$ in the $M_1$ moiety is a straight-chain alkyl having 1-10 carbon atoms or a branched alkyl having 3-12 carbon atoms and each R in the $M_1$ moiety is hydrogen or a straight-chain alkyl group having 1-10 carbon atoms or a branched alkyl having 3-12 carbon atoms;
$M_1$ is D1-D5 or D10-D12, $R_3$ in the $M_1$ moiety is a straight-chain alkyl having 3-8 carbon atoms or a branched alkyl having 3-10 carbon atoms and each R in the $M_1$ moiety is hydrogen or a straight-chain alkyl group having 3-8 carbon atoms or a branched alkyl having 3-10 carbon atoms.

In an embodiment the disclosure provides compounds of formula:

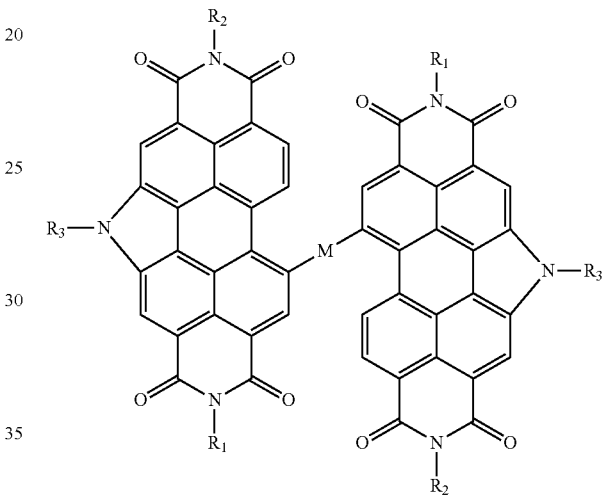

where $R_1$ and $R_2$ are independently selected from a straight-chain alkyl having 1-30 carbon atoms and a branched alkyl having 3-30 carbon atoms; and
$R_3$ is independently selected from a straight-chain alkyl having 1-30 carbon atoms and a branched alkyl group having 3-30 carbon atoms; and In specific embodiments of Formulas II and IV, M and M1 are a diketopyrrolopyrrole.

In specific embodiments of Formulas herein M or $M_1$ is

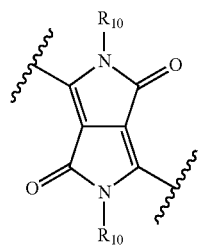

where each $R_{10}$ independently is a straight-chain alkyl having 1-30 carbon atoms or a branched alkyl group having 3 to 20 carbon atoms. In more specific embodiments, $R_{10}$ is a straight-chain alkyl group having 6-12 carbon atoms.

As to any of the above groups which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

In embodiments herein, a method for making the compound of formula I where X is Br, which comprises the step of bromination of a compound of formula V:

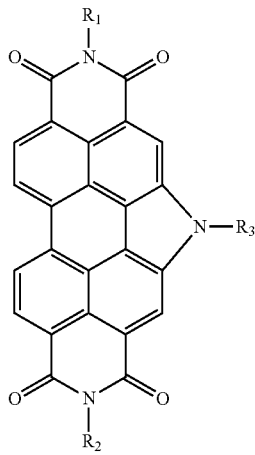

in an organic solvent in which the compound of formula V is soluble at room temperature in a molar excess of $Br_2$ with respect to the compound of formula V. In an embodiment, the solvent used is dichloromethane. In an embodiments, formula V is formed from perylene tetracarboxylic anhydride.

In an embodiment, the method further comprises:
preparing an N,N'-dialkyl PDI by reaction of an appropriate alkylation agent with perylene tetracarboxylic anhydride;
nitrating the N,N'-dialkyl PDI to form a mono-nitro N,N'dialkyl PDI of formula VII;
performing reductive cyclization on the mono-nitro N,N'dialkyl PDI of formula VII to form a compound of formula VIII having a bay N-containing ring; and
N-alkylating the compound of formula VII to form a compound of formula V.

In specific embodiments, the reductive cyclization employs triphenylphosphine as a base.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds of the invention, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

In an aspect, the disclosure relates to an improved method for synthesis of brominated PDI compounds which can function as useful synthons for compounds of formulas III and IV.

A synthetic route proceeds to an N-annulated PDI material (such as exemplified herein) which is then subjected to standard bromination protocols, resulting in a high yield of the novel synthon.

As exemplified in Scheme 1, the target PDI dimer (7) was synthesized by starting with the commercially available perylene tetracarboxylic anhydride (1). The anhydride 1 was functionalized with an N-alkyl moiety through heating in molten imidazole with excess of 3-amino pentane (alkylation reagent) following literature procedures [38] to provide EP2-PDI (2) in 94% yield. Next, $NO_2$—PDI (3) was synthesized n 80% yield by electrophilic aromatic nitration of the PDI core in dichloromethane with excess of nitric acid. [39] The inclusion of a nitrogen containing ring at the bay positions of the PDI chromophore was accomplished using a reductive cyclization reaction known as a Cagodan cyclization as previously reported by Langhals and co-workers. [39] Initially, triethylphosphite was used as the reducing agent; However, this resulted in low yields (30-40%) due to the production of an unwanted N-ethyl by-product during the course of the reaction. This by-product can be avoided by using triphenylphosphine as the reducing agent, as reported by Freeman et al. in the synthesis of carbazole-based materials. [39,40] Using this procedure for the reductive an isolated yield of 62% for NH-PDI (4) is provided after workup using column chromatography to remove the expected phosphorus containing by-products from the reaction. [39] NH-PDI (4) was then alkylated using microwave synthesis at 170° C. for one hour with potassium carbonate and n-hexyl bromide resulting in an 80% yield of (5) after purification using column chromatography to remove residual starting materials. Bromination of the alkylated N-annulated PDI (5) proceeded easily with excess bromine in dichloromethane at room temperature, a reaction which is highly selective in mono-bromination and goes to completion in approximately two hours giving 94% isolated yield of (6) after purification using column chromatography.

It should be noted that the order of synthetic steps is important to provide high yield in this series of reaction. Starting from compound 1, the synthesis proceeds by initial alkylation in molten imidazole to provide an N,N'-dialkyl PDI (such as compound 2). The mono-$NO_2$—N,N'-dialkyl PDI is then prepared by electrophilic aromatic nitration. Reductive cyclization is then used to form the N-ring at the bay position of the N,N'-dialkyl PDI. Preferably the reductive cyclization employs triphenyl phosphine as the reducing agent. The N of the N-ring in the bay position of the N,N'-dialkyl PDI with bay N-ring is then alkylated.

In an embodiment, the disclosure provides a method of synthesis of compounds of formula I where X is Br, wherein bromination is carried out on an intermediate of formula V, where $R_1$, $R_2$ and $R_3$ are as defined for formula III or IV above.

In an embodiment, the method includes a step of forming an N,N'-dialkyl PDI from perylene tetracarboxylic anhydride by reaction with an amino alkyl group in molten imidazole. The N,N'-dialkyl PDI compound is nitrated to form a compound of formula VII:

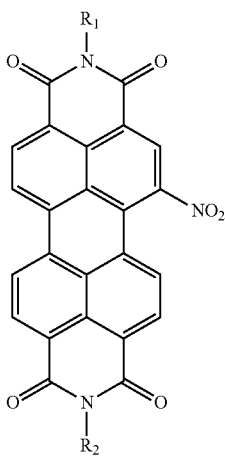

where $R_1$ and $R_2$ are as defined in formulas III and IV. The mono-nitrate compound of formula VII is then subjected to reductive cyclization to form a compound of formula VIII:

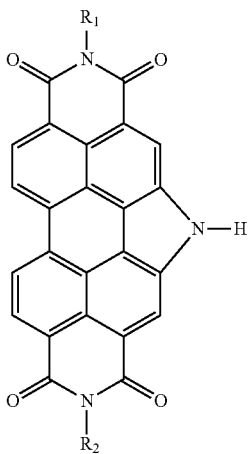

where $R_1$ and $R_2$ are as defined in formulas III and IV. This intermediate is then N-alkylated to form the corresponding compound of formula V. Finally, the compound of formula V is brominated to form the corresponding compound of formula I where X is Br.

In specific embodiments, synthetic reactions are carried out as described in the Examples herein with the proviso that starting materials for alkylation reactions are chosen to obtain the desired alkyl substituents at $R_1$, $R_2$ and $R_3$.

One of ordinary skill in the art will recognize that starting materials and reagents other than those specifically disclosed in the Examples can be employed in the reactions herein without resort to undue experimentation. One of ordinary skill in the art knows how to select appropriate starting materials for alkylation and to if necessary adjust the solvent employed.

In embodiments, the disclosure provides an electronic device employing an electron acceptor wherein the electron acceptor is one or more compounds of formulas herein and particularly of Formulas III and IV.

In embodiments, the disclosure provides an organic solar cell which comprises one or more compounds of any one of the formulas herein which is an electron acceptor and particularly one or more compounds of formulas III or IV.

In embodiments, the disclosure provides an organic thin film transistor which comprises one or more compounds of any one of the formulas herein which is an electron acceptor and particularly one or more compounds of formulas III or IV.

In embodiments, the disclosure provides a redox flow battery which comprises one or more compounds of any one of the formulas herein which is an electron acceptor and particularly one or more compounds of formulas III or IV.

Those of ordinary skill in the art will appreciate that methods for the preparation of organic solar cells, organic thin film transistors and redox flow batteries are known in the art and can be applied employing materials of the formulas herein and particularly one or more compounds of formulas III and IV herein. In view of what is known in the art and what is described herein one of ordinary skill in the art can employ materials described and characterized herein in such devices without resort to undue experimentation.

Additional details of the synthesis, characterization and application of materials of this disclosure are provided in Hendsbee et al. 2016 [66]; McAfee et al. 2017 [67] and Dayneko et al. 2017 [68] and the supporting information of each of these references which is freely available on-line for the publisher. Each of these references and the corresponding supporting information is incorporated by reference herein in its entirety for such additional details including synthetic methods, purification methods, characterization of compounds and methods for such characterization, construction and testing of organic solar cell, structure and components of organic solar cells.

All references throughout this application, for example patent documents including issued or granted patents or equivalents; patent application publications; and non-patent literature documents or other source material; are hereby incorporated by reference herein in their entireties, as though individually incorporated by reference. All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1: Synthesis

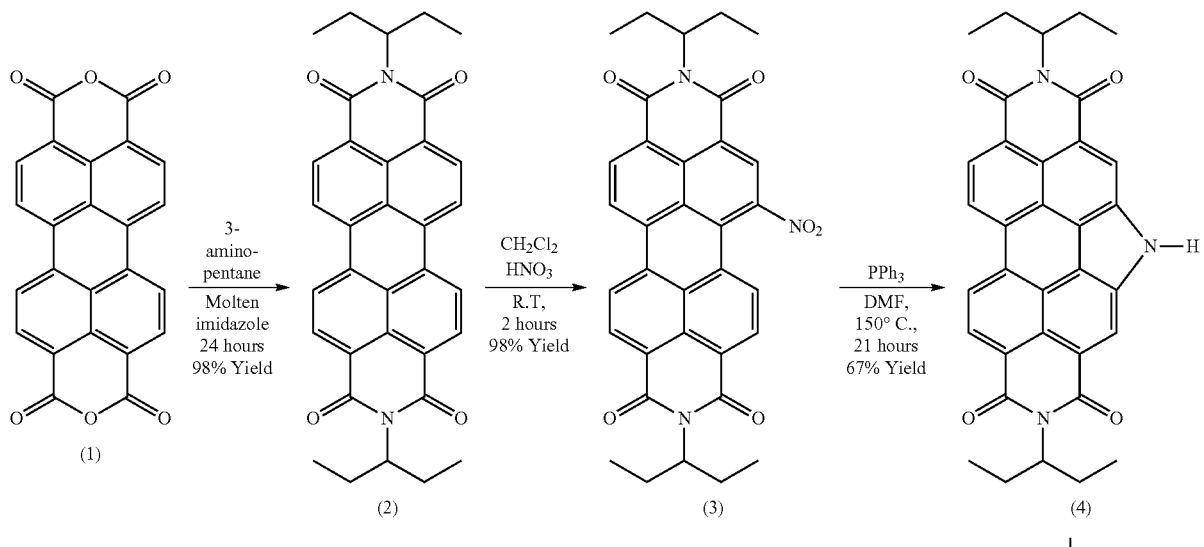

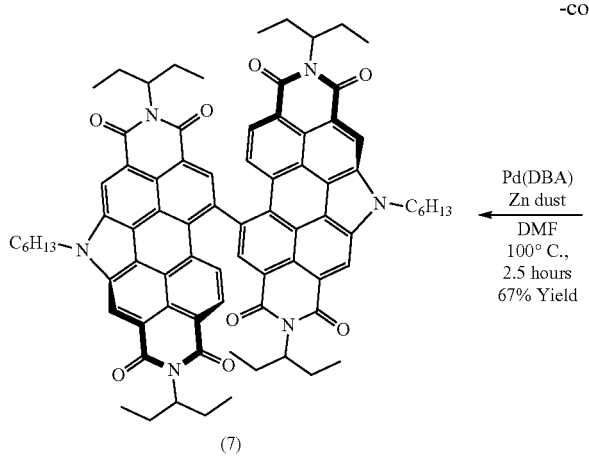

(7)

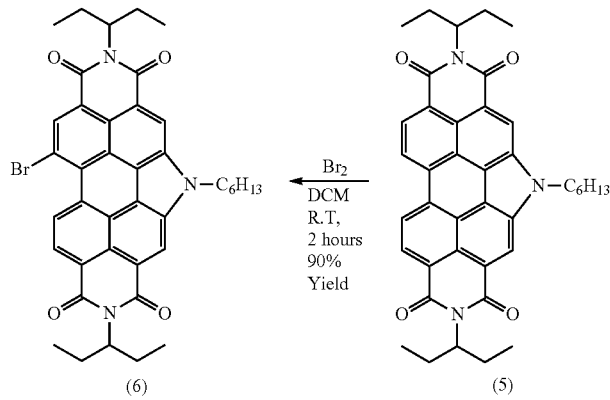

(6) (5)

The N-annulated PDI dimer (Formula II) is synthesized (as illustrated in Scheme 1) by starting with perylene tetracarboxylic dianhydride (e.g., compound 1). The anhydride is functionalized with an N-alkyl moiety by heating it in molten imidazole with an excess of 3-amino pentane following literature procedures, providing EP2-PDI (e.g., compound 2). [38] Next, $NO_2$—PDI (e.g., compound 3) is synthesized by electrophilic aromatic nitration of the PDI core in appropriate organic solvent (e.g., dichloromethane) with excess nitric acid. [39] The inclusion of the nitrogen containing ring at the bay positions of the PDI chromophore is accomplished using a reductive cyclization reaction known as a Cadogan cyclization, as previously reported by Langhals and co-workers. [39] Initially, triethylphosphite was used as the reducing agent; however, this was found to result in low yields, due to the production of an unwanted N-ethyl byproduct during the course of the reaction. This byproduct can be avoided by using triphenylphosphine as the reducing agent, as reported by Freeman et al. in the synthesis of carbazole based materials. [39,40] Using this procedure for the reductive cyclization, a much higher yield for NH-PDI (e.g., compound 4) is obtained after workup using silica-gel column chromatography to remove the expected phosphorus containing byproducts from the reaction. [39] The NH-PDI is alkylated to give the N-alkylated N-annulated PDI (e.g., compound 5) in high yield using microwave synthesis techniques.

Bromination of the N-alkylated N-annulated PDI proceeded in a matter of hours with excess bromine in dichloromethane at room temperature. The reaction is highly selective for monobromination at the bay position and the brominated N-annulated PDI derivative (e.g., compound 6) is isolated in high yield after purification.

In a specific example, commercially available perylene tetracarboxylic anhydride (1) is heated in molten imidazole with an excess of 3-amino pentane following literature procedures to provide EP2-PDI (2) in 94% yield. $NO_2$—PDI (3) is synthesized in 80% yield by electrophilic aromatic nitration of the PDI core in dichloromethane with excess nitric acid. The nitrogen containing ring at the bay positions of the PDI chromophore is prepared by reductive cyclization reaction using triphenylphosphine as the reducing agent. Using this procedure for the reductive cyclization for NH-PDI (4) is obtained in isolated yield of 62% after workup using column chromatography. NH-PDI (4) is then alkylated using microwave synthesis at 170° C. for one hour with potassium carbonate and n-hexyl bromide resulting in an 80% yield of (5) after purification using column chromatography to remove residual starting materials.

Bromination of the alkylated N-annulated PDI (5) proceeds with excess bromine in dichloromethane at room temperature, a reaction which is highly selective in monobromination and goes to completion in approximately two hours giving 94% isolated yield of (6) after purification using column chromatography.

The brominated N-annulated PDI (e.g., compound 6) is a valuable synthon that can be used to make a variety of electron deficient pi-conjugated materials.

In order to demonstrate the utility of the novel brominated PDI synthon (e.g., compound 6) a 'twisted PDI' material, as illustrated with compound 7, was prepared. This twisted PDI belongs to a class of materials that are of significant interest in the art due to their ability to act as electron transporting materials in organic solar cells. To form the homo-coupled PDI species (e.g., compound 7), a zinc/bis(dibenzylideneacetone)-palladium(0)catalyst system in N,N'-dimethylformamide at 100° C. for 3 is employed to convert the brominated PDI to the twisted dimer. This reaction when conducted with compound 6 gives nearly quantitative crude yields of the product 7 via $^1$H NMR.

In order to remove by-products and metal contaminants from the reaction, rigorous purification involving column chromatography and recrystallization from isopropanol is employed resulting in a 67% isolated yield for the bay-linked PDI dimer (compound 7). Specifically for preparation of compound 7, the reaction contents is passed through a solid $SiO_2$ support, followed by purification using silica-gel column chromatography (hexane to dichloromethane gradient). The product fraction is slurried with Celite 545 for 1 h and filtered through a second solid support ($Al_2O_3$).

Given the simple nature of many of these reactions, and a growing realization of the importance of more sustainable synthetic routes [41-44] a large scale, column chromatography free synthesis of compounds (2)-(7) was developed. Column chromatography is not practical for purification of organic electronic materials on an industrial scale due the large volumes of solvent and inorganic mediums required, which is not atom economical. [44]

A large scale, column free synthesis of (6) starting with 10 g of (1) provides excellent yields of pure compounds (2)-(7) without the use of column chromatography. The overall yield for compound (6) is ~50% when performed without the use of column chromatography. This is comparable to the optimized yields for the synthesis of mono- or di-bromo bay unsubstituted PDI materials, which require extensive purification using chromatography and recrystallization due to the formation of isomers [45, 46]. In addition, due to the versatile and modular nature of the alkylation used to create the N-alkylated N-annulated PDI (e.g., compound 5), the method in combination with synthetic methods that are well-known in the art, can be used to prepare a wide array of compounds bearing different substituents at the bay position in order to tailor self-assembly and solubility of N-annulated PDI dimers (e.g., compound 7).

General Synthetic Details:

Reactions are carried out on a bench top or under an atmosphere of dry, $O_2$-free $N_2$ where indicated. For reactions requiring heat, the conventional method involved submerging the reaction vial in a LabArmor® bead bath and heating on a hot plate at the desired temperature. For reactions that made use of microwave-assisted synthesis a Biotage® Initiator+ microwave reactor was used. The operational power range of this instrument is 0-400 W using a 2.45 GHz magnetron.

Materials:

All materials and solvents were purchased from Sigma-Aldrich unless indicated otherwise. Homogeneous catalyst Pd(DBA) was purchased from STREM chemicals and use without further purification.

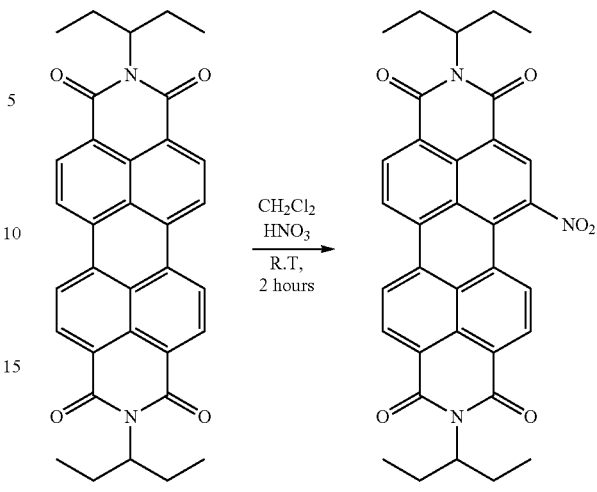

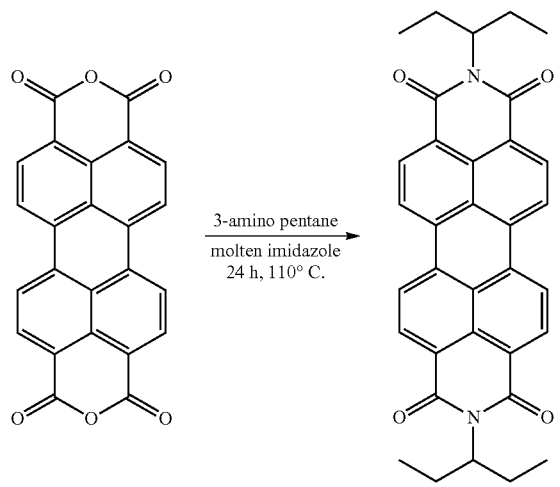 [SMILES: O=C1OC(=O)c2ccc3c4ccc5c6c(ccc(c7ccc1c2c73)c64)C(=O)OC5=O ; CCC(CC)N1C(=O)c2ccc3c4ccc5c6c(ccc(c7ccc(c2c37)C1=O)c64)C(=O)N(C(CC)CC)C5=O]

Synthesis of EP-PDI (2):

The synthesis of EP-PDI was carried out using previously reported reaction conditions from the literature. [38] Yield: 94%. Spectroscopic data for this compound matched those previously reported.[1]

Scaled up Synthesis of EP-PDI (2):

The synthesis of EP-PDI was carried out using previously reported reaction conditions from the literature. [38] Yield: 98%. Spectroscopic data for this compound matched those previously reported. [38]

Synthesis of EP-NO2-PDI (3):

The synthesis of EP-NO2-PDI was carried out using previously reported reaction conditions from the literature. [64] EP-PDI ((2), 2.6 g, $4.9*10^{-3}$ mol) was added to a 250 mL round bottom flask containing a stir-bar. Dry dichloromethane ~150 mL was then added using a solvent purification system. While stirring, concentrated nitric acid (6.0 g, 4.0 mL) was added drop-wise. After the complete addition of $HNO_3$, the reaction mixture was allowed to stir under air for 2 hours. At this time TLC analysis indicated the complete conversion to the desired product. The reaction mixture was then extracted with water and dichloromethane. The aqueous phase was then neutralized with sodium hydroxide. Solvent was removed from the organic phase using a rotary evaporator resulting in a red solid which was slurried in methanol and filtered to obtain a bright red solid. Yield 2.71 g (96%). $^1$H NMR (Chloroform-d, TMS/ppm) δ 8.75-8.56 (m, 6H), 8.23-8.22 (m, 1H), 5.03-5.00 (m, 2H), 2.29-2.16 (m, 4H), 1.99-1.86 (m, 4H), 0.89 (t, 12H, $^3J_{H-H}$=7 Hz). $^{13}$C NMR (Chloroform-d, TMS/ppm) δ 147.74, 135.52, 132.97, 129.53, 129.41, 129.16, 127.94, 127.56, 126.67, 126.50, 124.49, 124.03, 58.25, 57.96, 25.00, 24.91, 11.30, 11.27

Scaled Up Synthesis of EP-NO2-PDI (3):

The synthesis of EP-NO2-PDI was carried out using previously reported reaction conditions from the literature. [64] EP-PDI ((2), 10 g, $1.9*10^{-2}$ mol) was added to a 1 L round bottom flask containing a stir-bar. Dry dichloromethane ~500 mL was then added using a solvent purification system. While stirring, concentrated nitric acid (20 g, 13.3 mL) was added drop-wise. After the complete addition of $HNO_3$, the reaction mixture was allowed to stir under air for 2 hours. At this time TLC analysis indicated the complete conversion to the desired product. The reaction mixture was then extracted with water and dichloromethane. The aqueous phase was then neutralized with sodium hydroxide. Solvent was removed from the organic phase using a rotary evaporator resulting in a red solid which was slurried in methanol and filtered to obtain a bright red solid. Yield 10.73 g (98%).

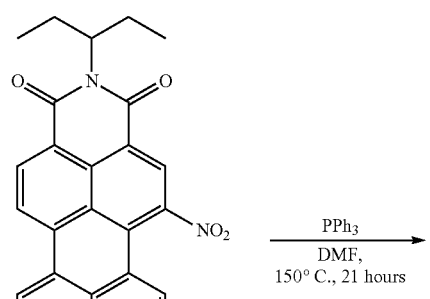

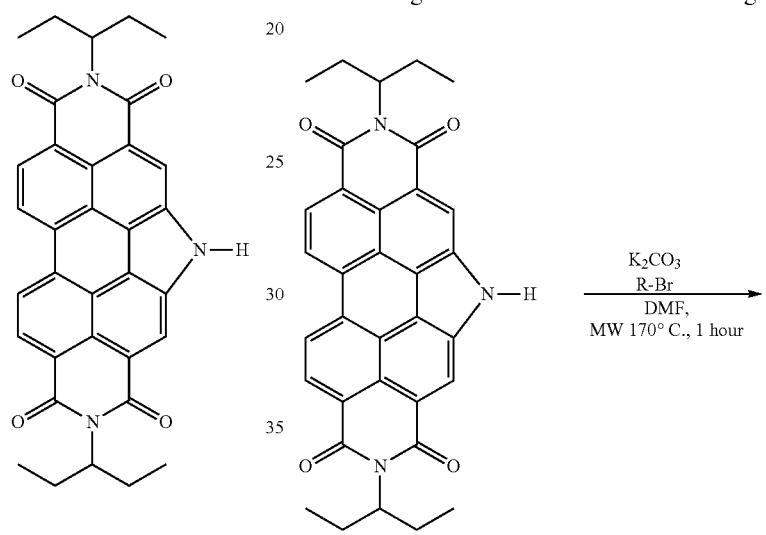

Synthesis of EP-NH-CAG-PDI (4):

The synthesis of EP-NH-CAG-PDI was carried out using a modified literature procedure. [40] EP-NO2-PDI ((3), 2.7 g, $4.7*10^{-3}$ mol) and triphenylphosphine (4.0 g, $1.5*10^{-2}$ mol) were combined in a 100 mL Schlenk flask with a stir-bar. The flask was sealed with a septa and approximately 60 mL dry N,N'-dimethylformamide was added using a syringe. The reaction mixture was purged with nitrogen for 5 minutes, followed by heating at 150° C. for 21 hours, at which time TLC indicated that starting material had been consumed. The reaction mixture was allowed to cool to room temperature and the solvent was removed using a rotary evaporator leaving a crude solid in the flask. The crude solid was loaded onto silica gel and purified using column chromatography (Hexane to Dichloromethane gradient, product eluted in 5% acetone in dichloromethane). The solvent was removed from the product fraction using a rotary evaporator resulting in a solid in the round-bottom flask which was taken up in a minimum of dichloromethane and precipitated into hexanes resulting in a red precipitate. The precipitated product was filtered using a Buchner funnel and rinsed with approximately 100 mL of hexanes to give a dark red solid. Yield: 1.6 g (61%). $^1$H NMR (Chloroform-d, TMS/ppm) δ 9.79 (s, 1H), 9.04-8.86 (m, 6H), 5.22-5.17 (m, 2H), 2.38-2.30 (m, 4H), 2.03-1.96 (m, 4H), 0.96 (t, 12H, 3JH-H=7 Hz). Due to the low solubility of compound (4) $^{13}$C NMR was not obtained.

Scaled Up Synthesis of EP-NH-CAG-PDI (4):

The synthesis of EP-NH-CAG-PDI was carried out using a modified literature procedure. [40] EP-NO2-PDI ((3), 10.73 g, $1.9*10^{-2}$ mol) and triphenylphosphine (15.9 g, $6.0*10^{-2}$ mol) were combined in a 500 mL Schlenk flask with a stir-bar. The flask was sealed with a septa and approximately 240 mL dry N,N'-dimethylformamide was added using a cannula transfer method. The reaction mixture was purged with nitrogen for 10 minutes, followed by heating at 150° C. for 23 hours, at which time TLC indicated that starting material had been consumed. The reaction mixture was allowed to cool to room temperature and the solvent was removed using a rotary evaporator leaving a crude solid in the flask which was taken up in a minimum of dichloromethane and precipitated into hexanes resulting in a red precipitate. The precipitated product was filtered using a Buchner funnel and rinsed with approximately 400 mL of hexanes to give a dark red solid. Yield: 6.81 g (67%).

Synthesis of EP-N-Hex-CAG-PDI (5):

The synthesis of EP-N-Hex-CAG-PDI was carried out using a modified literature procedure. [65] EP-NH-CAG-PDI ((4), 0.50 g, $9.2*10^{-4}$ mol) and potassium carbonate (0.25 g, $1.8*10^{-3}$ mol) were combined in a 20 mL microwave vial with a stir-bar. The vial was sealed with a Teflon® cap and approximately 20 mL Dry N,N'-dimethylformamide was added using a syringe followed by the addition of 1-bromo-hexane (0.27 g, $1.7*10^{-3}$ mol). The reaction mixture was purged with nitrogen for 5 minutes, followed by Microwave heating at 170° C. for 1 hour. The reaction mixture was allowed to cool to room temperature and was extracted using water and dichloromethane. The organic phase was collected and the solvent was removed using a rotary evaporator to give a crude solid. The crude product was loaded onto silica gel and purified using column chromatography (Hexane to Dichloromethane gradient. The product eluted at approximately 80% dichloromethane). The solvent was removed from the product fraction using a rotary evaporator resulting in a solid in the round-bottom flask which was slurried in methanol and filtered to give a dark red solid. Yield: 0.40 g (70%). $^1$H NMR (Chloroform-d, TMS/ppm) δ: 8.98-8.96 (m, 4H), 8.85-8.83 (m, 2H), 5.23-5.17 (m, 2H), 4.85 (t, 2H, $^3J_{H-H}$=7 Hz), 2.38-2.31 (m, 4H), 2.20-2.17 (m, 2H), 2.03-1.97 (m, 4H), 1.46-1.25 (m, 6H), 0.96 (t, 12H, $^3J_{H-H}$=7 Hz), 0.85 (t, 3H, $^3J_{H-H}$=7 Hz). $^{13}$C NMR (Chloroform-d, TMS/ppm) δ 134.18, 132.05, 124.06, 123.24, 121.19, 118.89, 57.21, 46.38, 30.94, 30.77, 26.28, 24.68, 21.90, 13.38, 10.94 LRMS (APCI). m/z exp: 628.31 obtained: 628.48.

Scaled Up Synthesis of EP-N-Hex-CAG-PDI (5):

The synthesis of EP-N-Hex-CAG-PDI was carried out using a modified literature procedure. [65] EP-NH-CAG-PDI ((4), 6.81 g, 1.3*10$^{-2}$ mol) and potassium carbonate (3.17 g, 2.3*10$^{-2}$ mol) were combined in a 250 mL Schlenck flask with a stir-bar. The flask was sealed with a septa and approximately 200 mL dry N,N'-dimethylformamide was added using a cannula transfer method. The reaction mixture was purged with nitrogen while reaching the reaction temperature of 120° C. at which time 1-bromo-hexane (3.08 g, 1.9*10$^{-2}$ mol) was added using a syringe. The reaction mixture was allowed to stir at a temperature of 120° C. for 18 hours under nitrogen. The reaction mixture was then allowed to cool to room temperature and was extracted using water and dichloromethane. The organic phase was collected and the solvent was removed using a rotary evaporator to give a crude solid. The crude solid in the round-bottom flask was slurried in methanol and filtered to give a dark red solid. Yield: 7.0 g (89%).

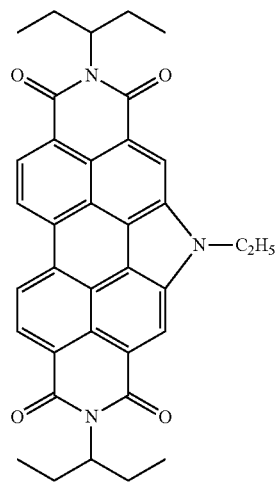

Synthesis of EP-N-Ethyl-CAG-PDI (5b):

The synthesis of EP-N-Ethyl-CAG-PDI was carried out in an identical manner to the synthesis of (5), by substituting hexyl bromide for an equimolar amount of ethyl bromide. Starting with 1 g of (4), 1.0 g of (5b) was obtained, (Yield: 96%). $^1$H NMR (Chloroform-d, TMS/ppm) δ: 9.03-9.00 (m, 4H), 8.88-8.86 (m 2H), 5.26-5.20 (m 2H), 4.97 (q, 2H, 3JH-H=7.5 Hz), 2.37-2.33 (m 4H), 2.01-1.98 (m, 4 h), 1.82 (t 4H 3JH-H=7.5 Hz), 0.97 (t, 12H, 3JH-H=7.5 Hz)

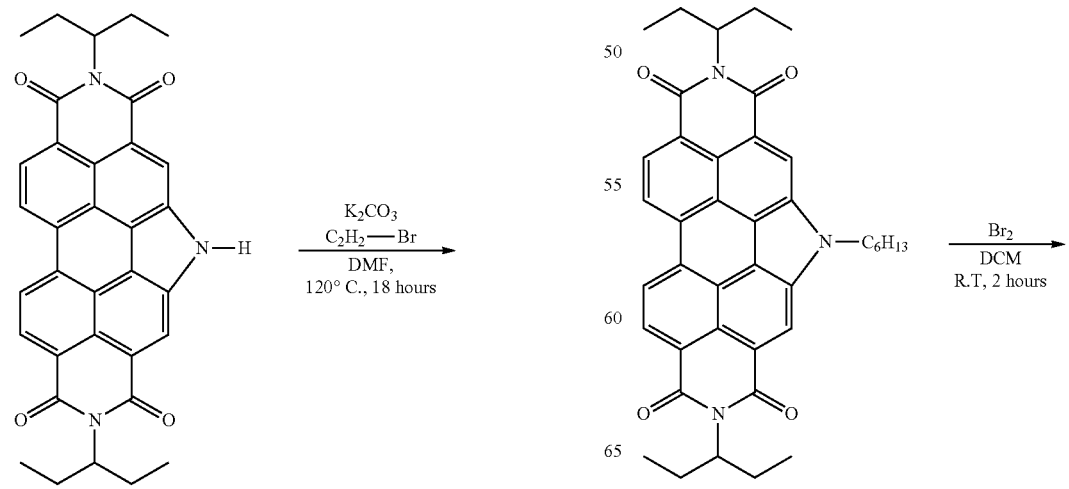

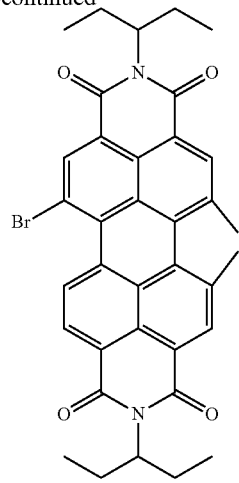
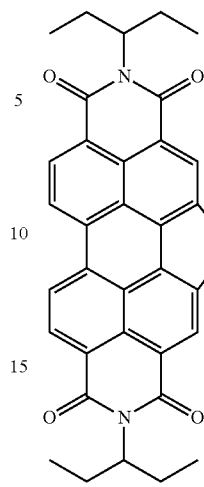

Synthesis of Br-EP-N-Hex-CAG-PDI (6):

The synthesis of Br-EP-N-Hex-CAG-PDI was carried out using a modified literature procedure. [3] EP-N-Hex-CAG-PDI ((5), 0.44 g, 9.2×10$^{-4}$ mol) was added to a 30 mL vial with a stir-bar. Approximately 25 mL of dichloromethane was added followed by a pipette full of Br$_2$ and the vial was sealed with a Teflon® cap. The reaction mixture was allowed to stir at room temperature for 2 hours at which time TLC analysis indicated the complete consumption of starting material. The excess of bromine was removed using air bubbling and solvent was removed using a rotary evaporator to give a crude solid. The crude solid was loaded on silica gel and purified using column chromatography (Hexane to Dichloromethane gradient. The product compound eluted at approximately 80% dichloromethane). The solvent was removed from the product fraction using a rotary evaporator resulting in a solid in the round-bottom flask which was slurried in methanol and filtered to give a dark red solid. Yield: 0.47 g (94%). $^1$H NMR (Chloroform-d, TMS/ppm) δ: 10.30-10.27 (m, 1H), 9.07-9.04 (m, 3H), 8.91-8.89 (m, 1H), 5.22-5.16 (m, 2H), 4.90 (t, 2H, $^3J_{H-H}$=7 Hz), 2.37-2.30 (m, 4H), 2.20-2.16 (m, 2H), 2.02-1.98 (m, 4H), 1.46-1.27 (m, 6H), 0.97 (t, 12H, $^3J_{H-H}$=7 HZ), 0.85 (t, 3H, $^3J_{H-H}$=7 Hz). $^{13}$C NMR (Chloroform-d, TMS/ppm) δ 134.36, 134.16, 132.12, 130.19, 127.33, 124.05, 123.46, 123.08, 121.95, 121.25, 118.58, 118.15, 58.07, 57.91, 46.82, 31.29, 26.82, 25.23, 25.17, 22.42, 13.88, 11.50. LRMS (APCI). m/z exp: 707.22, obtained: 707.44.

Scaled Up Synthesis of Br-EP-N-Hex-CAG-PDI (6):

The synthesis of Br-EP-N-Hex-CAG-PDI was carried out using a modified literature procedure. [3] EP-N-Hex-CAG-PDI ((5), 6.5 g, 1.0*10$^{-2}$ mol) was added to a 500 mL round bottom flask with a stir-bar. Approximately 250 mL of dichloromethane was added followed by six pipettes full of Br$_2$ and the vial was sealed with a Teflon® cap. The reaction mixture was allowed to stir at room temperature for 2 hours at which time TLC analysis indicated the complete consumption of starting material. The excess of bromine was removed using air bubbling and solvent was removed using a rotary evaporator to give a crude solid which was slurried in methanol and filtered to give a dark red solid. 1H NMR analysis indicated the presence of minor impurities in the aliphatic region, in order to remove these the dark red solid was stirred in ~50 mL hexanes for 30 minutes and filtered to give a red solid. Yield: 6.6 g (90%).

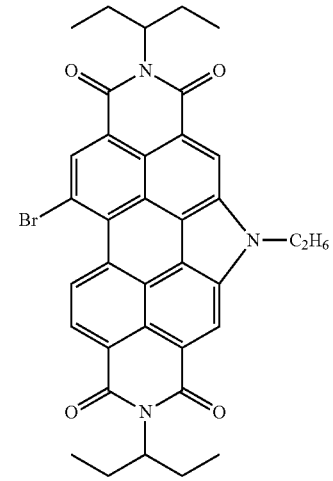

Synthesis of Br-EP-N-Ethyl-CAG-PDI (6b):

The synthesis of Br-EP-N-Ethyl-CAG-PDI was carried out in an identical manner to the synthesis of 6, by substituting the starting material with a hexyl chain (5) for (5b), bearing an ethyl chain. Starting with 1 g of (6b), 1.1 g of (6b) was obtained, (Yield: 98%). $^1$H NMR (Chloroform-d, TMS/ppm) δ: 10.23 (d, 1H, 3JH-H=9.5 Hz), 9.05 (m, 3H), 8.89-8.86 (m, 1H), 5.23-5.21 (m 2H), 4.99 (q, 2H, 3JH-H=7.5 Hz), 2.40-2.33 (m, 4H), 2.05-2.00 (m, 4H), 1.82 (t, 3H, 3JH-H=7.5 Hz), 1.00 (t, 6H, 3JH-H=7.5 Hz), 0.98 (t, 6H, 3JH-H=7.5 Hz).

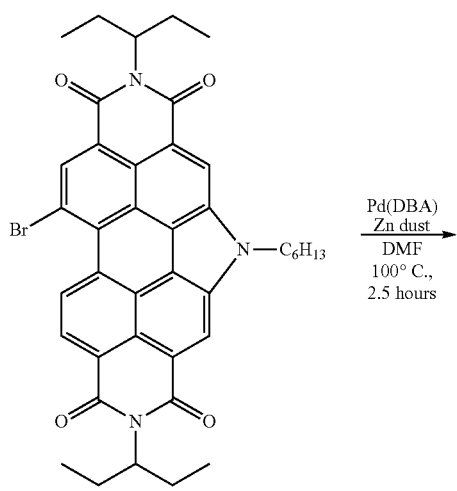

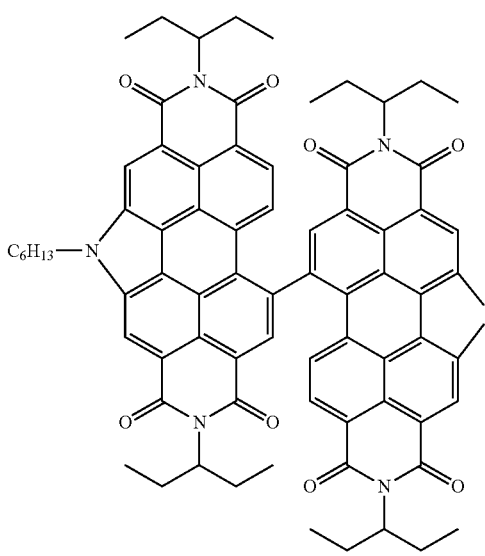

Synthesis of BAY-EP-N-Hex-CAG-PDI (7):

The synthesis of BAY-EP-N-Hex-CAG-PDI was carried out using a modified literature procedure. [3] Br-EP-N-Hex-CAG-PDI ((6), 0.38 g, $5.2*10^{-4}$ mol) and Zinc dust (170 mg, $2.6*10^{-3}$ mol) were added to a 20 mL microwave vial with a stir-bar. The vial was brought inside the glove-box where approximately 40 mg of Pd(DBA) was added. The vial was sealed under a nitrogen atmosphere using a Teflon® cap and was removed from the glove-box. 20 mL of N'N-dimethylformamide was added using a syringe and the reaction mixture was purged with nitrogen for 10 minutes. The reaction mixture was heated to 100° C. for 2.5 hours at which time TLC analysis indicated the complete consumption of starting material. The reaction mixture was passed through a silica plug to remove solids from the reaction and the solvent was removed using a rotary evaporator to give 395 mg of a dark red solid. $^1$H NMR analysis indicated that the crude product was produced in good yields, however some minor impurities remained in the aromatic region. The crude solid was loaded on silica gel and purified using column chromatography (Hexane to dichloromethane gradient, product elutes at approximately 80% dichloromethane). The solvent was removed from the product fraction using a rotary evaporator resulting in 360 mg of a dark red solid which still contained minor impurities in the aromatic region of the $^1$H NMR spectrum. The red solid was boiled in 100 mL of iso-propyl alcohol with vigorous stirring for approximately 1 hour, at which time it was allowed to cool to room temperature and filtered using a Buchner funnel, resulting in a bright red solid. Due to the nature of the reaction and the possibility of metal by-product contamination, the material was taken up in dichloromethane, slurried in Celite 545 and passed through an alumina plug. Solvent was removed using a rotary evaporator and the final product was slurried in hot Iso-propanol which was then cooled and filtered to give the product as a bright red solid. Yield: 0.16 g (49%). $^1$H NMR (Chloroform-d, TMS/ppm) δ: 9.23 (s, 2H), 9.05 (s, 2H), 8.85 (s, 2H), 5.21 (m, 2H), 5.00 (m, 6H), 2.41-2.24 (m, 8H), 2.24-2.09 (m, 4H), 2.05-2.91 (m, 4H), 1.90-1.75 (m, 4H), 1.59-1.50 (m, 4H), 1.47-1.37 (m, 4H), 1.37-1.29 (m, 4H), 1.03-0.73 (m, 30H). $^{13}$C NMR (Chloroform-d, TMS/ppm) δ 140.90, 135.28, 135.06, 132.911, 130.40, 126.83, 124.96, 124.72, 123.60, 122.78, 120.11, 119.85, 58.03, 57.64, 47.13, 31.67, 31.44, 27.00, 25.05, 22.52, 13.99, 11.50, 11.23. LRMS (APCI). m/z exp: 1253.61 obtained: 1253.84.

Scaled Up Synthesis of BAY-EP-N-Hex-CAG-PDI (7):

The synthesis of BAY-EP-N-Hex-CAG-PDI was carried out using a modified literature procedure. [3] Br-EP-N-Hex-CAG-PDI ((6), 1.0 g, $1.4*10^{-3}$ mol) and Zinc dust (450 mg, $6.9*10^{-3}$ mol) were added to a 250 mL schlenck flask with a stir-bar. The flask was brought inside the glove-box where Pd(DBA) (100 mg, $1.1*10^{-4}$ mol) was added. The flask was sealed under a nitrogen atmosphere using a rubber septa and was removed from the glove-box. 100 mL of N'N-dimethylformamide was added using a cannula transfer method and the reaction mixture was purged with nitrogen for 10 minutes. The reaction mixture was heated to 100° C. for 3 hours at which time TLC analysis indicated the complete consumption of starting material. The solvent was removed from the reaction mixture using a rotary evaporator and the crude product was loaded on silica gel. The product was purified using column chromatography (Hexane to dichloromethane gradient, product elutes at approximately 80% dichloromethane). The solvent was removed from the product fraction using a rotary evaporator resulting in 790 mg of a dark red solid. The red solid was boiled in 100 mL of iso-propyl alcohol with vigorous stirring for approximately 1 hour, at which time it was allowed to cool to room temperature and filtered using a Buchner funnel, resulting in a bright red solid. Due to the nature of the reaction and the possibility of metal by-product contamination, the material was taken up in dichloromethane, slurried in Celite 545 and passed through an alumina plug. Solvent was removed using a rotary evaporator and the final product was stirred in ~250 mL hot Iso-propanol which was then cooled to room temperature and filtered to give the product as a bright red solid. Yield: 0.57 g (65%).

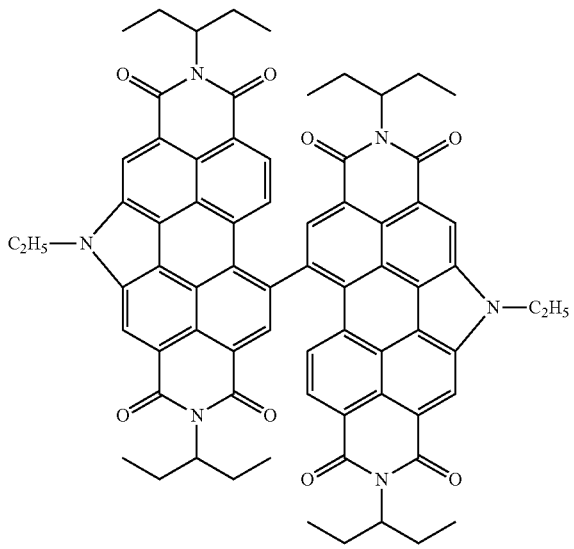

Synthesis of BAY-EP-N-Ethyl-CAG-PDI (7b):

The synthesis of BAY-EP-N-Ethyl-CAG-PDI was carried out in an identical manner to the synthesis of (7), by substituting the starting material with a hexyl chain (6) for (6b), bearing an ethyl chain. Starting with 1 g of (6b), 0.70 g of (7b) was obtained. (Yield: 79%). $^1$H NMR (Chloroform-d, TMS/ppm) δ: 9.29 (s, 2H), 9.11 (s, 2H), 8.88 (s, 2H), 7.97-7.95 (m, 2H), 7.67 (d, 2H, 3JH-H=8.5 Hz), 5.25-5.21 (m, 2H), 5.12 (q, 4H, 3JH-H=7.5 Hz), 5.02-4.98 (m, 2H), 2.37-2.35 (m, 4H), 2.34-2.18 (m, 4H), 2.04-1.97 (m, 4H), 1.93 (t, 6H, 3JH-H=7.5 Hz), 1.88-1.82 (m, 4H), 1.01 (t, 12H, 3JH-H=7.5 Hz), 0.81-1.80 (m, 12H).

Example 2: Characterization

Example 2: Methods and Instrumentation

Nuclear Magnetic Resonance (NMR):

Reported $^1$H and $^{13}$C NMR spectra were acquired on either Bruker Ascend 500 mHz, Avance 400 mHZ or DRX 400 mHz spectrometers all at 300 K. Chemical shifts are reported in parts per million (ppm) and are referenced to the external standard SiMe$_4$. All experiments were performed in deuterated chloroform (CDCl3). Multiplicities are reported as: singlet (s), doublet (d), triplet (t), doublet of doublets (dd), and multiplet (m).

Mass Spectrometry (MS):

Mass spectrometry measurements were performed in the Chemical Instrumentation Facility at the University of Calgary. All samples were run on an Agilent 6520 Q-TOF through direct infusion experiments with an Agilent 1200 series HPLC without a column. The flow rate was 0.2 mL/minute using methanol as the eluting solvent. The source conditions were a gas temperature of 300° C. with a flow of 10 L/min, a vaporizer temperature of 350° C. and a nebulizer pressure of 12 psi.

Cyclic Voltammetry (CV):

All Electrochemical Measurements were Performed Using a CH Instruments potentiostat in a standard three-electrode configuration equipped with a silver wire pseudo-reference, platinum wire counter electrode and glassy carbon working electrode. The cyclic voltammetry experiments were performed in an anhydrous solution of dichloromethane (CH$_2$Cl$_2$) with ~0.1 M tetrabutylammonium-hexafluorophosphate (TBAPF$_6$) supporting electrolyte. Samples were scanned at a rate of 100 mV/s following a dry N$_2$ purge to deoxygenate the solution. Solution CV measurements were carried out with a sample concentration of ~0.5 mg/mL in CH$_2$Cl$_2$. Estimations of the energy levels were obtained by correlating the onset ($E_{ox}$ Fc/Fc+, $E_{red}$ Fc/Fc+) to the normal hydrogen electrode (NHE), assuming a HOMO energy level of 4.80 eV for Fc/Fc+:

$$E(\text{HOMO})=-(E_{ox}+4.80), E(\text{LUMO})=-(E_{red}+4.80)$$

UV-Visible Spectroscopy (UV/Vis):

All absorption measurements were recorded using an Agilent Technologies Cary 60 UV-vis spectrometer at room temperature. All solution UV/vis experiments were run in chloroform (CHCl$_3$) using 2 mm quartz cuvettes and diluted 1% wt/v solutions. Thin-films were prepared by spin-coating 1% wt/v solutions from CHCl$_3$ onto Corning glass micros slides. Prior to use, glass slides were cleaned with soap and water, acetone and isopropanol, and followed by UV/ozone treatment using a Novascan UV/ozone cleaning system.

Example: Characterization

X-Ray Crystal Structures.

Of great importance within the current scope of organic semiconductor materials is the subject of their self-assembly. PDI materials are often strongly aggregated by π-π stacking interactions, a habit which is well documented in the literature and can lead to over-crystallization within a bulk heterojunction solar cell, hindering performance. Recently, dimeric PDI structures have been shown to suppress this over crystallization and have become an important class of non-fullerene acceptors, reaching PCE's of 8.4%. It is of interest to study the single crystal structures of the N-annulated PDI derivatives such as (5) and (7) to learn how the N annulation and subsequent dimerization affects the self-assembly of these chromophores.

Single crystals of compound (5) were grown from a solution of toluene with methanol layered on top. Compound (5) crystallized in monoclinic space group Cc with disordered toluene present in the unit cell. First it is noteworthy to discuss the effect of including the nitrogen heterocycle on the PDI skeleton. The PDI skeleton is noticeably "bowed", presumably caused by the shortening of one of the central C—C aromatic bonds in the structure. (C2-C19[1.37 Å] vs C4-C21[1.48 Å] bond distance). The overall PDI chromophore is rendered non-planar due to this deformation of the ring. This bowing upon inclusion of a 5-membered heterocycle into the 6-membered ring framework has been noted before by Wang et al., who used this strategy to make "bowl" shaped polycyclic aromatic hydrocarbons from PDI based materials. [53] Despite the bowed nature of the N-annulated PDI chromophore, there is still a strong degree of π-π interaction between chromophores with a π-π stacking distance of ~3.4 angstroms and a high degree of overlap between the chromophores.

In a similar fashion to compound (5), needle like crystals of compound (7) were grown from a solution of the compound in toluene, layered with methanol. The structure was solved by combination of real space refinement and conjugate-gradient refinement in the initial stages and then by full-matrix least squares and difference Fourier techniques at the final stages. Despite the low resolution of the data, it still provides valuable information about the connectivity and packing arrangement for compound (7). The molecules of (7) in the unit cell have an average torsion angle of 66(3)° between the two PDI chromophores, which is significantly less than the torsion angle (96°) calculated in gas-phase DFT calculations. This indicates that crystal packing forces, in addition to molecular structure, play a significant role in the solid state geometry of such "twisted" PDI small molecules, resulting in a more coplanar orientation of the chromophores. One molecule of the compound forms π-stacking interactions with two adjacent molecules, resulting in "pillars" of π-stacked (7). Interestingly these π-π stacking interactions appear to run in only the direction of the pillars and not in the directions between the pillars. In the interstitial spaces between the pillar-like superstructures of (7) the alkyl chains reside, providing the weak intermolecular interactions that join the pillars together. The 1-D charge transport pathways are intriguing, as it has often been hypothesized that such "twisted" PDI chromophores would form 3-D charge transport networks similar to fullerenes.

Solubility, Optical and Electronic Characteristics

Figure 2:
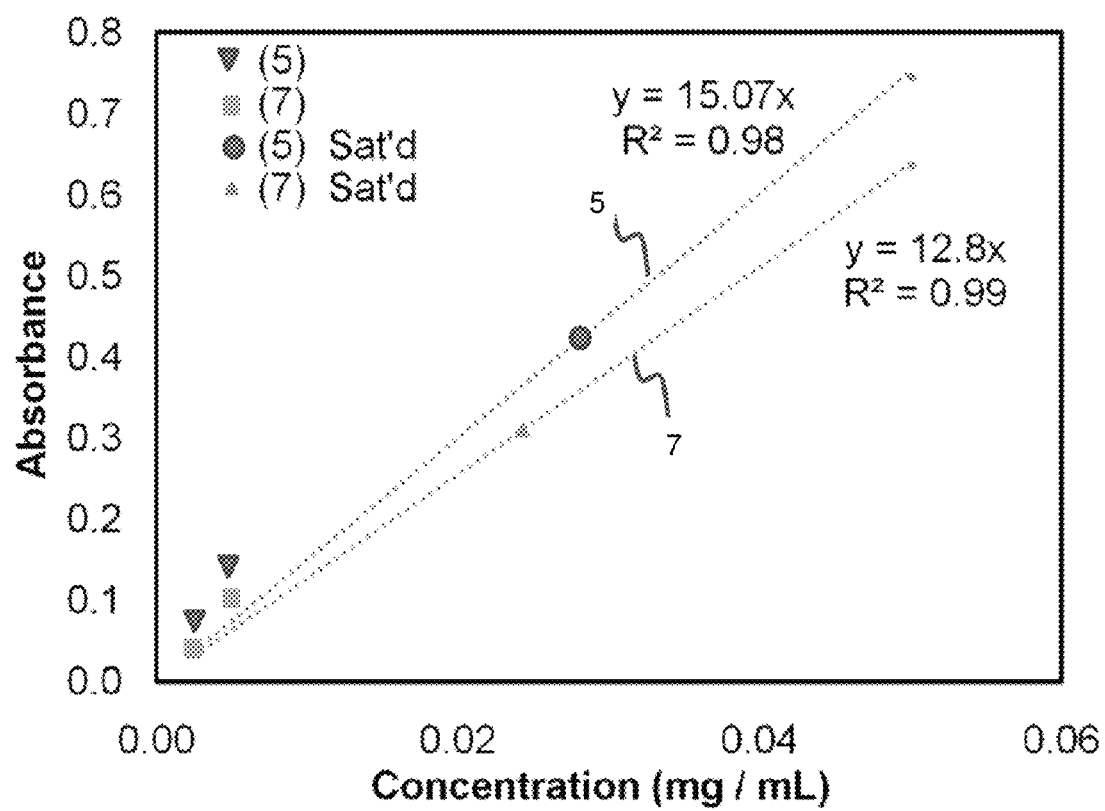
FIG. 2 is a concentration vs absorption plot for determining the solubility of compounds (5) and (7) in CHCl$_3$. A calibration curve was made for each compound by plotting absorbance values of known concentrations. (Dotted lines). In order to determine solubility, compounds (5) and (7) were made into solutions having 50 mg/mL concentration, allowed to stir overnight and then passed through a 0.45 μm syringe filter to remove any undissolved solids. The obtained solutions were then diluted by a factor of 2000 so that their absorbance was in the range of values used for the calibration curves. By using the Beer-Lambert law and the slope of the respective curves, it was determined that the solubility of both (5) and (7) was ~50 mg/mL. This observation is confirmed by the apparent complete dissolution of 50 mg/mL samples of either (5) or (7) in CHCl$_3$.
Figure 3A:
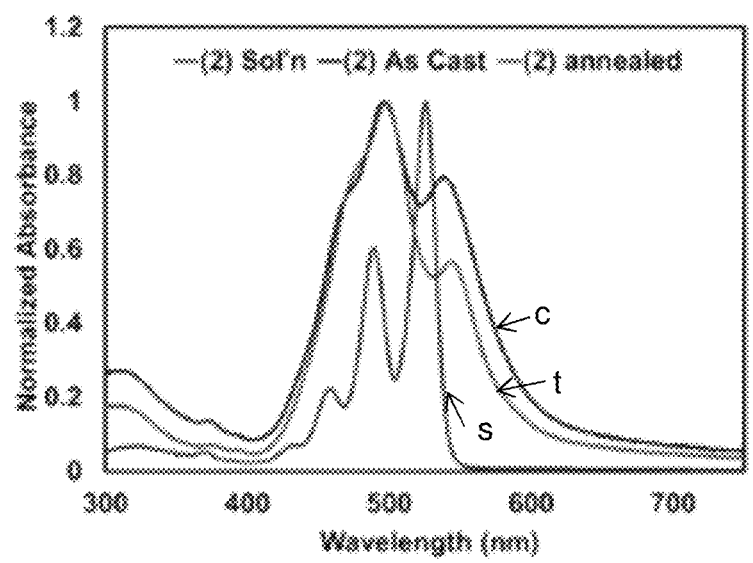
FIGS. 3A-3D are UV-vis absorption spectra (solution (s), as-cast film (c), and thermally annealed (t) film at 140° C.) for compounds (2), (4), (5), and (7), respectively.
Figure 3B:
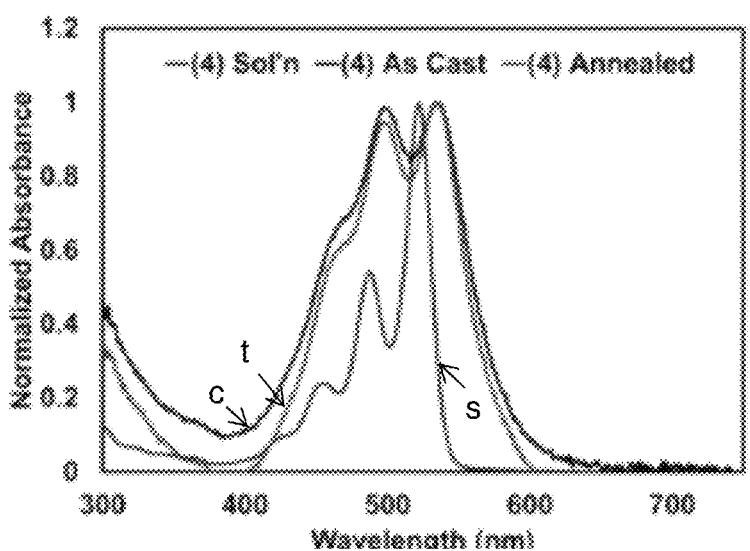
Figure 3C:
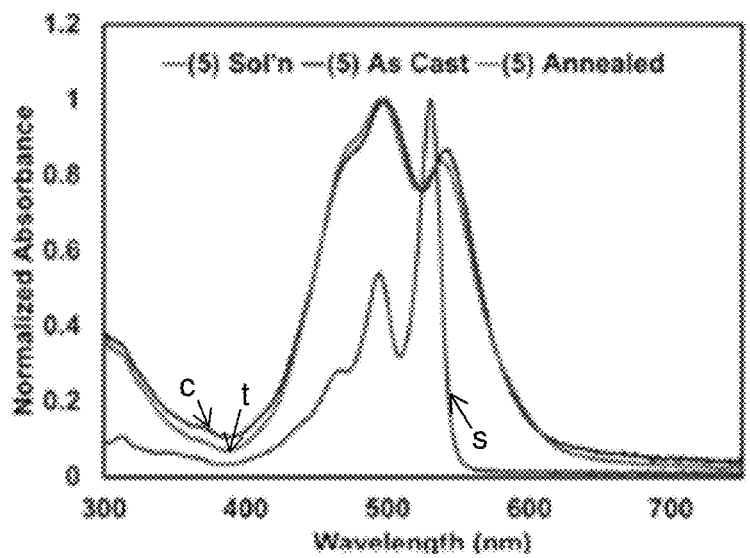
Figure 3D:
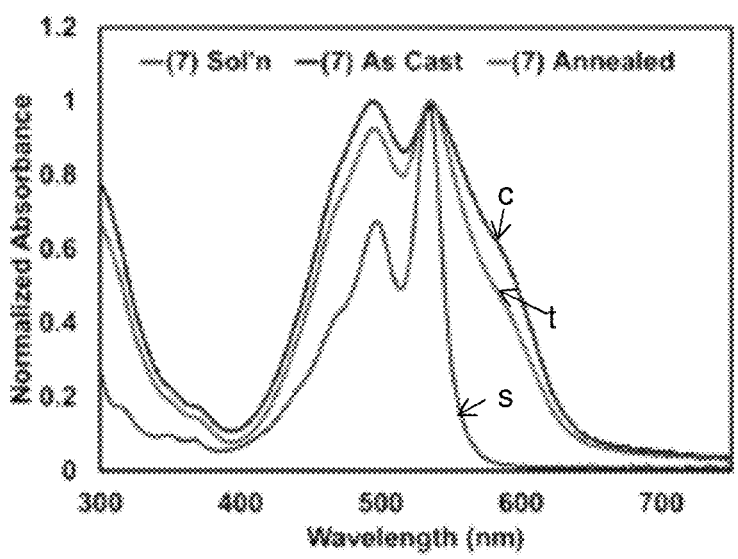
Figure 4A:
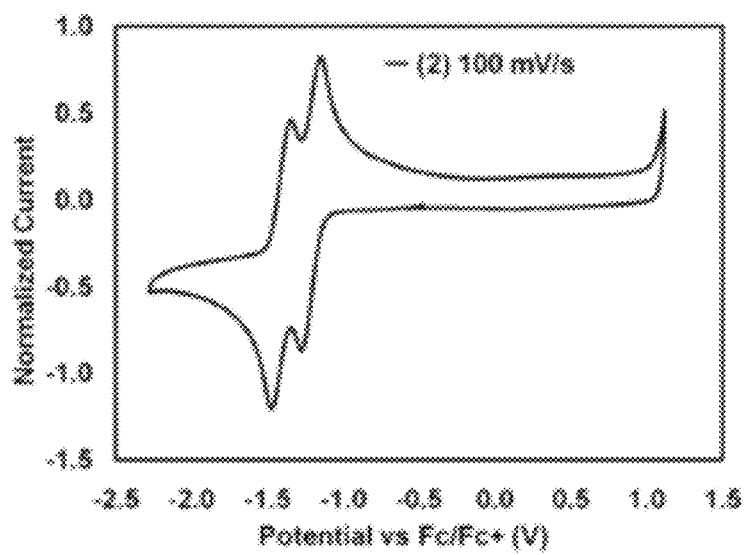
FIGS. 4A-D are cyclic voltammograms (100 mV/s vs Fc/Fc+) for compounds (2), (4), (5), and (7), respectively.
Figure 4B:
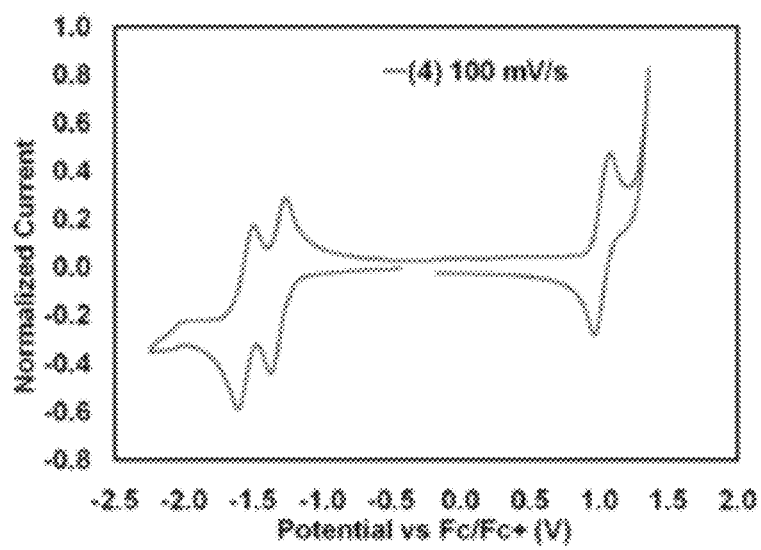
Figure 4C:
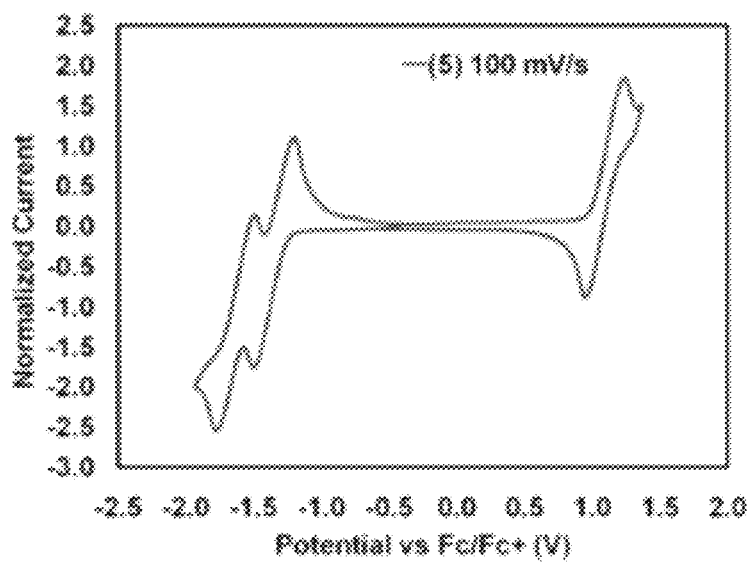
Figure 4D:
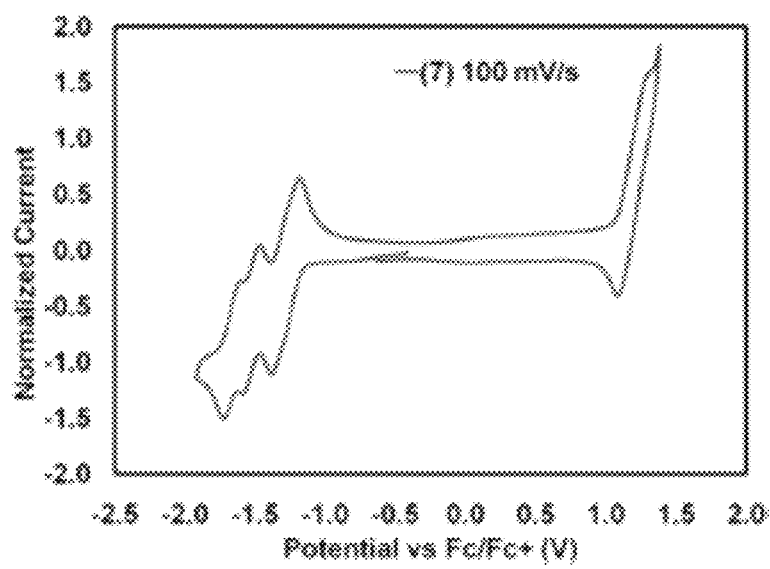

With the N annulated PDI derivatives (4), (5) and (7) in hand we set out to study their optical electronic and solubility characteristics. The N-annulated PDI materials bear an extra site for alkyl chain functionalization which was envisioned to modify the solubility and self-assembly characteristics of the materials with respect to the parent PDI compound (2). Firstly, the unalkylated n-annulated PDI (4), displays solubility lower than 1 mg/mL CHCl$_3$ which may be due to possible intermolecular hydrogen-bonding interactions between the N—H and C=O functional groups on adjacent perylene molecules in solution. This assertion is supported by $^1$H NMR evidence showing that the N—H proton becomes more deshielded upon increasing the solution concentration, typically observed for hydrogen bonding interactions (not shown). In contrast the The N-alkylated and Bay-linked-N-alkylated PDIs (5) and (7) showed excellent solubilities in CHCl$_3$ of >50 mg/mL (FIG. 2) at room temperature which is a beneficial trait for solution processed materials where the formation of viscous inks is desirable for the formation of thick films. [54] Importantly, such high organic solvent solubility is achieved without the need for long branched alkyl chains attached to the imide N atoms, chains that are used for almost all reported multi-PDI based materials. Thus, one can envision a wide array of alkyl chains being installed to fine-tune molecular assembly in the solid state, following the so-called "side chain engineering" methodology. [55]

The melting points of compounds (4), (5), and (7) were also determined and provide support for the assertion that compound (4) experiences intermolecular hydrogen bonding interactions. Compound (4) did not melt below 400° C., while compound (5), bearing a hexyl chain, melted at 235° C. and dimeric compound (7) melted at 380° C. All compounds were determined to be thermally stable up to ~395° C., with compound (7) having slightly higher decomposition temperature of ~425° C., as determined by TGA analysis. Dimerization improves thermal stability.

The solution and thin film optical profiles are shown in FIGS. 3A-3D for compounds 2, 4, 5 and 7, respectively. In solution, the optical profiles of the N-annulated PDI materials (4), (5), and (7) are relatively unchanged from that of the parent PDI chromophore (2), displaying a strong peak for the 0-0 transition at ~525 nm, and subsequently weaker peaks for the 0-1 and 0-2 electronic transitions at ~490 and 460 nm. 56,57 The 0-0 and 0-1 bands are well-defined for each molecule; however, the 0-2 band is less defined for compound (5) and even less defined for compound (7). Thin films of compounds (5) and (7) were spin-cast onto clean glass substrates from 10 mg/mL solutions in CHCl$_3$, while compound (4), due to its low solubility, was cast from a 0.5 mg/mL CHCl$_3$ solution. All compounds formed uniformly coated thin films using spin-casting without the need for heating or filtering of the substrate or solution, indicative of their good film forming tendencies. Similar to the parent PDI compound (2), the absorbance profiles of (4), (5), and (7) underwent significant changes upon transitioning from solution to film. Starting with (4), a red shift in λonset of ~60 nm, which is less than the ~75 nm shift observed for (2), suggesting different intermolecular electronic coupling for (4) due to the incorporation of the pyrrole ring and possible N—H—O hydrogen bonding. Strikingly, the absorption profile of (4) is vastly different from that of (2). In the thin film of (2) the peak for the 0-1 electronic transition is strongest, an effect often attributed to aggregation of the PDI chromophore. [56,57] In the thin film absorbance spectrum for compound (4), however, the 0-0 and 0-1 peaks are of equal intensity, suggesting a difference in self-assembly between (2) and (4) due to the presence of the pyrrole ring. Incorporation of the alkyl chain (compound (5)) results in a thin film absorbance profile reminiscent of the parent PDI (2). This is possibly due to π-π stacking forces once again becoming the dominant intermolecular force upon removal of the N—H—O hydrogen bonding scenario.

Comparing (5) to (7), λonset is red-shifted by 18 nm for (7) while there is an emergence of a low energy shoulder at ~586 nm. We attribute this to aggregation of the PDI chromophores in the solid state. Of note is the minimal change in λmax for compound (7) upon transition from solution to the thin film. Recent reports have suggested this is due to weak aggregation; [3,36] however, based on the crystal structure, discussed above, strong cofacial π-π stacking of the PDI molecules in the solid state is possible.

Thermally annealing the organic films of the N-annulated PDI derivatives up to 140° C. had minimal effect on the optical properties. This is in contrast to the parent PDI (2), in which a significant change in the absorbance profile is observed, implying a certain degree of morphological stability in the "as-cast" films of (4), (5), and (7).

The N-annulation of the PDI core provides an extra pair of nonbonding electrons from the nitrogen atom which might be expected to donate back into the 7-system of the PDI chromophore and slightly destabilize the frontier energy levels with respect to the parent PDI compound (2). Using cyclic voltammetry [58] (FIGS. 4A-D, 2, 4, 5 and 7, respectively), the ability of each compound to be oxidized and reduced was probed. All compounds show clean reversible reduction waves while only the N-annulated compounds displayed reversible oxidation waves. Using the onset of oxidation, the ionization potentials (IP) were estimated to be 5.8, 5.7, and 6.0 eV for compounds (4), (5), and (7), respectively, while the electron affinities (EA) were (estimated using the onsets of reduction) to be 3.6, 3.6, 3.5, and 3.8 eV for (2), (4), (5), and (7), respectively. These values are commonly associated with HOMO and LUMO energy levels, but it has recently been reported that the use of IP and EA is correct. [58] All energies are relative to vacuum and were obtained using a conversion factor of 4.8.59 The IP for compound (2) was estimated at 5.85 eV, similar to the reported literature value. [60] Comparatively, compound (4) is slightly easier to oxidize, as expected due to the incorporation of the electron rich pyrrole ring in the structure. Upon alkylation of this compound to form compound (5), a further decrease in ionization potential is observed, presumably due to the stronger electron donating effect of the alkyl chain vs a hydrogen atom. The bay-linked PDI derivative (7)

has a higher IP than the monomer (5), due to the attachment of the second electron withdrawing PDI unit. Compound (7) displayed four reversible reductions in the range −1.1 to −1.8 V (FIG. 4D), which can be expected from results of other bay-linked PDI materials in the literature that also feature four reversible reductions. [3,36] A notable feature for all of the N-annulated PDI materials is that they have the ability to be reversibly oxidized, a feature that is not seen in the parent PDI compound (2). It is also interesting to note that addition of an electron rich N-heterocyclic unit at the bay positions of PDI chromophores promotes such a reversibly oxidizable species, a trait that is not observed for the recently reported PDI molecules annulated at the bay positions with S or Se. [3,36]

Optical Switching Behaviour.

While examining the film forming properties of compound (7) a difference in the UV-Absorbance profiles for films cast from different solvents was noted. The absorption of the films cast from chlorobenzene was essentially unchanged from the absorption profile in dilute solution, having a strong 0-0 peak and a weaker 0-1 transition. The absorption profile of films cast from chloroform had features which are significantly broadened with changes to the vibronic structure, and the appearance of a low energy shoulder. There are several reports which discuss the aggregation of PDI chromophores through-pi-pi stacking interactions and it is generally agreed that the relative increase in intensity of the 0-1 transition vs. the 0-0 transition as well as the appearance of the low energy shoulder all result from chromophore-chromophore interactions. In order to further examine this effect, films were made from a variety of solvents and studied by UV-Visible spectroscopy and optical microscopy. 15 mg/mL solutions of compound (7) were made in each of the solvents (Chlorobenzene, 0-Xylenes, 2-Me-THF, 1,2-DCE, Dichloromethane, Chloroform, 1,1',2,2'-TCE and ethyl acetate) and cast at 1000 rpm onto PEDOT coated glass slides. Examining the UV-Visible profiles of these different films, it appeared that essentially two types of films were being formed, one which had the broadened features similar to the films cast from Chloroform CF (Type 1) and one which had the sharp, solution-like features of films cast from Chlorobenzene CB (Type 2). The absorption profiles of films cast from each solvent are available in the ESI for this material.

The starkest contrast in absorption profiles were seen between films made from CB and CF, so the study was continued using these solvents. To investigate this film forming behavior further, the films were annealed using either thermal annealing at 140° C. for 10 minutes or solvent vapor annealing with chloroform. These annealing techniques could transform the films from one of the optical behaviors to the other in the following manner: First, thermally annealing the films drives the optical behavior of the films towards the "Type 2" absorption profile. While solvent vapor annealing the films had the effect of driving the optical behavior towards the "Type 1" absorption profile. This behavior is found to be somewhat reversible, as the optical behavior of the films is switchable using repeated cycles of solvent annealing and thermal annealing. When a film is cast from CF, the "Type 1" profile is observed in addition to grain like features being observable on the microscope. For CB cast films, the "Type 2" absorption profile is observed with no features visible under the microscope. Overall, the grain size of the film is locked in by the choice of casting solvent, while the absorption profile remains tunable using the annealing procedures described above.

Example 4: Bulk Heterojunction Solar Cells

To probe the photovoltaic performance of the N-annulated PDI compounds, BHJ-OSCs were fabricated by blending (7) with the low-bandgap polymer poly({4,8-bis[(2-ethylhexyl)oxy]-benzo[1,2-b:4,5-b']dithiophene-2,6-diyl}{3-fluoro-2-[(2-ethylhexyl)carbonyl]thieno[3,4-b]thiophenediyl}) (PTB7). [61] In initial screening of various device architectures, the inverted structure (ITO/ZnO/BHJ/MoOx/Ag) (FIG. 5B) gave significantly better results and was used in this example.

Figure 5A:
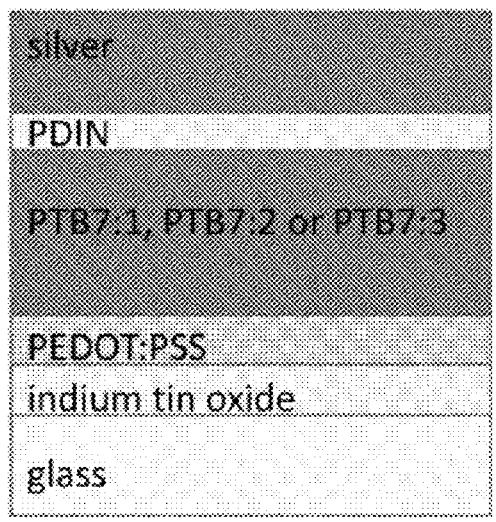
FIGS. 5A and 5b illustrate respectively the standard and inverted device architectures for the BHJ-OSCs.
Figure 5B:
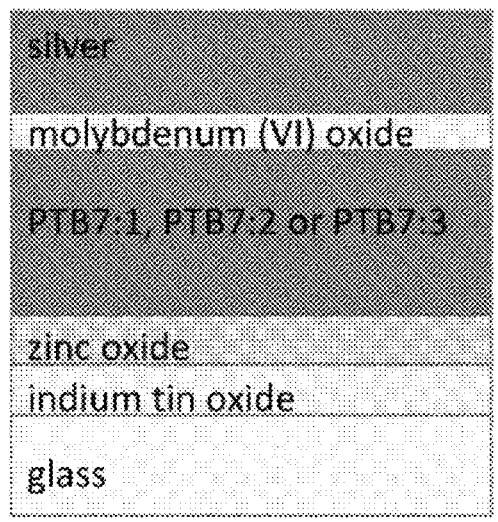
Figure 6A:
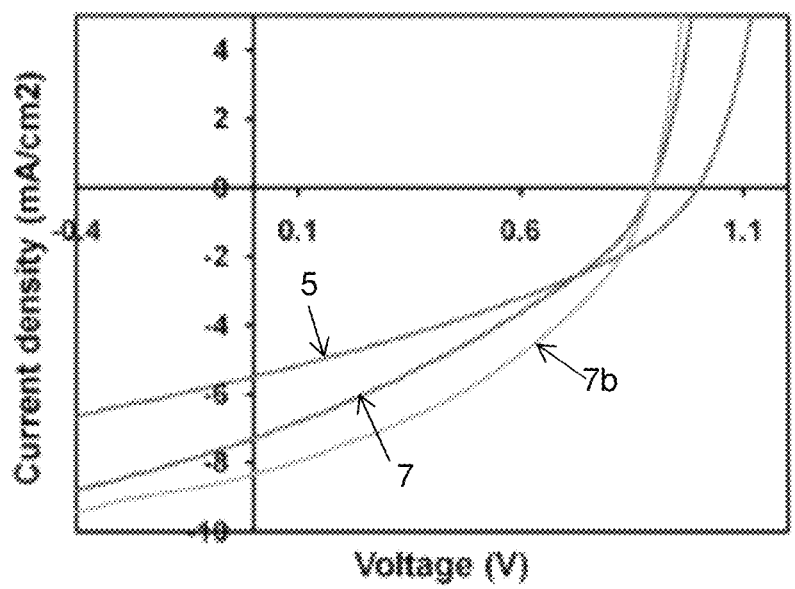
FIGS. 6A-6D. BHJ blends of PTB7 and PDI acceptors 5, 7, and 7b processed from CB solution with DIO additive. The device architecture used was ITO/Zno/BHJ/MoOx/Ag.
Figure 6B:
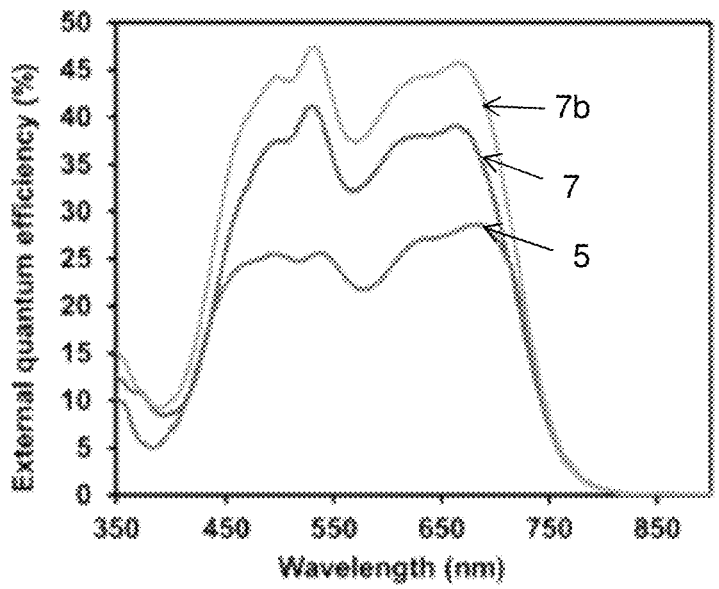
Figure 6C:
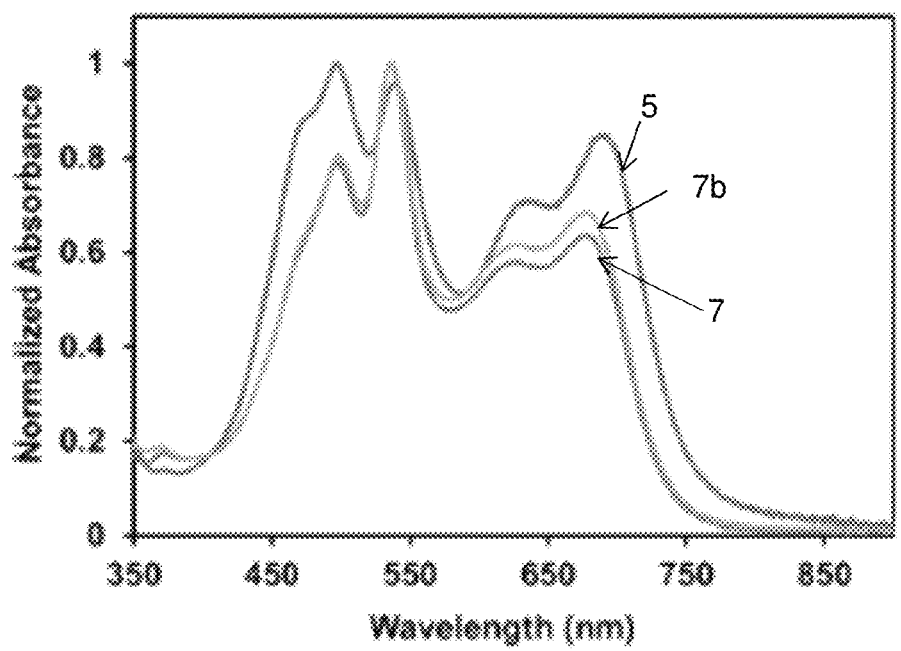
Figure 6D:
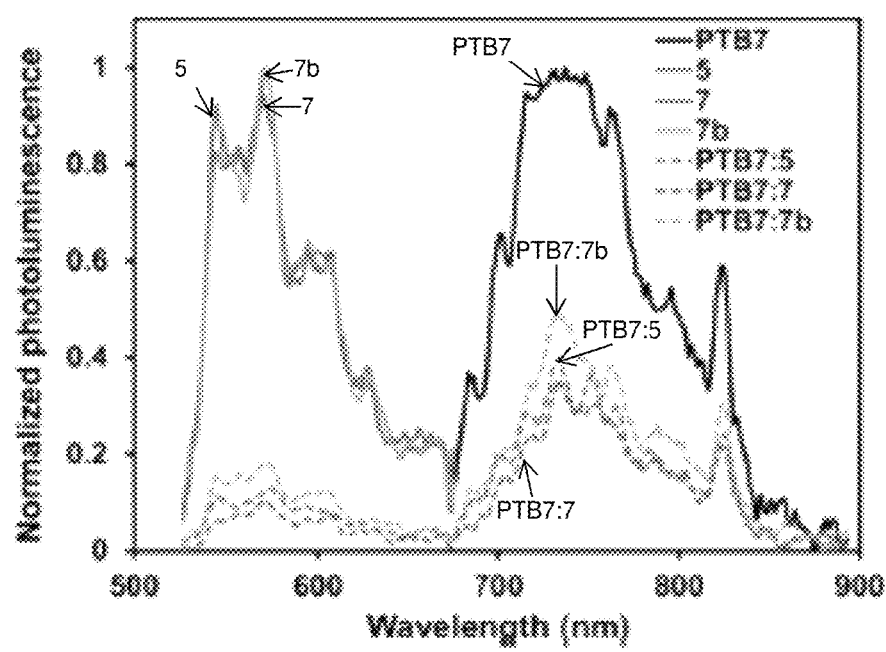

FIGS. 5A and 5B illustrate respectively the standard and inverted device architectures for the BHJ-OSCs.

In general, 25 mg/mL solutions of PTB7:(PDI) were cast from chlorobenzene at 1500 rpm onto patterned indium tin oxide (ITO) substrates coated with ZnO. $MoO_3$ was thermally evaporated onto the organic films, followed by Ag contacts through a shadow mask starting from a 50:50 blend ratio, the devices were thermally annealed which provided performance improvements to 1.4% power conversion efficiency (PCE). Next, 1,8-diiodooctane (DIO) was incorporated as a solvent additive and reached PCE of 2.2%, when a relatively large amount of DIO was added (8% v/v). In subsequent attempts to optimize the blend ratio with DIO additive fixed at 8%, inconsistent performance was observed between device batches. We rationalize that since DIO remains in the film until it is removed under vacuum during top contact deposition, [62] having a large amount of DIO can change film properties after casting if the amount of time and storage environment prior to contact deposition is not carefully controlled.

Following these results, compound 5 was screened under various DIO loadings and it was found that comparable performance could be realized using less DIO (4% v/v). Since DIO is a poor solvent for both PTB7 and the PDI chromophore, [56] it plays a large role in the formation of crystalline domains. [63] Despite being able to grow single crystals of (7) from solution, it was concluded that in the short-time scale regime of spin-cast film-formation, the twisted dimer configuration in conjunction with long hexyl chains at the annulated nitrogen hindered the formation of ordered domains and thus required the use of large amounts of DIO solvent additive during film formation.

This was rectified by substituting ethyl bromide for hexyl bromide in the synthesis of (5) (Scheme 1), resulting in a PDI dimer with ethyl side chains (compound 7b). This derivative achieved 3.1% PCE in a 50:50 blend with 3% DIO. We note that similar performance could be achieved with a range of DIO concentrations (2-4%) and higher acceptor loadings (40:60 and 30:70); thus, the favorable BHJ formation is not extremely sensitive to processing conditions. Also, being able to achieve similar performance with higher acceptor loading is desirable, since our acceptor molecules are significantly less expensive and easier to make than most high performance donor polymers.

FIGS. 6A-6D shows the current density-voltage curves, external quantum efficiency, normalized absorbance, and photoluminescence quenching of the best performing blends for each compound, respectively, with photovoltaic performance metrics listed in Table 1. At the optimized blend ratios and casting conditions, the emissions of both PDI molecules and PTB7 polymer were quenched, indicating compatible electronic energy levels for efficient channel I and channel II charge transfer processes. [64, 65] While the best performing devices achieve a high open-circuit voltage (Voc) of 1 V for the monomer and 0.9 V for the dimer compounds, the short-circuit current (Jsc) densities and fill factors have room for improvement. The atomic force microscopy (AFM) topographical images of the best performing blends (not illustrated) show grain sizes on the order of 100 nm for compounds (5) and (7b), and 200 nm for compound (7). PTB7:(7) films also exhibit much greater surface roughness than PTB7:(5) or PTB7:(7b). Thus, the performances of the devices of this example are believed to be morphology limited, underscoring the importance of selecting an appropriate donor and tailoring acceptors to achieve optimal phase segregation. Bay-linked PDI dimers annulated with S [36] and Se [3] atoms have been shown to form films with grain sizes on the order of 10-20 nm when blended with tailor-made high performance donor polymer PDBT-T1,66 achieving higher PCE.

Fabrication of Organic Solar Cells:

For the standard architecture devices (FIG. 5A), patterned indium tin oxide (ITO) coated glass substrates were coated with a thin layer of poly(3,4-ethylenedioxythiophene) polystyrene sulfonate (PEDOT:PSS). Light-absorbing blend solutions of PTB7:1, PTB7:2, and PTB7:3 were then spin-cast from chlorobenzene with 1,8-diiodooctane additive. N,N'-bis-(3-N,N-dimethylaminopropyl)perylene-3,4,9,10-tetracarboxylic diimide (PDIN) was deposited on top of the photoactive layer via spin-coating from methanol with 0.2% acetic acid. Finally, silver contacts were deposited via vacuum evaporation. For the inverted architecture devices (FIG. 5B), patterned indium tin oxide (ITO) coated glass substrates were coated with a thin layer of zinc oxide. Light-absorbing blend solutions of PTB7:5, PTB7:7, and PTB7:8 were spin-cast from chlorobenzene with 1,8-diiodooctane additive. Molybdenum (VI) oxide and silver were deposited via vacuum evaporation to complete the device.

Example 5: Organic Solar Cell Fabrication Use of Non-Halogenated Solvents

This example relates to preparation of organic solar cells with a PCE of about 4.8% which are based upon an active layer composed of the twisted PDI Acceptor (BAY-EP-N-Hex-CAG-PDI compound 7, also called tPDI-Hex) and a standard donor polymer, specifically PTB7-Th. PTB7-TH [69] is a high performance narrow band gap donor polymer that has been used in fabrication of fullerene 4-free OSC's. [37, 70, 71]

The devices can be fabricated and tested in air with 'as-cast' active layers being processed from the greener non-halogenated solvents (o-xylene or trimethyl benzene) or the eco-friendly and bio-derived solvent (2Me-THF) without loss in efficiency. These devices are fullerene-free devices. Additional details of this example are found in Dayneko, S. V. et al. 2016 [68] and the supplemental information for this reference available at the RSC (Royal Society of Chemistry, Publisher) web site for the Chem Comm journal. PTB7-Th and compound 7 have complimentary optical absorption profiles and electronic energy levels making them an ideal donor/acceptor BHJ pair. Related OSC devices exemplified in other examples herein have been fabricated employing chlorobenze or other halogenated solvents as the processing solvent and in an inert atmosphere. The energy levels for PTb7-Th range from −3.10 eV to −4.90 eV and those for compound 7 range from −3.80 eV to −6.0 eV.

PCEs of 4.8% are achieved for BHJ OSCs with an inverted structure (FIG. 5B) based on PTB7-Th: compound 7 blend films processed in air under ambient conditions from the halogen-free solvents 2-methyltetrahydrofuran (2Me-THF) or o-xylene (FIGS. 7A-D) without use of additives or

TABLE 1

Photovoltaic Performance Metrics of the Best Performing Blends of Each PDI Acceptor with the PTB7 Polymer and Twisted PDI Acceptors with PTB7-Th Polymer

| Donor: Acceptor | Blend ratio | Volatile Additive[a] (% v/v) | Voc (V) | $J_m$ (mA/cm$^2$) | PCE (%) | FF | |
|---|---|---|---|---|---|---|---|
| PTB7:5[b] | 40:60 | DIO (4) | 1.00 | 5.18 | 1.81 | 0.35 | avg[d] |
| | | | 1.00 | 5.49 | 1.93 | 0.35 | best |
| PTB7:7[b] | 50:50 | DIO (8) | 0.90 | 6.87 | 2.11 | 0.34 | avg |
| | | | 0.89 | 7.29 | 2.21 | 0.34 | best |
| PTB7:7b[b] | 50:50 | DIO (3) | 0.90 | 8.24 | 3.00 | 0.40 | avg |
| | | | 0.91 | 8.55 | 3.13 | 0.40 | best |
| PTB7-Th:7[b] | 50:50 | none | 0.90 | 11.64 | 4.96 | 0.47 | avg |
| | | | 0.89 | 11.82 | 3.13 | 0.49 | best |
| | | DIO (8) | 0.92 | 10.50 | 4.84 | 0.50 | avg |
| | | | 0.93 | 10.70 | 5.04 | 0.51 | best |
| PTB7-Th:7b[b] | 50:50 | none | 0.93 | 12.52 | 5.26 | 0.45 | avg |
| | | | 0.93 | 13.09 | 5.54 | 0.45 | best |
| | | DIO (3) | 0.92 | 12.23 | 5.20 | 0.48 | avg |
| | | | 0.93 | 12.63 | 5.43 | 0.47 | best |
| P3TEA:7b[b] | 40:60 | ODT (2.5) | 1.12 | 11.27 | 6.93 | 0.55 | avg |
| | | | 1.13 | 11.03 | 7.55 | 0.81 | best |

[a]DIO = 1,8-diiodooctane. ODT = 1,8-octanedithiol
[b]BHJ films processed from chlorobenzene (CB) and device architecture = ITO/ZnO/BHJ/MoO$_x$/Ag.
[c]BHJ films processed from trimethylbenzene (TMB) and device architecture = ITO/ZnO/BHJ/V$_2$O$_5$/Al.
[d]The reported average values are from 18 devices.

post-deposition treatments, such as thermal or solvent annealing or solvent treatments.

OSCs were fabricated with an inverted architecture (ITO/ZnO/PTB7-Th:compound 7/MoOx/Ag) owing to the ease of manufacturing and proven environmental stability. ZnO films were prepared by spin-casting a solution of the mixture of 2-methoxyethanol and ethanolamine on top of ITO and then sintering at 200° C. in air. The active layer was coated on top via spin-coating solutions containing the mixed PTB7-Th:compound 7 materials with a weight ratio of 2:3 or 3:7 and total concentration 10 mg/mL in air. A range of donor polymer of 20-60% by weight and 80%-40% by weight of acceptor is useful in such devices. More specifically, a weight range of donor polymer of 30-50% by weight and 70%-50% by weight of acceptor is useful in such devices. Film thickness was about 90 nm for all films as determined by atomic force microscopy (AFM). Film thicknesses of 75 to 100 nm, 80 to 95 nm or 85 to 90 nm are useful in such devices. A high acceptor loading is favoured owing to the relatively simpler (i.e. lower cost) synthetic procedure and the higher solubility of compound 7 compared to PTB7-Th. Finally, a MoOx/Ag top electrode for the device was applied by thermal deposition in vacuum.

Figure 7A:
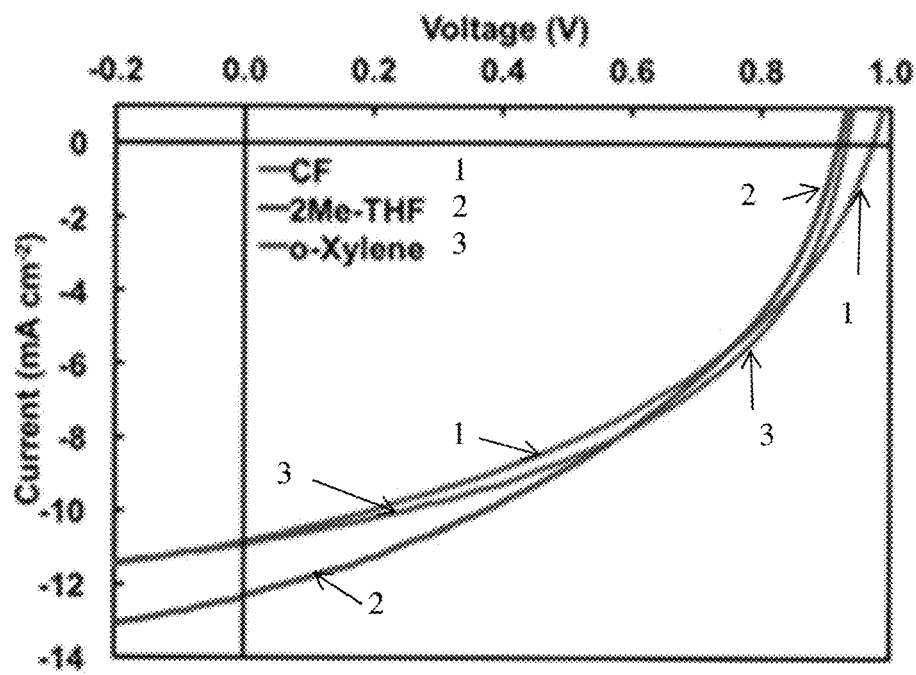
FIGS. 7A-7D show J-V characteristics (8A and 8C) and EQE spectra (7B and 7D) of OSCs with an inverted structure based on PTB7-Th:compound 7 blend films obtained from chloroform (CF) or halogen-free solvent (2Me-THF and o-xylene) at 2:3 (7A, 7B) and 3:7 (7C and 7D) donor: acceptor ratios.
Figure 7B:
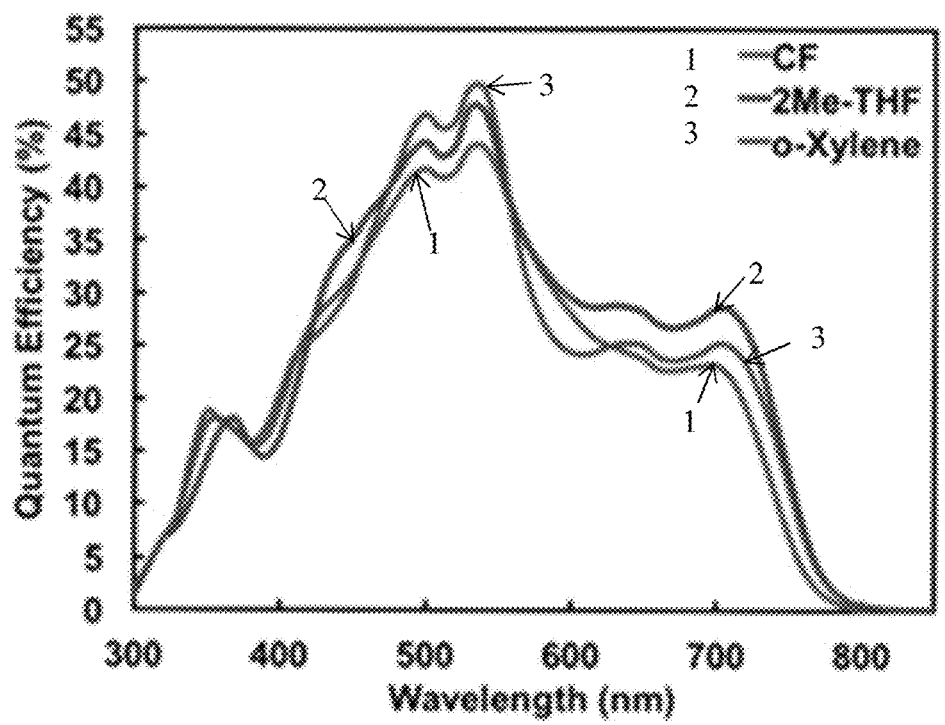
Figure 7C:
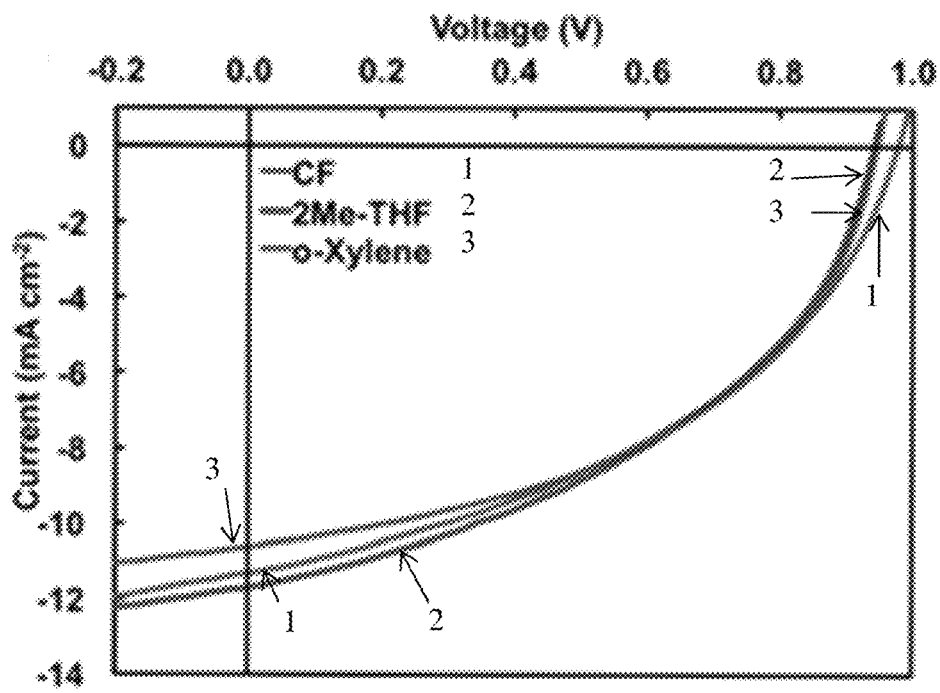
Figure 7D:
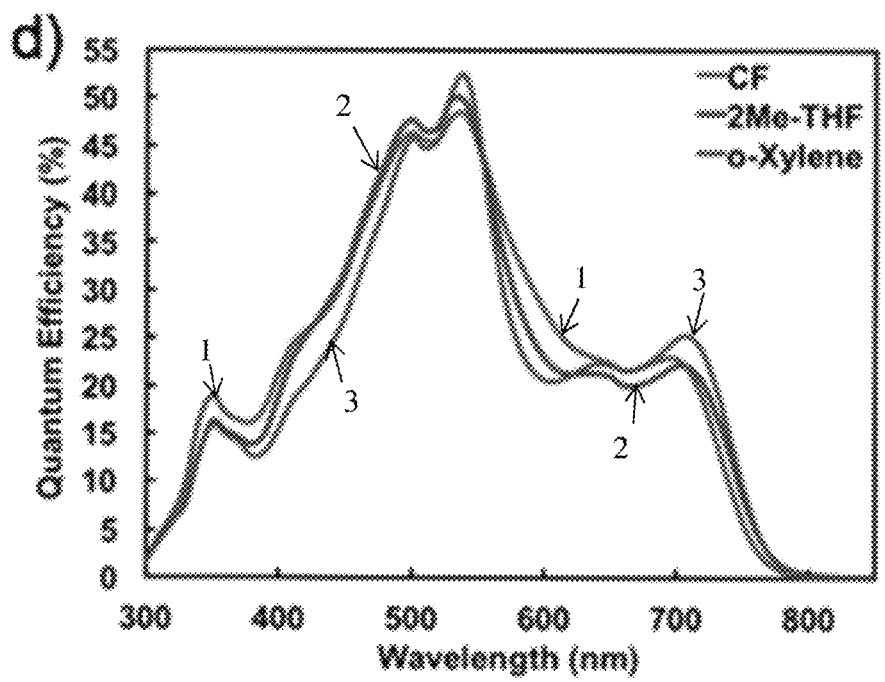
Figure 8A:
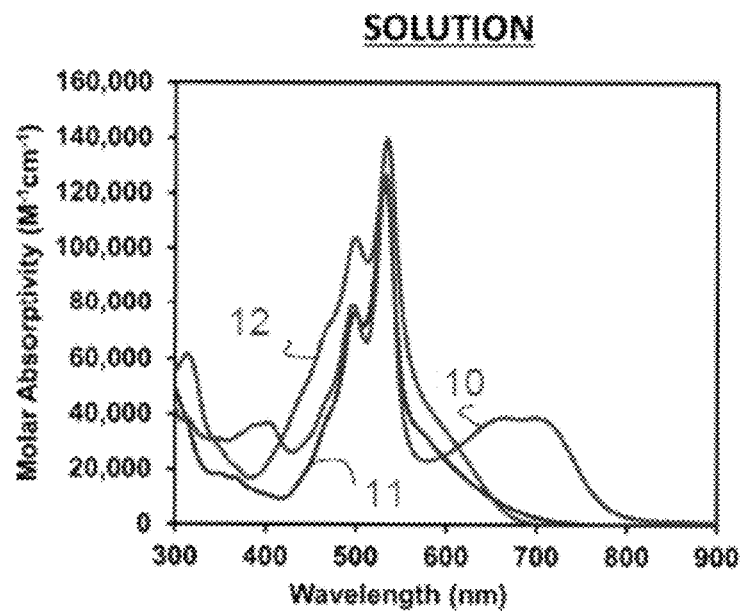
FIGS. 8A-8D illustrate and compare properties of compounds 10-12.
Figure 8B:
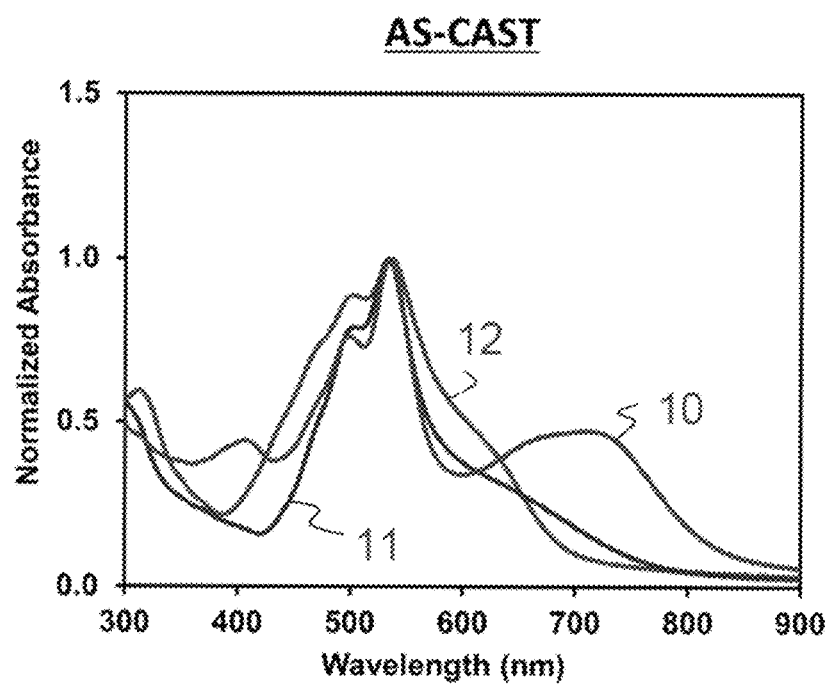
Figure 8C:
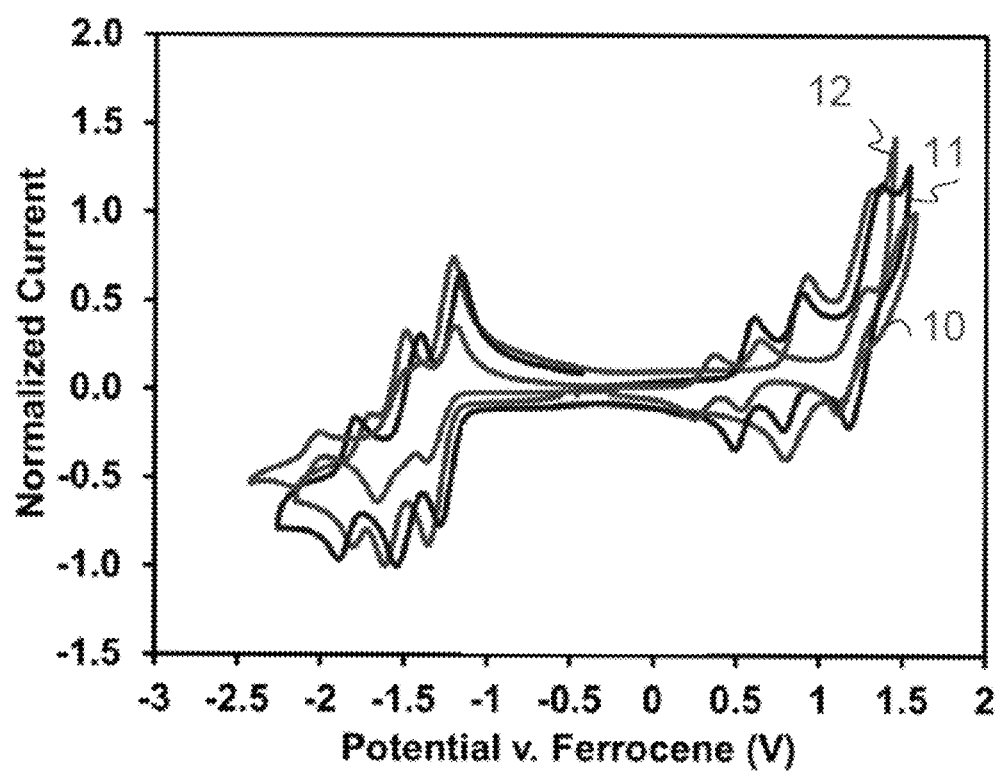
Figure 8D:
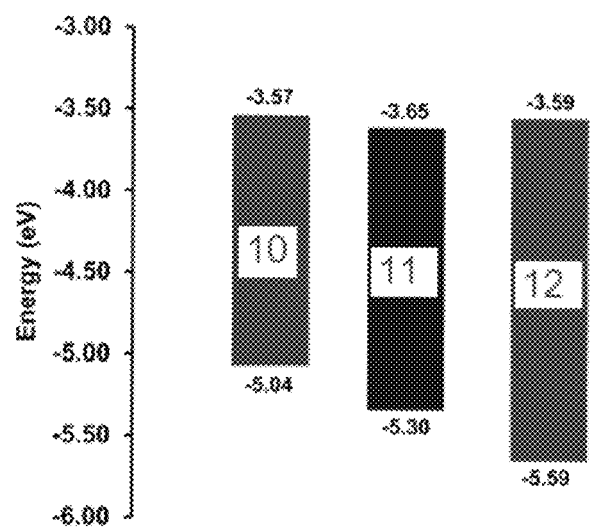

Current density-voltage (J-V) characteristics of OSCs measured under simulated AM 1.5 G irradiation with intensity of 100 mWcm$^{-2}$ are illustrated in FIGS. 7A and C at donor acceptor ratios of 2:3 and 3:7, respectively.

All EQE spectra have similar profiles with photocurrent generation being observed out to about 750 nm and all spectra having a pronounced maximum in the region from 450 to 500 nm. This maximum corresponds to the absorption of compound 7. The EQE spectra in the region from 600 to 750, which corresponds to contributions from the PTB7-Th, is lower in intensity owing to the lower concentration of PTB7-Th in the films.

Power conversion efficiencies for two weight rations of donor to acceptor and for different solvents used are listed in Table 2.

Table 2: Summary of device parameters of OSCs with an inverted structure based on PTB7-Th: compound 7 'as-cast' blend films obtained from neat CF, 2Me-THF, o-xylene, or TMB solvents at different donor/acceptor ratios under AM 1.5 G illumination at 100 mW cm$^{-2}$

TABLE 2

Summary of device parameters of OSCs with an inverted structure based on PTB7-Th: compound 7 'as-cast' blend films obtained from neat CF, 2Me-THF, o-xylene, or TMB solvents at different donor/acceptor ratios under AM 1.5G illumination at 100 mW cm$^{-2}$

| Solvent | PTB7-Th:tPDI-Hex [wt/wt] | $V_{oc}$ [V] | $J_{sc}$ [mA cm$^{-2}$] | PF [%] | PCE [%] |
|---|---|---|---|---|---|
| CF | 2:3 | 0.97 | 11.3 | 43.1 | 4.8 |
| CF | 3:7 | 0.98 | 10.3 | 43.1 | 4.4 |
| 2Me-THF | 2:3 | 0.92 | 12.3 | 41.2 | 4.7 |
| 2Me-THF | 3:7 | 0.94 | 11.6 | 43.7 | 4.8 |
| o-Xylene | 2:3 | 0.93 | 12 | 42.2 | 4.7 |
| o-Xylene | 3:7 | 0.95 | 10.7 | 47.6 | 4.8 |
| TMB | 3:7 | 0.95 | 10.8 | 44.6 | 4.6 |

Solar cells were fabricated on ITO-coated glass substrates, which were first cleaned by sequentially ultra-sonicating detergent and de-ionized water, acetone, and then isopropanol before use. ITO substrates were first pretreated UV-ozone for 30 minutes, then, ZnO precursor solution was spin-cast onto the ITO substrate at a speed of 4000 rpm and then annealed at 200° C. in air for 1 hour. Active layer solutions (PTB7-Th:tPDI-Hex weight ratios 2:3 or 3:7) were prepared in chloroform (CF), 2-methyl tetrahydrofuran (2Me-THF), o-Xylene, or 1,2,4-trimethylbenzene (TMB) without any additives. The total concentration of mixed PTB7-Th:compound 7 is 10 mg/mL was for CF, 2Me-THF, and o-Xylene solvents and 15 mg 10 mg mL for TMB. For CF, 2Me-THF, and TMB solvents, the films giving best device PCE were spincoated at room temperature at 1500 rpm in air. Active layers from o-Xylene with best device PCE were spin-coated at 600 rpm. The substrates were then kept in an N$_2$ atmosphere glovebox overnight before evaporating MoOx and Ag. The evaporation of 10 nm of MoOx followed by 100 nm of Ag were thermally deposited under vacuum (4×10$^{-6}$ Torr). Current density-voltage (JV) characteristics were measured using a Keithley 2420 Source Measure Unit. Solar cell performance used an Air Mass 1.5 Global (AM 1.5 G) Solar Simulator (Newport, Model 92251A1000) with an irradiation intensity of 100 mW cm$^{-2}$, which was measured by a calibrated silicon solar cell and a readout meter (Newport, Model 91150V). EQE spectra were measured by using a QEX7 Solar Cell Spectral Response/QE/IPCE Measurement System (PV Measurement, Model QEX7) with an optical lens to focus the light into an area about 0.04 cm$^2$, smaller than the dot cell. The silicon photodiode was used for calibration of the EQE measurement system in the wavelength range from 300 to 1100 nm.

Example 6: Synthesis of A-D-A Molecules

This example relates to incorporating high-performance PDI materials of this disclosure as the terminal units in a A-D-A framework. A generic exemplary A-D-A molecule is illustrated as:

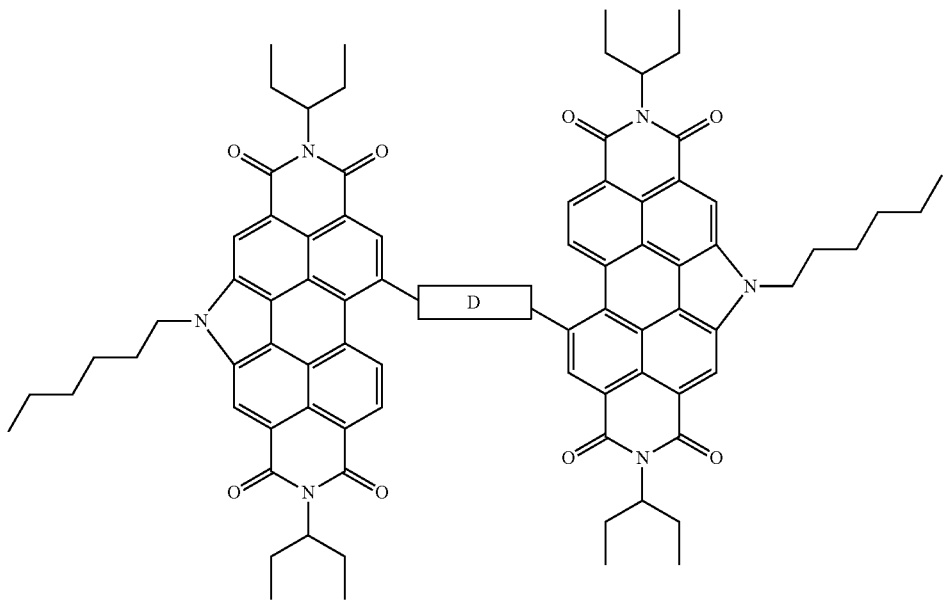

It will be appreciated that alkyl substituents at the imide nitrogens and at the bay nitrogen can be varied as described above.

These materials are an extension of "twisted PDI" design with several added advantages. In one aspect by incorporating dye-based materials as the molecular core (D), the resultant molecules will exhibit low-energy wavelength absorption that is not possible with only PDI units (Ionset=580 nm). Additionally these D cores are considered to be electron donating with respect to the PDI units where a localized HOMO on the core and a LUMO on the PDI units are of interest for the investigation of their use as single-component materials.

A. Exemplary Compounds 10-12:

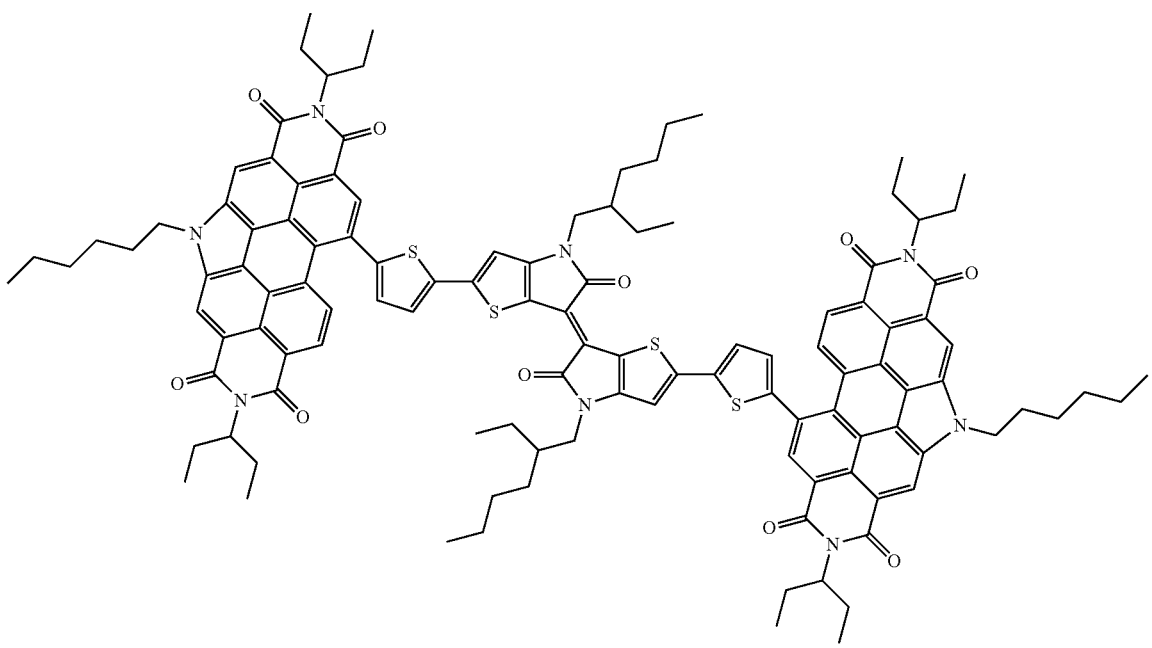

10

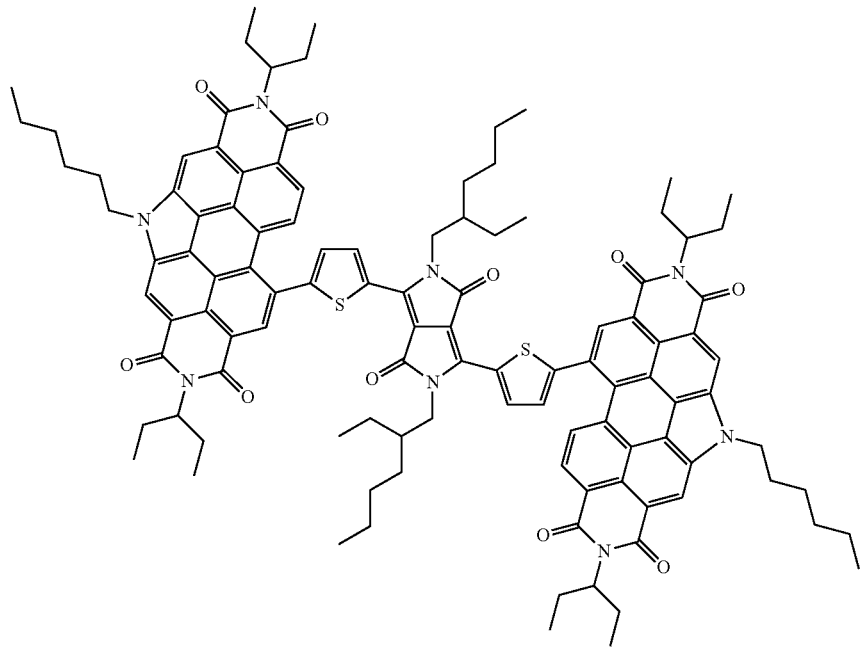
11
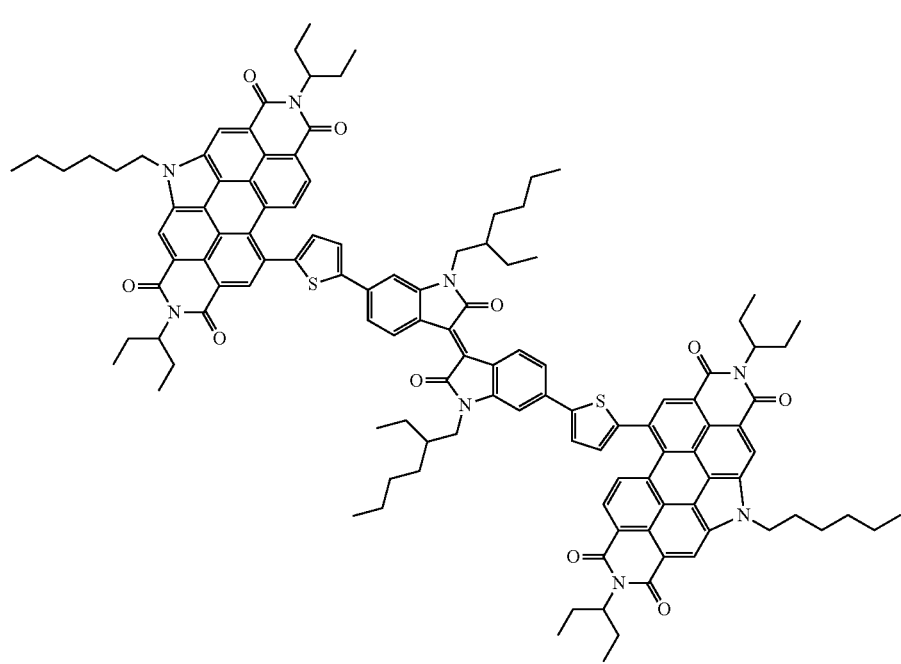
12

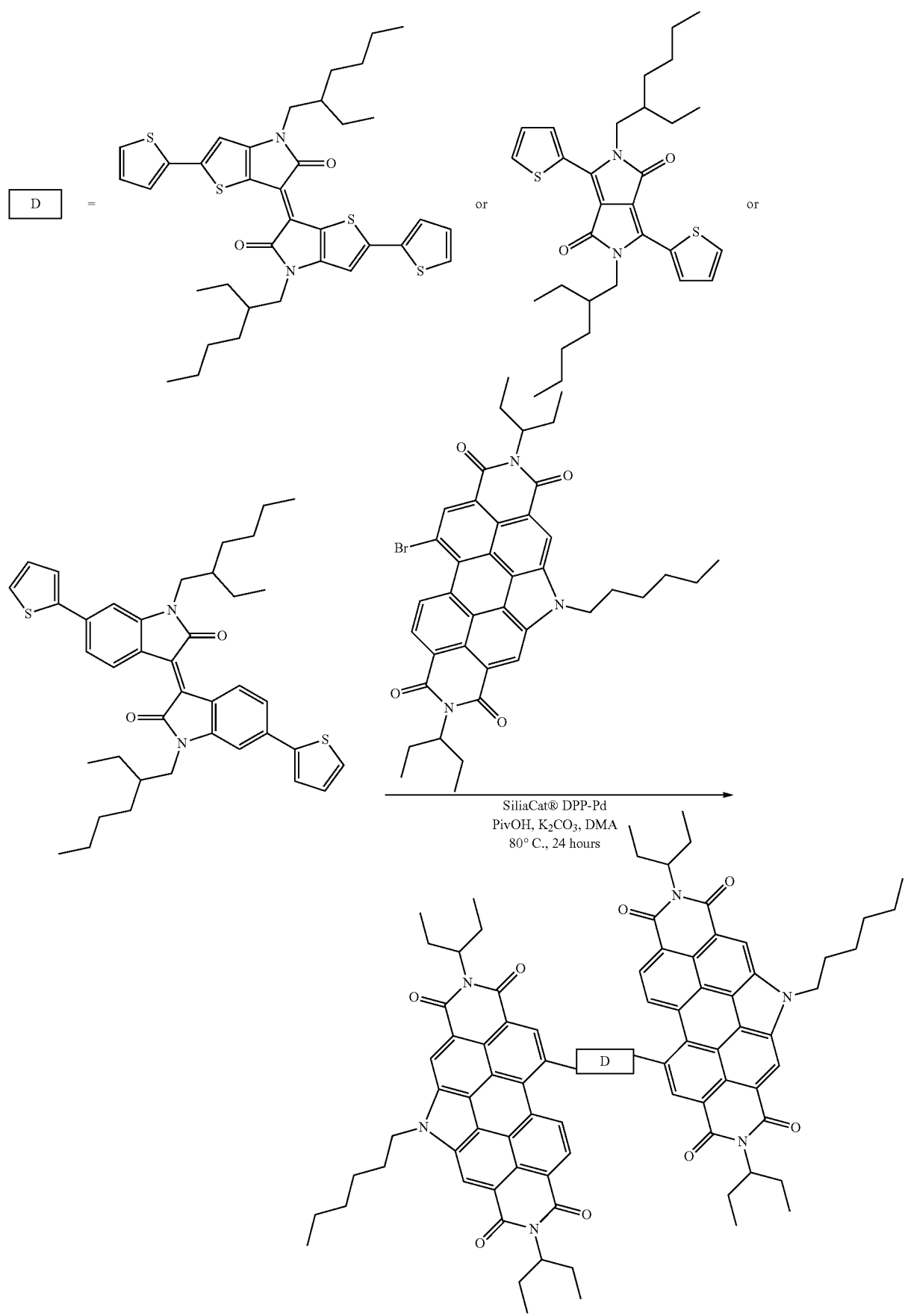

General Synthesis of Compounds 10-12

Molecular core (D) (1 eq.), Compound (6) (2.2 eq.), Silia Cat® DPP-Pd (5 mol %), pivalic acid (30 mol %), and potassium carbonate (2.5 eq.) were added to a pressure sealed glass vial with a magnetic stir bar. The vial was sealed with a septa crimp cap and the contents were purged with $N_2$ gas before N,N'-dimethylacetamide (1 mL for every 30 mg of D) was added via syringe through the septa. The contents were set to stir at 80° C. for 24 hours. Upon completion the contents were poured into 100 mL of methanol and allowed to stir for several hours. The precipitated solid was filtered off and the filtrate discarded. The collected solid was dissolved in dichloromethane to isolate from the silica-supported catalyst. The filtrate was collected and concentrated on a rotary evaporator to dryness. The product was purified by flash column chromatography eluting impurities using hexanes to dichloromethane as the gradient. The product elutes at 100% dichloromethane with 5% trimethylamine. The product fraction was collected and concentrated to dryness on a rotary evaporator. The solid product was stirred in acetone to remove polar impurities that elute with trimethylamine. The final purified product was collected by filtration as a solid from acetone.

Characterization and comparison of compounds 9-12 is illustrated in FIGS. 8A-8D.

B. Synthesis and Application of Exemplary Compound 13 annealing leading to a near 3-fold increase in PCE. This result is among the best reported utilizing DPP-based acceptors in air-processed and tested OSCs. All solar cells exhibited good air and light stability over a 35-day evaluation period. Additional details of this example can be found in McAfee et al. 2017 [67] and the supplemental information for this reference which is available on-line at the journal web site. This reference is incorporated by reference herein in its entirety for details of synthesis of compound 13 and its properties and also for methods of preparing OSCs using this material and in particular for SVA methods applied to this material and devices made using this material.

A strategy in the design of high-efficiency PDI-based nonfullerene acceptors has been to link two or more PDI monomers together, forming nonplanar multichromophoric molecular structures to tailor self-assembly. [17, 78, 2, 73, 37] In surveying high-performance PDI-based nonfullerene acceptors of this design, it was noticed that very few respond favorably to postdeposition solvent vapor annealing (SVA). [74, 75, 76] SVA has been a powerful tool for increasing device efficiencies through induced morphological changes in the active layer blend. Utilizing the PDI-D-PDI design strategy, illustrated in Formulas III and IV, the organic dye diketopyrrolopyrrole (DPP) was selected as the linker (D) between two PDI units. DPP has been known to exhibit a favorable response to SVA conditions. Incorporating this

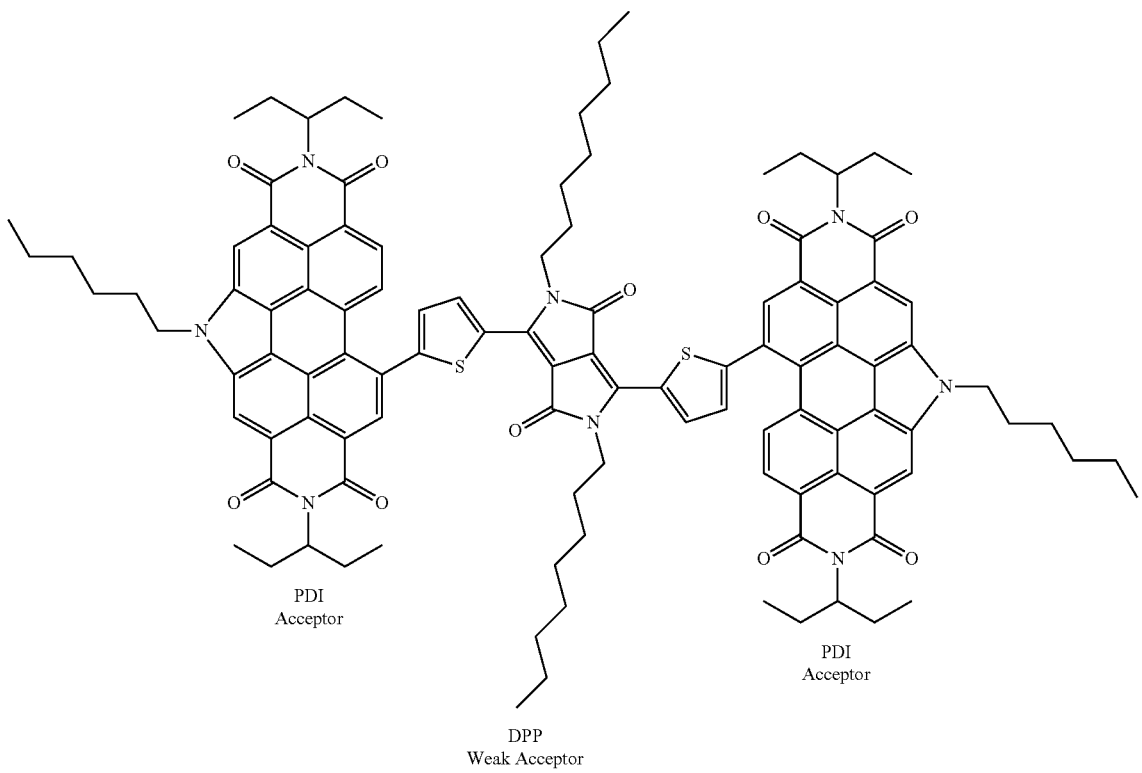

13

PDI Acceptor

PDI Acceptor

DPP Weak Acceptor

60

In this example, a perylene diimide (PDI) flanked diketopyrrolopyrrole (DPP) π-conjugated small molecule (13) is synthesized. When acceptor 13 is paired with the donor polymer PTB7-Th, air-processed and tested, bulk-heterojunction (BHJ) organic solar cells achieve a high power conversion efficiency (PCE) of 5.6%. Acceptor 13 showed favorable morphological changes upon solvent vapor electron-deficient dye as the central unit creates a unique acceptor-based push-pull system with an A-A'-A framework. Rarely have PDI units been linked via electron deficient units; however, this strategy ensures the final material will have suitable energy levels for use as an electron acceptor in BHJ solar cells.

Functionalization to the bay-position of PDI in the form of an N-annulation is described herein above. By annulating one side of the PDI chromophore, the monobromination of PDI is straightforward, allowing for a facile synthesis of PDI materials for use as the terminal acceptor in molecular frameworks.

Using direct heteroarylation and employing a silica-supported catalyst, compound 13, also designated PDI-DPP-PDI is successfully synthesized in 70% yield (0.46 g). The final material was initially purified by a standard column chromatography procedure; however, the importance of purity for 7-conjugated materials to be tested in electronic devices was recognized, so a more rigorous purification was also conducted. Using recycling HPLC. This allowed removal of an impurity (ca. 0.03%) identified as residual monosubstitution. The synthesis of compound 13 from two low-cost building blocks through a simple and sustainable synthetic route is a significant achievement in the development of nonfullerene acceptors.

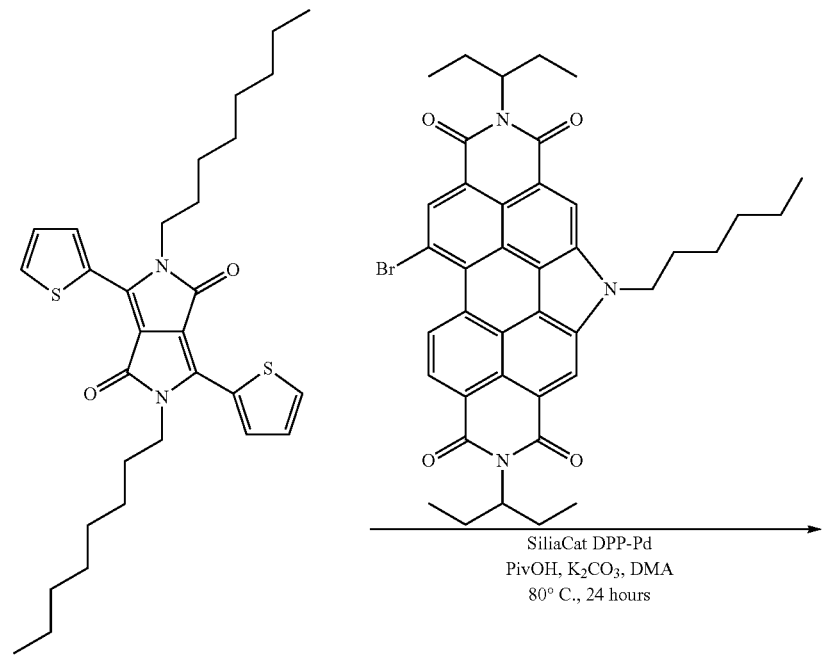

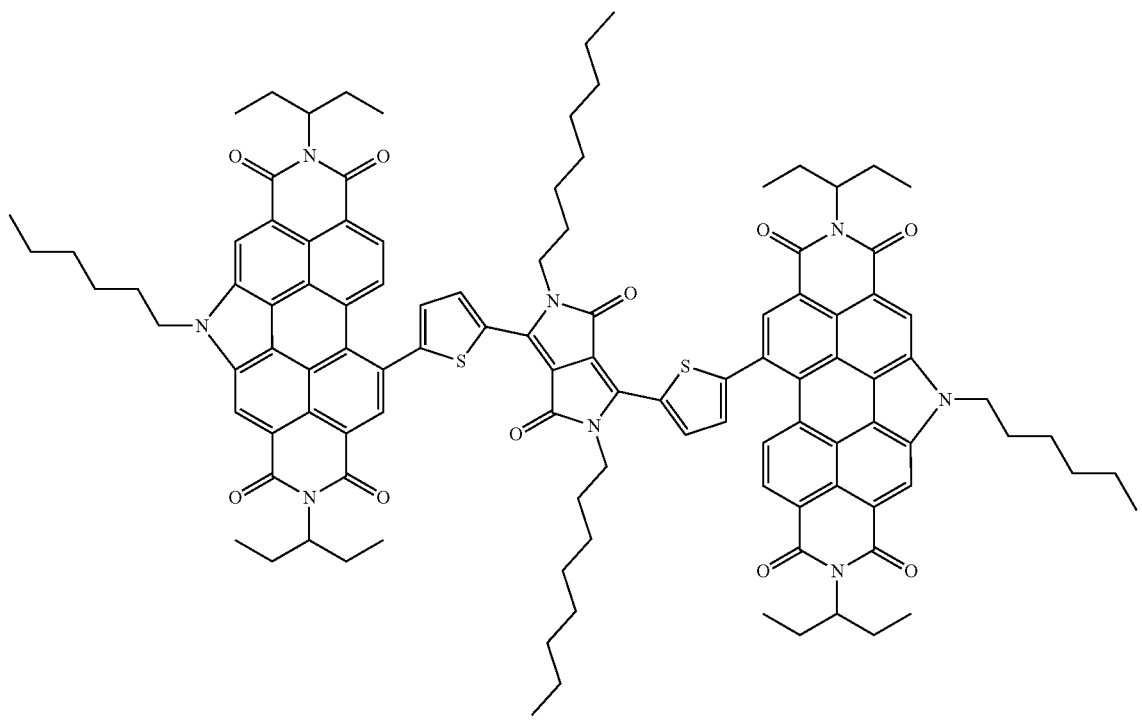

Diketopyrrolopyrrole precursors were synthesized according to a literature procedure. [77] The synthesis of N-annulated perylene diimide precursor materials is described herein above.

Synthesis of Compound 13:

In a 12-15 mL pressure vial 2,5-bis(1-octyl)-3,6-di(thiophen-2-yl)diketopyrrolopyrrole (0.20 g, 0.38 mmol, 1 eq.), 11-bromo-5-hexyl-2,8-bis(1-ethylpropyl)perylene diimide (0.59 g, 0.84 mmol, 2.2 eq.), SiliaCat® DPP-Pd (0.08 g, 5 mol %), pivalic acid (0.02 g, 30 mol %) and potassium carbonate (0.14 g, 0.98 mmol, 2.5 eq.) were added with a stir bar and sealed with a crimp sealed septa cap. The contents were purged with $N_2$ gas followed by the addition of degassed anhydrous N,N'-dimethylacetamide (7 mL) via syringe. The reaction mixture was heated at 80° C. in a LabArmor® beads bath for 24 hours. After 24 hours the reaction mixture was poured into MeOH and allowed to stir overnight. The precipitated product was collected by filtration and the filtrate was discarded. The solid product was subsequently washed with dichloromethane to solubilize the product and isolate it from the insoluble silica supported catalyst. The filtrate was concentrated by rotary evaporation and prepared for purification by flash column chromatography. With a petroleum ether to dichloromethane gradient residual impurities and a small fraction of mono-substituted product can be removed from 50-90% dichloromethane. The product begins to elute slowly at 100% dichloromethane and was more rapidly eluted following the addition of 5% triethylamine. The product fractions were slurried with a small amount of aluminum oxide and filtered. The filtrate was concentrated by rotary evaporation to a solid which was stirred in acetone overnight to remove residual polar impurities that eluted upon the use of triethylamine. The final product was collected by filtration as a red-brown solid (0.46 g, 0.26 mmol, 70% yield). Melting point 389° C. HRMS (MALDI): m/z: 1774.8 calc'd: 1775.8

$^1$H NMR: 9.38 (d, JH-H=4 Hz, 2H); 9.13 (s, 2H); 9.07 (s, 2H); 8.90 (s, 2H); 8.62 (s, 2H); 8.34 (d, JH-H=8 Hz, 2H); 7.65 (d, JH-H=4 Hz, 2H); 5.25-5.20 (m, 4H); 4.96 (t, 4H); 4.16 (t, 4H); 2.37 (m, 8H); 2.25 (m, 4H); 2.00 (m, 8H); 1.86 (m, 4H); 1.49 (m, 4H); 1.40 (m, 8H); 1.31 (m, 8H); 1.19 (m, 4H); 1.11 (m, 8H); 1.00 (t, ov, 12H); 0.96 (t, ov, 12H); 0.88 (t, ov, 6H); 0.70 (t, 6H).

Optoelectronic Characterization

Characterization was completed by cyclic voltammetry (CV) and UV-visible and spectroscopy (UV-vis). A summary of optical and electrochemical data can be found in Table 3.

TABLE 3

Optical and Electrochemical Data for Compound 13:

| | |
|---|---|
| soln $\eta_{max}$ (nm)$^a$ | 538 |
| soln $\eta_{onset}$ (nm)$^a$ | 685 |
| film $\eta_{max}$ (nm)$^b$ | 538 |
| film $\eta_{onset}$ (nm)$^b$ | 760– |
| ε(M-1cm-1)$^c$ | 121 352 |
| Ox$_{onset}$ (V)$_d$ | 0.50 |
| Red$_{onset}$ (V)$_d$ | −1.14 |
| oxidation potentials (V)$^d$ | 0.50, 0.85, 1.26 |
| reduction potentials (V)$^d$ | −1.14, −1.49, −1.85 |
| IP (eV)$^e$ | 5.3 |
| EA (eV)$^f$ | 3.7 |

$^a$1.0 w/v % solution in CHCl$_3$.
$^b$1.0 w/v % solution in CHCl$_3$ cast at 1500 rpm.
$^c$1.0 w/v % solution in CHCl$_3$ measured at 538 nm.
$^d$Estimated potentials from solution cyclic voltammetry.
$^e$IP = (Oxonset + 4.80).
$^f$EA = (Redonset + 4.80).

Thin-films were subject to post-deposition thermal and solvent vapor annealing in an attempt to influence the solid state self-assembly of the material. Unlike other high performance DPP-based materials, thermal annealing at a range of temperatures from 100 to 200° C. was shown to have no observable effect on the thin-film morphology by UV-vis. SVA was carried out using a range of solvents (including, THF, $CH_2Cl_2$, $CHCl_3$, $CS_2$, acetone, ethylacetate, diethyl ether and toluene.) with $CHCl_3$ appearing to induce the most significant change in the UV-vis profile. $CHCl_3$ SVA leads to a 75 nm blue-shift in the $\lambda_{onset}$ with a loss of the broad low-energy shoulder (686 nm) and the appearance of a sharper one (586 nm), likely a result of reorganization dictated by the DPP chromophore. The emergence of this low-energy peak upon SVA has been previously observed in DPP-based small molecules. Thin-film photoluminescence was also influenced by $CHCl_3$ SVA, where a doubling in the intensity was observed in comparison to that of the as-cast thin-film.

Device Performance

Analysis of the influence of postdeposition SVA was first investigated by space charge limited current (SCLC) measurements in the following device configuration: ITO/DPP-PDIDPP (compound 13)/LiF/Al. Upon $CHCl_3$ SVA, a 7-fold increase in electron mobility was observed compared to the as-cast device. This increase in mobility suggests a preferential reordering of the material in the solid state for rapid charge transport, which would also prove to be crucial for improving as-cast photovoltaic device efficiencies. Powder X-ray diffraction (PXRD) measurements of the thin-films show no diffraction peaks upon SVA of the as-cast thin-film, indicating that any changes in crystalline nature of thin-film nanostructure are minor and not observable by our instrument.

The photovoltaic performance of PDI-DPP-PDI (compound 13) was obtained from the following inverted device architecture: ITO/ZnO/BHJ/MoOx/Ag. In the assessment of the photovoltaic performance of new nonfullerene acceptors, the donor selection continues to be a complicated issue. Currently, a wide range of donor materials are being used, complicating the comparison of nonfullerene acceptors and their design principles. However, P3HT [64] is the most popular wide band gap polymeric donor and PTB7-Th [65] is the most popular narrow band gap polymeric donor. Considering the absorption of PDI-DPP-PDI in the higher energy region of the visible spectrum, PTB7-Th was selected as the donor component in the BHJ.

The PTB7-Th:PDI-DPP-PDI active layer blend offers a suitable energy level offset as determined by solution CV with complementary absorption profiles. PTB7-Th contributes an absorption profile from 300 to 800 nm with Amax at 720 nm, while PDI-DPP-PDI is able to fill in the regions of low PTB7-Th absorption from 450 to 600 nm, leading to a panchromatic absorption in the entire visible region (400 to 800 nm, FIG. 4c,d). PDI-DPP-PDI also exhibited emission quenching of PTB7-Th, further highlighting the acceptable pairing of the two active layer materials.

The active layer was processed under simple and repeatable conditions. Using $CHC_{l3}$ as the processing solvent, the active layer materials were dissolved with a total concentration of 10 mg/mL and processed in air at room temperature. Spin-casting the films at 1500 rpm gave the best results. The best donor:acceptor ratio was found to be 40:60, yet acceptor heavy devices 30:70 and 20:80 still gave appreciable device performance. Donor amounts in a device can range from 20-60 wt % with acceptor amounts ranging from 80-40 wt %. More specifically, donor amounts in a device can range from 30-50 wt % with acceptor ranging from 70-50 wt %. The devices with greater PDI-DPP-PDI content maintained high open-circuit voltages (VOC) but led to lower fill factors (FF) and short-circuit currents (JSC). These losses in performance can be correlated to the limited PTB7-Th content, which is supported by the UV-vis spectra where limited contribution from PTB7-Th is observed. The CHCl$_3$ SVA of the devices was found to reach their best efficiencies after 2-5 min, where longer times (10 min) met performance metrics similar to the as-cast devices. It is detrimental to device performance for the CHCl$_3$ SVA to reach 10 min. A range of CHCl$_3$ SVA from 2 to less than 10 min can be applied. More preferably, a range of CHCl$_3$ SVA from 2 to 8 min can be used or a range from 2 to 5 min can be used.

Figure 9A:
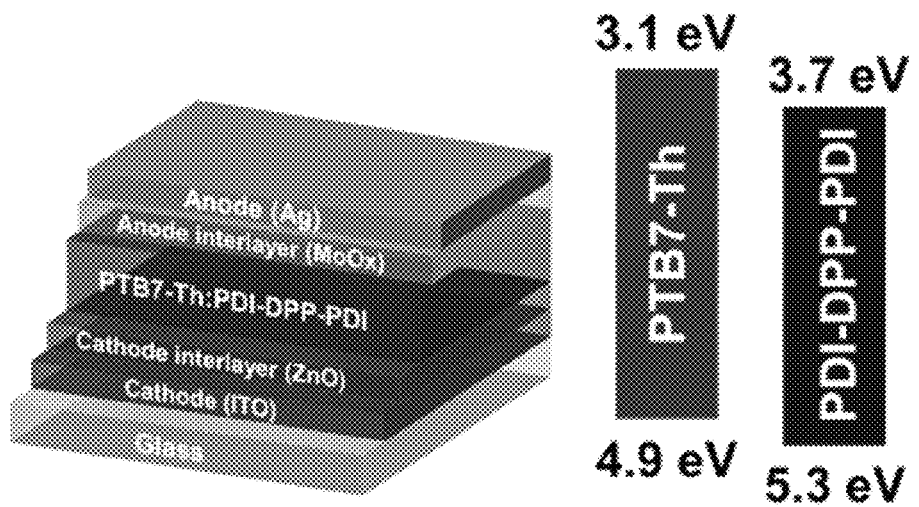
FIGS. 9A-9D illustrate device performance using compound 13.
Figure 9B:
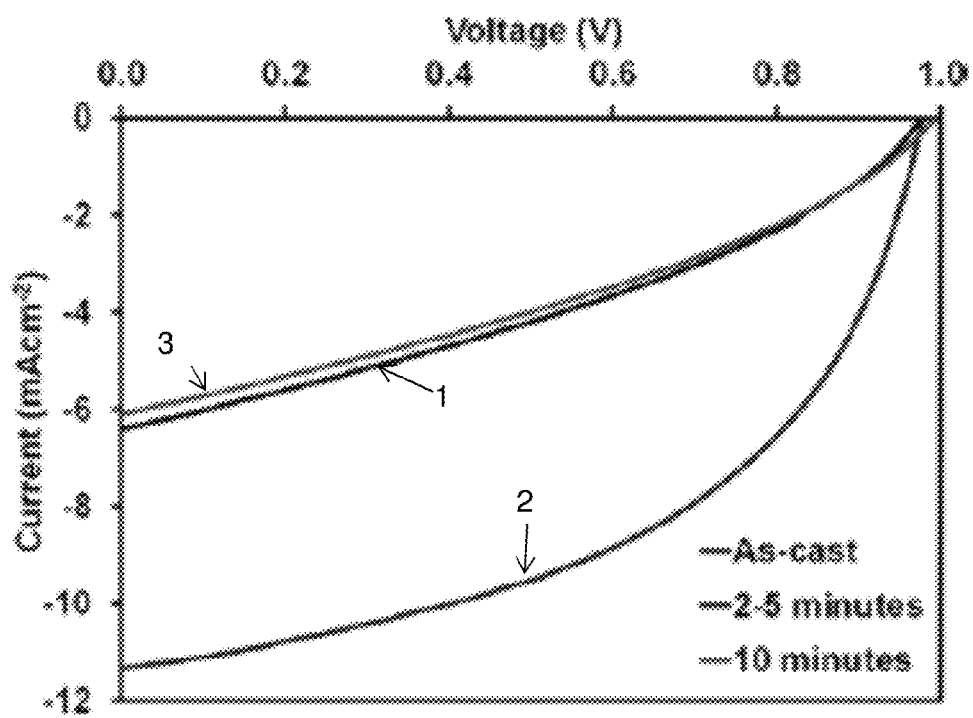
Figure 9C:
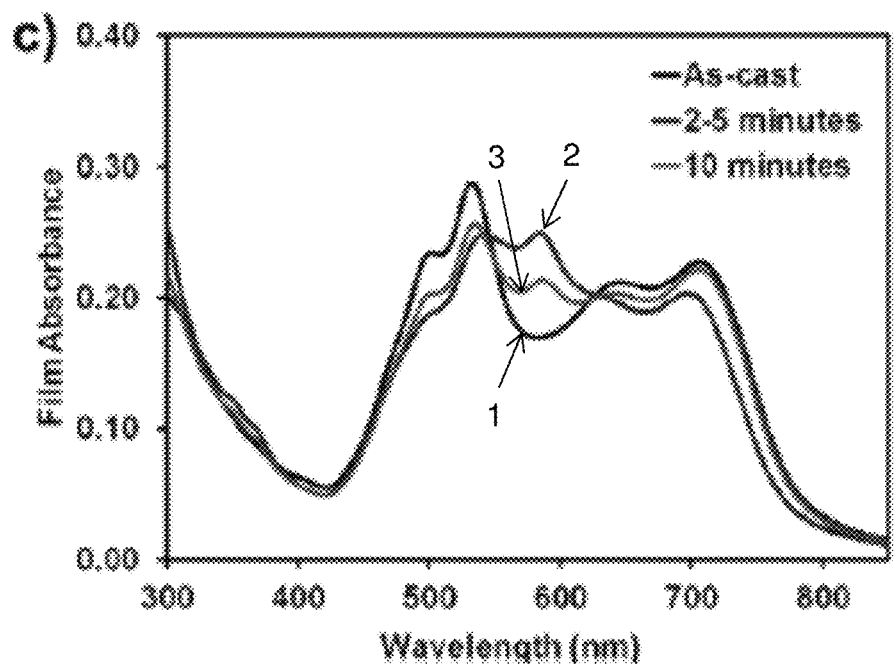
Figure 9D:
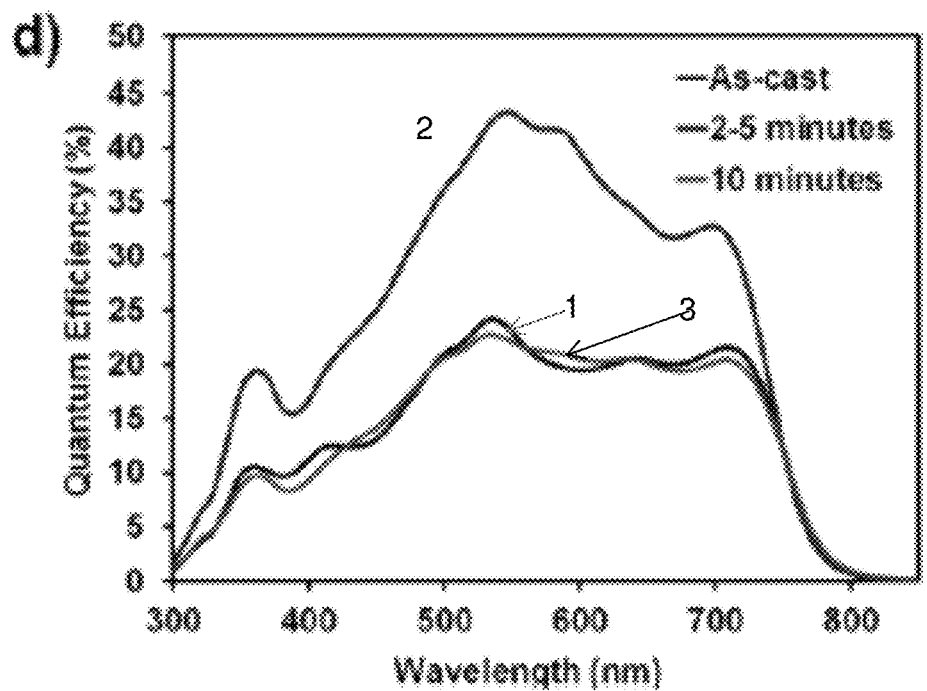

Analysis of the UV-vis profile of the active layer blend under these different CHCl$_3$ SVA times has highlighted a change in the profile at 586 nm (FIG. 9C). The emergence of the new peak in this region is linked to the CHCl$_3$ SVA conditions that reached the highest device efficiencies. A comparison of the external quantum efficiency (EQE) profiles (FIG. 9D) of the as-cast and solvent vapor annealed devices has provided further evidence to support the importance of this distinct change in the active layer absorption profile. Accompanying the emergence of the peak at 586 nm is a 2-fold increase in the photocurrent generation where PDI-DPP-PDI absorbs (450-600 nm) compared to that of PTB7-Th (650-750 nm). This indicates that the peak observed at 586 nm upon SVA can be directly correlated to a more favorable BHJ where PDI-DPP-PDI is significantly contributing to photocurrent generation.

Preliminary device stability was probed by leaving devices exposed to air and ambient light for a period of 35 days. For the first 7 days, there were no PCE changes. After 14 days, a ~10% decrease in PCE was observed, while after 35 days only a ~30% decrease in PCE was observed. Overall, the performance decreased from ~5.0% to 3.5% after 35 days. This loss in efficiency can be attributed to degradation of the Ag contacts considering the UV-vis and EQE spectra remain consistent, suggesting that the active layer is maintaining its integrity. All things considered, these organic solar cells proved to be quite stable and are suitable for further stability and lifetime measurements.

Compound 13 exhibited favorable optical, electronic, and self-assembly properties for use as an active layer material in OSCs. OSC devices were fabricated in a straightforward method, processed in air at room temperature, and reached PCEs of 5.6%. This performance is among the highest reported to date for DPP-based acceptor OSCs and is among the best reported for fullerene-free OSCs fabricated and tested in air, a feature that is important for the simplified industrial manufacturing of the OSC technology.

Example 7: Synthesis of Compound PDIACPDI (15) and Compound PDIACACPDI (17)-Alkynylene Bridged PDI

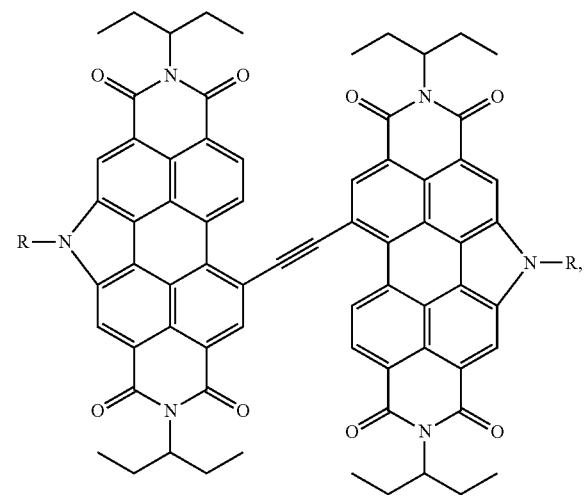

where each R independently is a straight-chain or branched C1-C30 alkyl group.

Compound 15 can be prepared by a conventional synthetic method:

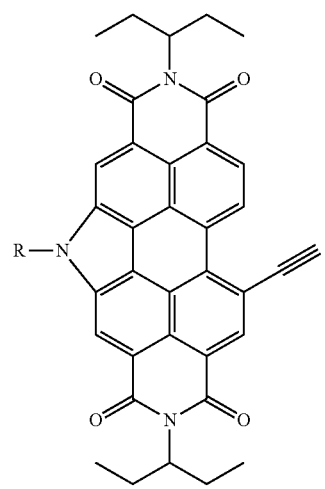

PDIAC(14)

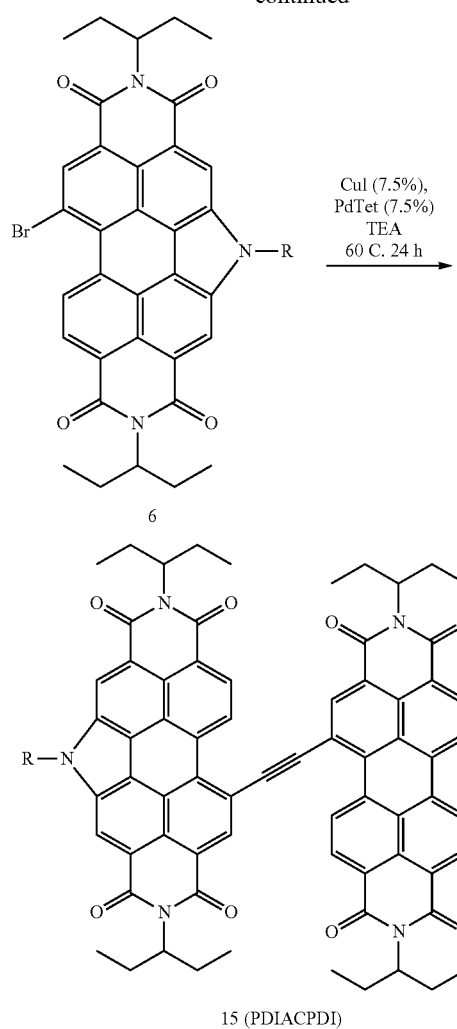

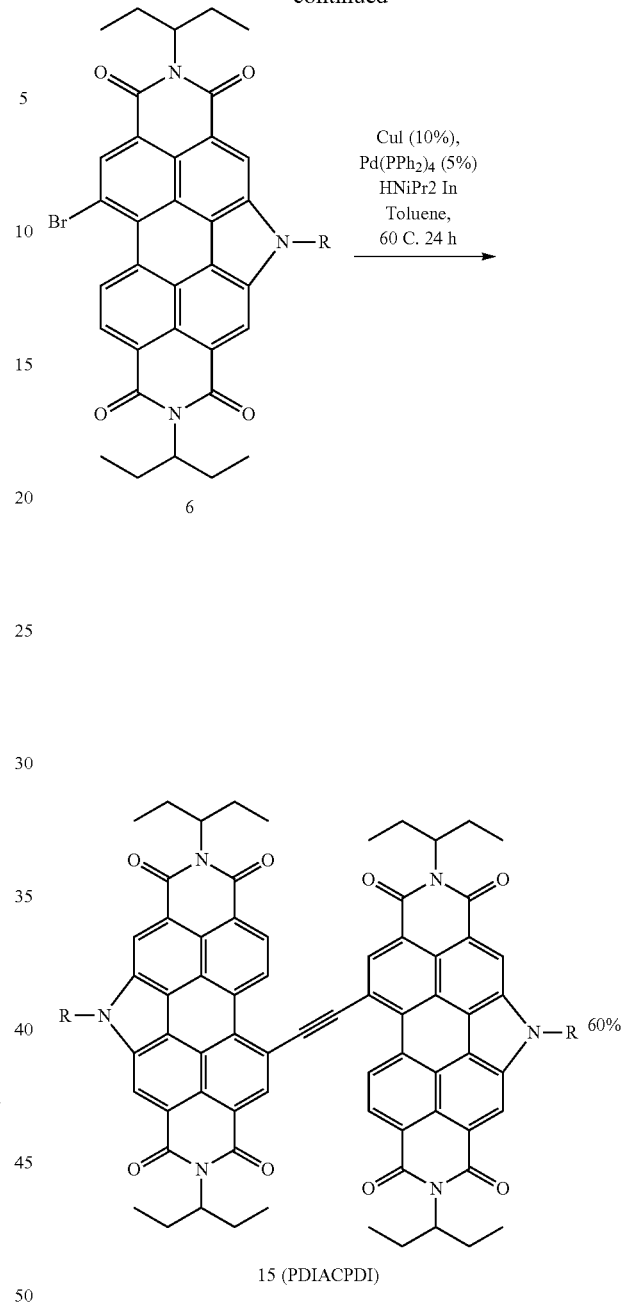

Alternatively, compound 15 can be synthesized using an improved synthetic method as shown in Scheme 2:

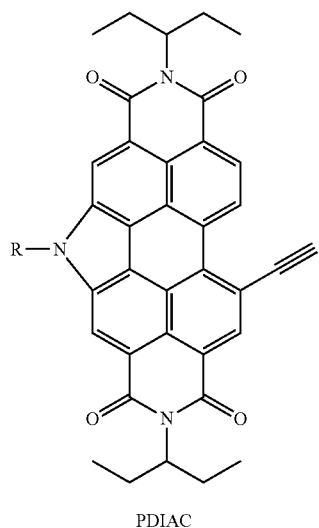

PDIAC

To a 20 mL microwave vial was added PDIAC (202 mg, 0.311 mmol), PDI-Br (6) (200 mg, 0.28 mmol), Pd(PPh$_3$)$_4$ (16 mg, 0.014 mmol) and CuI (5 mg 0.028 mmol). The vial was capped and purged with nitrogen gas for 15 minutes. To the sealed vial was added 10 mL recently sparged toluene and 1 mL dry diisopropylamine. The reaction mixture was heated to 60° C. for 1 hour, until thin layer chromatography indicated completion. The purple solution was diluted with DCM and filtered through a 1 cm thick pad of celite to remove metal catalysts. The solvent was removed from filtrate under reduced pressure to give PDIACPDI (15) as a purple solid which was isolated from acetone (350 mg, 0.31 mmol, 98%). To ensure minimal metal contamination and neutralize any acidic sites PDIACPDI was dissolved in DCM and slurried with celite for 30 min before filtering through alumina.

Synthesis of Compound PDIACACPDI (17)

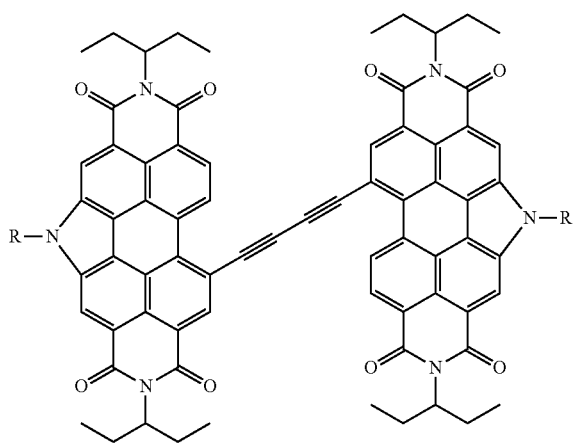

Intermediate 16 is prepared from starting material 6 as shown in Scheme 3:

It will be appreciated that alkyl groups on the compounds of Scheme 3 can be varied by selection of starting materials.

In more detail, PDI-Br (6) (1 g, 1.4 mmol), CuI (8 mg, 0.04 mmol), and Pd(PPh$_3$)$_4$ (45 mg, 0.04 mmol) were added to a 20 mL microwave vial. The vial was sealed and purged with nitrogen for 5 minutes. To this mixture was added 20 mL of diisopropylamine and TMS-acetylene (0.4 mL, 2.8 mmol). The reaction was stirred and heated to 40° C. for 24 h. The reaction was then diluted with 50 mL THF and, using 20 mL more THF, filtered through 1 cm silica. The red solution was concentrated under reduced pressure to give a red solid. The solid was dissolved in 50 mL DCM and 0.5 g SiliaMetS® Dimercaptotriazine was added. This mixture was stirred for 4 h at room temperature before filtering over 1 cm Celite to remove the scavenger. To the filtrate was added 10 mL methanol and the solvent was removed under reduced pressure to give (1 g, 1.37 mmol, 98%) as a dark purple powder which was isolated from methanol.

To a 250 ml round bottom flask containing PDIACTMS (1.9 g, 2.5 mmol) and potassium carbonate was added 100 mL each of chloroform and methanol. The resulting mixture was stirred for 10 minutes before filtering through silica with additional dichloromethane to remove the residual potassium carbonate. The solvent was removed from the red filtrate under reduced pressure. The purple solid was isolated from methanol to give compound 16 PDIAC (1.707 g, 2.5 mmol, 100%). No further purification was necessary.

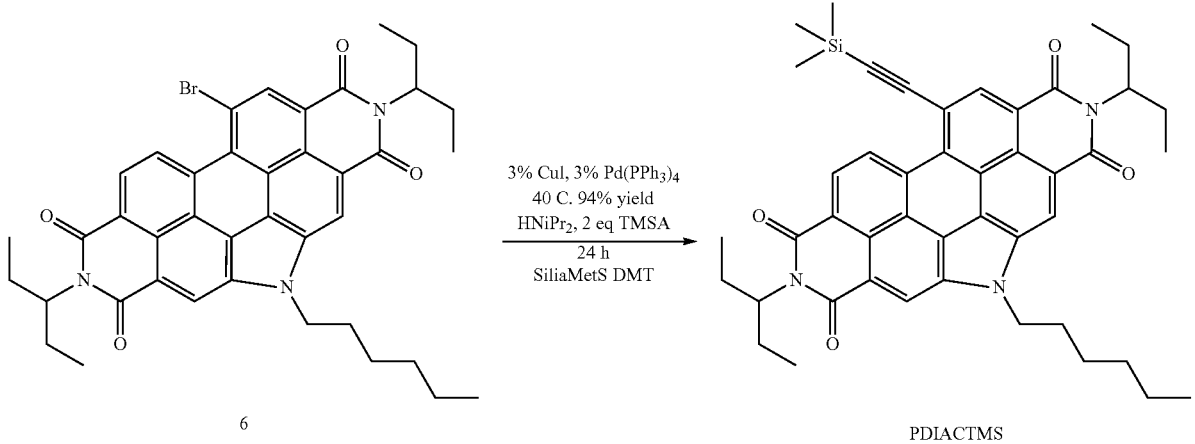

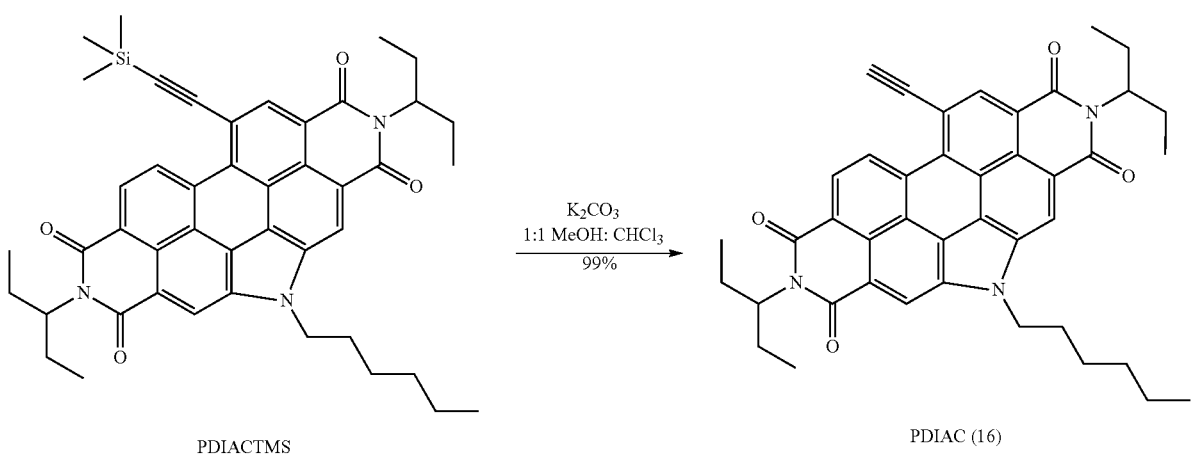

Compound 17 can be prepared from compound 16 using a conventional method:
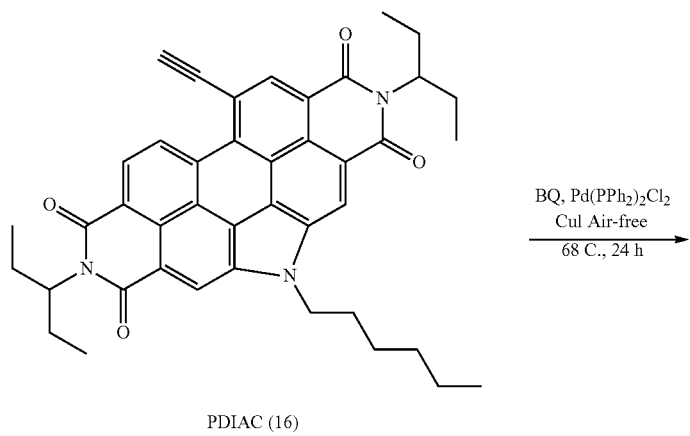
PDIAC (16)
BQ, Pd(PPh₂)₂Cl₂
CuI Air-free
68 C., 24 h
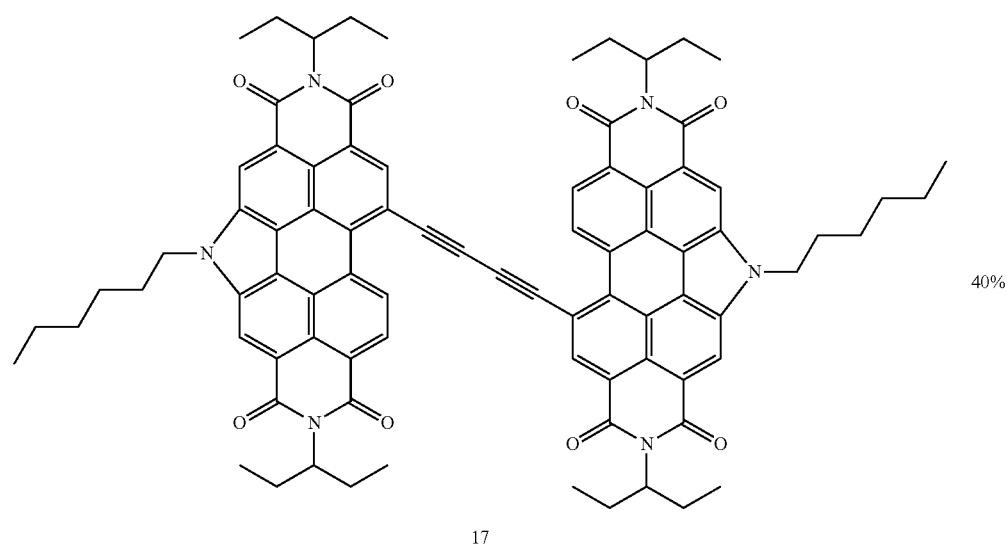
17
40%
Compound 17 can be prepared from compound 16 using an improved method:
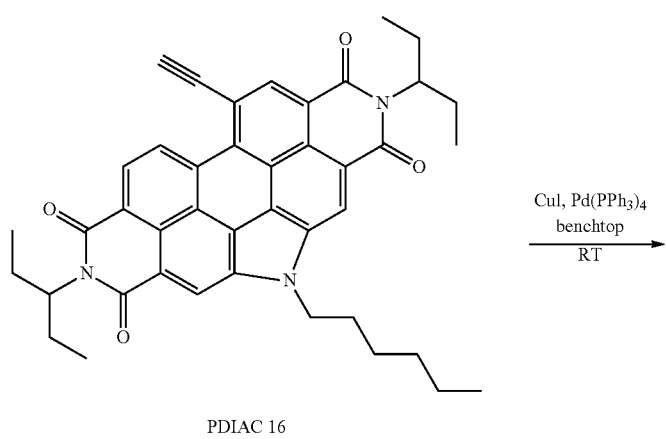
PDIAC 16
CuI, Pd(PPh₃)₄
benchtop
RT

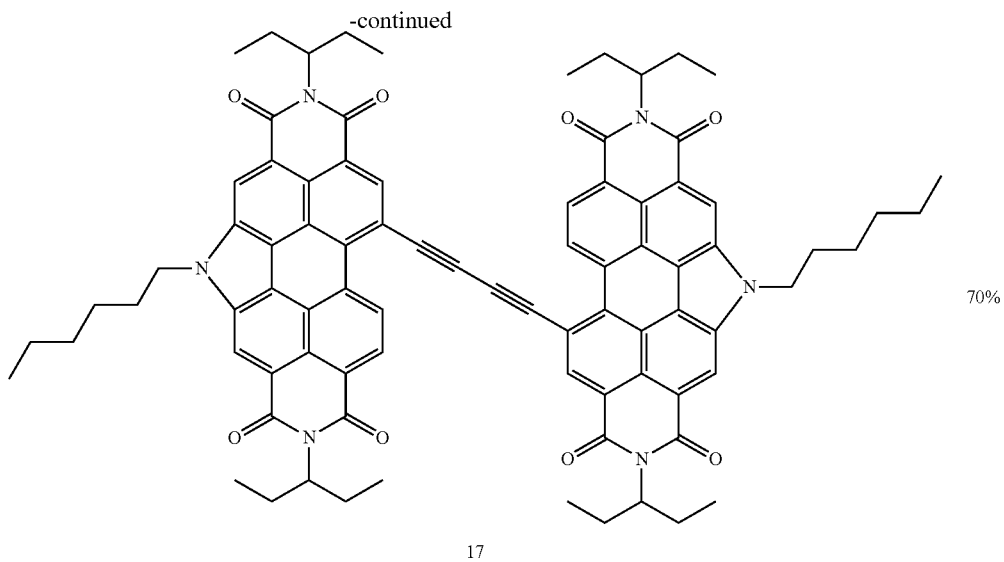

17 70%

To a 100 ml round bottom flask containing (200 mg, 0.3 mmol), copper iodide (6 mg, 0.03 mmol), potassium carbonate (124 mg, 0.9 mmol) and Pd(PPh$_3$)$_4$ (35 mg, 0.03 mmol) was added 10 mL chloroform and 10 ml methanol. The solution was stirred, open to air for 1 hour. The purple solution was filtered over silica with THF to remove metal catalysts. The solvent was removed from the purple filtrate under reduced pressure to give a PDIACACPDI (17) (205 mg) as a purple solid. PDIACACPDI (17) was purified via silica column chromatography using hexanes to DCM to 5% THF gradient. (140 mg, 0.11 mmol, 70%)

Figure 10A:
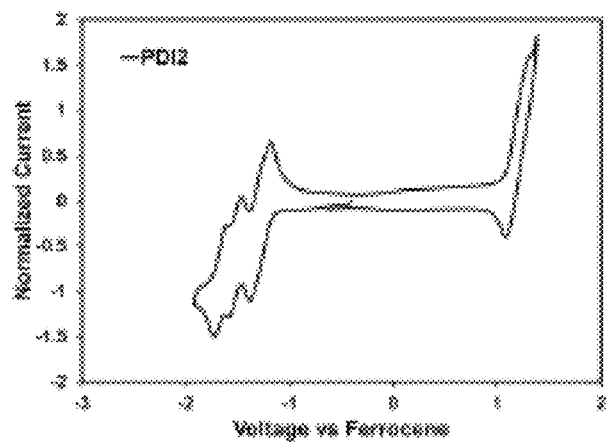
FIGS. 10A-C show cyclic voltammograms for compounds 7, 15 and 17, respectively, and indicate HOMO and LUMO energy levels for these compounds.
Figure 10B:
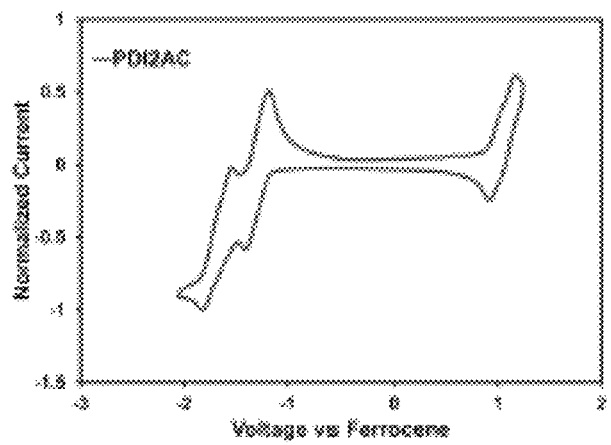
Figure 10C:
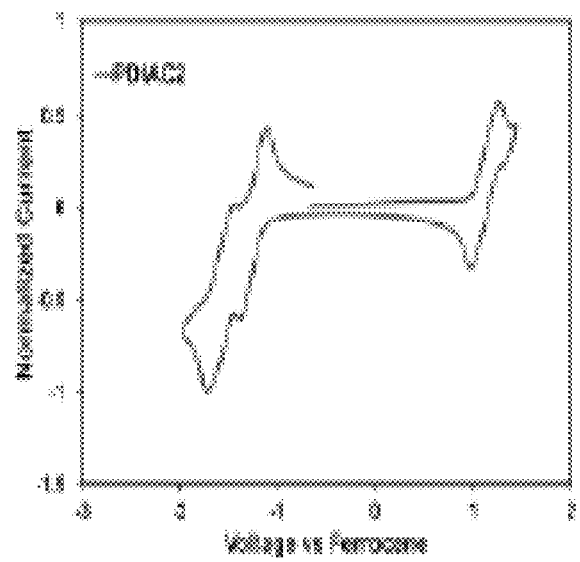
Figure 11A:
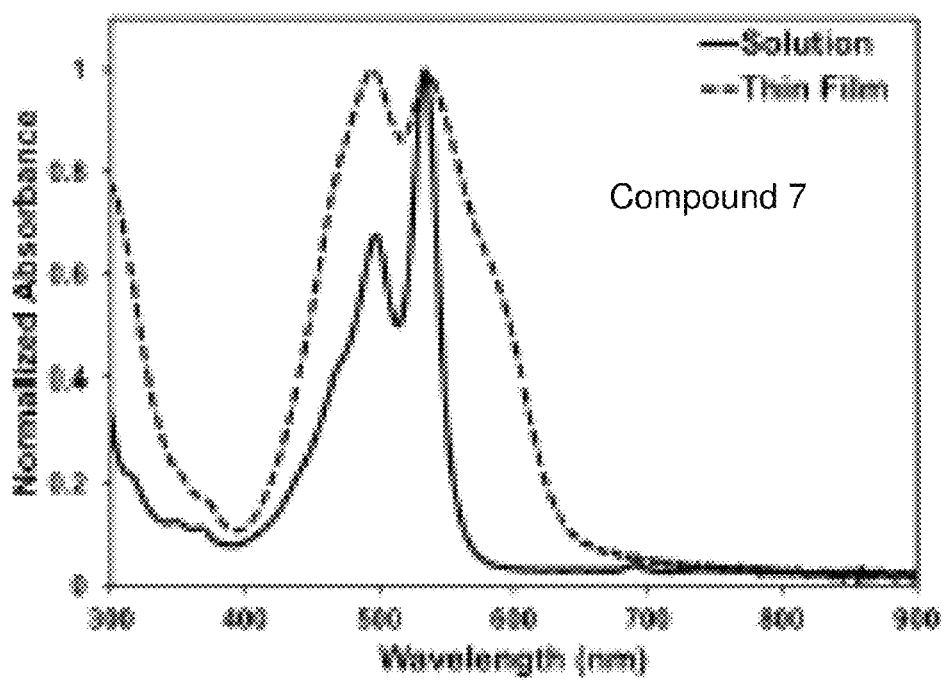
FIGS. 11A-C show absorption spectra for compounds 7, 15 and 17, respectively, in solution (solid line) and in a thin film (dashed line). Films were cast from 10 mg/mL solutions of the compound in chloroform onto PEIE-coated substrates at 3000 RPM.
Figure 11B:
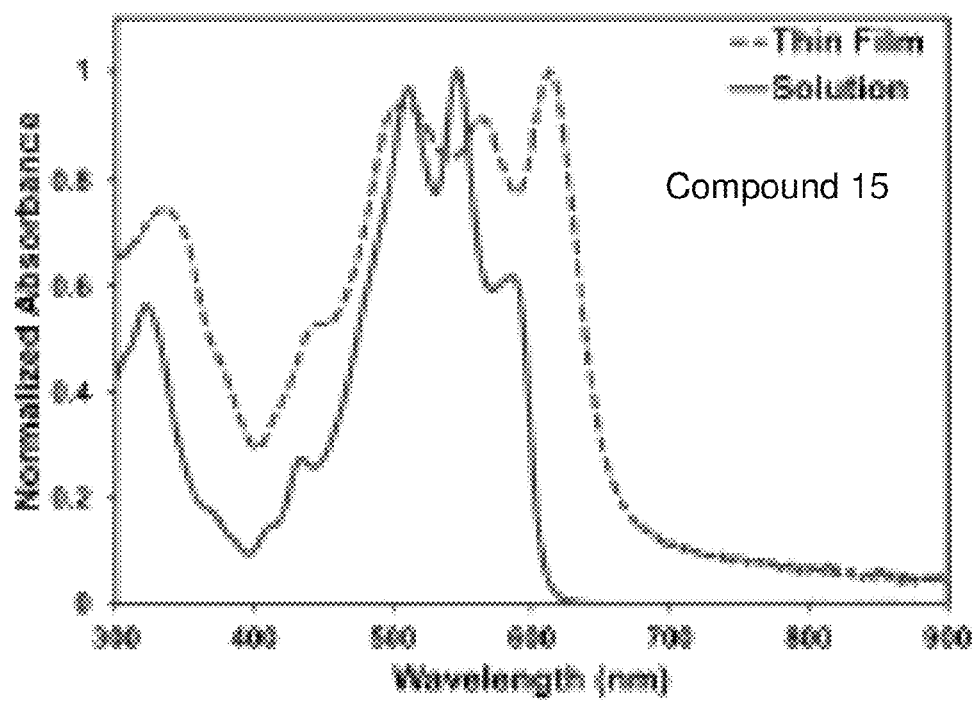
Figure 11C:
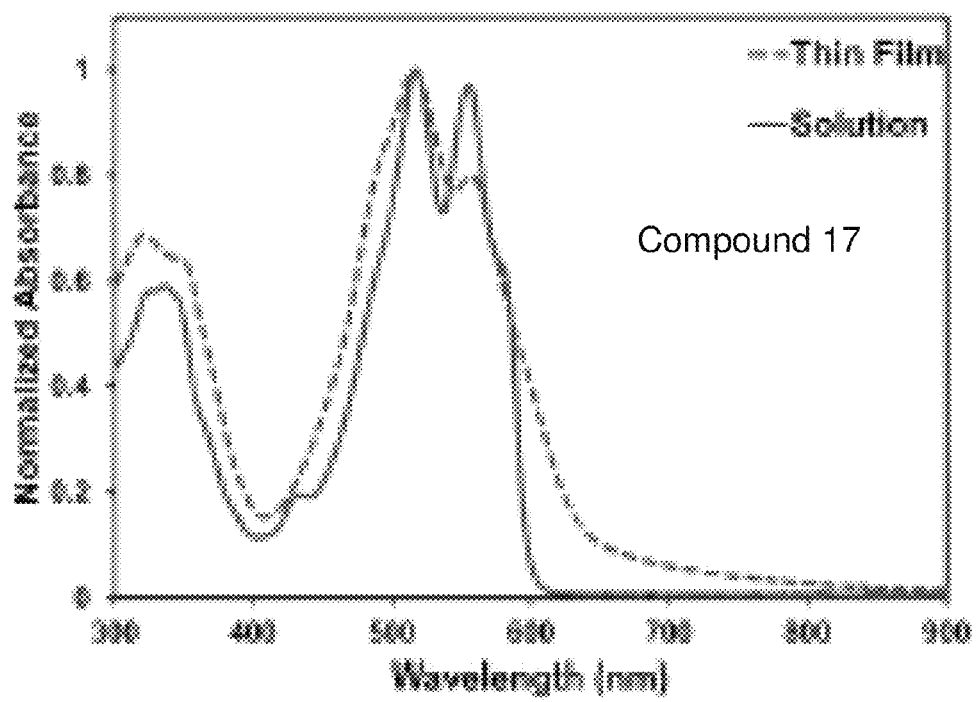

FIGS. 10A-C and 11A-C illustrate properties of compounds 15 and 17 compared to compound 7. FIGS. 10A-10C show cyclic voltammograms for compounds 7, 15 and 17, respectively, and indicate HOMO and LUMO energy levels. FIGS. 11A-C show absorption spectra for compounds 7, 15 and 17, respectively, in solution (solid line) and in a thin film (dashed line).

REFERENCES (1) Zhan, X.; Facchetti, A.; Barlow, S.; Marks, T. J.; Ratner, M. A.; Wasielewski, M. R.; Marder, S. R. Perylene and Related Diimides for Organic Electronics. Adv. Mater. 2011, 23, 268-284.

(2) Zhong, Y.; Trinh, M. T.; Chen, R.; Purdum, G. E.; Khlyabich, P. P.; Sezen, M.; Oh, S.; Zhu, H.; Fowler, B.; Zhang, B.; Wang, W.; Nam, C.-Y.; Sfeir, M. Y.; Black, C. T.; Steigerwald, M. L.; Loo, Y.-L.; Ng, F.; Zhu, X.-Y.; Nuckolls, C. Molecular Helices as Electron Acceptors in High-Performance Bulk Heterojunction Solar Cells. Nat. Commun. 2015, 6, 8242.

(3) Meng, D.; Sun, D.; Zhong, C.; Liu, T.; Fan, B.; Huo, L.; Li, Y.; Jiang, W.; Choi, H.; Kim, T.; Kim, J. Y.; Sun, Y.; Wang, Z.; Heeger, A. J. High-Performance Solution-Processed Non-Fullerene Organic Solar Cells Based on Selenophene-Containing Perylene Bisimide Acceptor. J. Am. Chem. Soc. 2016, 138, 375-380.

(4) Zhong, Y.; Trinh, M. T.; Chen, R.; Wang, W.; Khlyabich, P. P.; Kumar, B.; Xu, Q.; Nam, C.-Y.; Sfeir, M. Y.; Black, C.; Steigerwald, M. L.; Loo, Y.-L.; Xiao, S.; Ng, F.; Zhu, X.-Y.; Nuckolls, C. Efficient Organic Solar Cells with Helical Perylene Diimide Electron Acceptors. J. Am. Chem. Soc. 2014, 136, 15215-15221.

(5) Liu, K.; Xu, Z.; Yin, M.; Yang, W.; He, B.; Wei, W.; Shen, J. A Multifunctional Perylenediimide Derivative (DTPDI) Can Be Used as a Recyclable Specific Hg2+ Ion Sensor and an Efficient DNA Delivery Carrier. J. Mater. Chem. B 2014, 2, 2093-2096.

(6) Dwivedi, A. K.; Pandeeswar, M.; Govindaraju, T. Assembly Modulation of PDI Derivative as a Supramolecular Fluorescence Switching Probe for Detection of Cationic Surfactant and Metal Ions in Aqueous Media. ACS Appl. Mater. Interfaces 2014, 6, 21369-21379.

(7) Doval, D. A.; Fin, A.; Takahashi-Umebayashi, M.; Riezman, H.; Roux, A.; Sakai, N.; Matile, S. Amphiphilic Dynamic NDI and PDI Probes: Imaging Microdomains in Giant Unilamellar Vesicles. Org. Biomol. Chem. 2012, 10, 6087-6093.

(8) Acikbas, Y.; Erdogan, M.; Capan, R.; Yukruk, F. Optical Characterization of an N,N'-Dicyclohexyl-3, 4:9, 10-Perylene bis(Dicarboximide) Langmuir-Blodgett Film for the Determination of Volatile Organic Compounds. Anal. Lett. February 2016, 46(16):2573-2586, DOI: 10.1080/00032719.2015.1122028.

(9) Hariharan, P. S.; Pitchaimani, J.; Madhu, V.; Anthony, S. P. Perylene Diimide Based Fluorescent Dyes for Selective Sensing of Nitroaromatic Compounds: Selective Sensing in Aqueous Medium Across Wide pH Range. J. Fluoresc. 2016, 26, 395-401.

(10) Huang, Y.; Zhang, W.; Wang, J.; Wei, Z. Probing the Sensory Property of Perylenediimide Derivatives in Hydrazine Gas: Core-Substituted Aromatic Group Effect. ACS Appl. Mater. Interfaces 2014, 6, 9307-9313.

(11) Feng, X.; An, Y.; Yao, Z.; Li, C.; Shi, G. A Turn-on Fluorescent Sensor for Pyrophosphate Based on the Disassembly of Cu2+-Mediated Perylene Diimide Aggregates. ACS Appl. Mater. Interfaces 2012, 4, 614-618.

(12) Hüttner, S.; Sommer, M.; Thelakkat, M. N-Type Organic Field Effect Transistors from Perylene Bisimide Block Copolymers and Homopolymers. Appl. Phys. Lett. 2008, 92, 093302.

(13) Lüttich, F.; Lehmann, D.; Friedrich, M.; Chen, Z.; Facchetti, A.; Borczyskowski, C.; von Zahn, D. R. T.; Graaf, H. Interface Properties of OFETs Based on an

(14) Centore, R.; Ricciotti, L.; Carella, A.; Roviello, A.; Causà, M.; Barra, M.; Ciccullo, F.; Cassinese, A. Perylene Diimides Functionalized with N-Thiadiazole Substituents: Synthesis and Electronic Properties in OFET Devices. Org. Electron. 2012, 13, 2083-2093.

(15) Tilley, A. J.; Guo, C.; Miltenburg, M. B.; Schon, T. B.; Yan, H.; Li, Y.; Seferos, D. S. Thionation Enhances the Electron Mobility of Perylene Diimide for High Performance N-Channel Organic Field Effect Transistors. Adv. Funct. Mater. 2015, 25, 3321-3329.

(16) Kozma, E.; Catellani, M. Perylene Diimides Based Materials for Organic Solar Cells. Dyes Pigm. 2013, 98, 160-179.

(17) Fernandez-Lazaro, F.; Zink-Lorre, N.; Sastre-Santos, A. Perylenediimides as Non-Fullerene Acceptors in Bulk-Heterojunction Solar Cells (BHJSCs). J. Mater. Chem. A 2016, 4, 9336-9346.

(18) Hartnett, P. E.; Timalsina, A.; Matte, H. S. S. R.; Zhou, N.; Guo, X.; Zhao, W.; Facchetti, A.; Chang, R. P. H.; Hersam, M. C.; Wasielewski, M. R.; Marks, T. J. Slip-Stacked Perylenediimides as an Alternative Strategy for High Efficiency Nonfullerene Acceptors in Organic Photovoltaics. J. Am. Chem. Soc. 2014, 136, 16345-16356.

(19) Jiang, W.; Ye, L.; Li, X.; Xiao, C.; Tan, F.; Zhao, W.; Hou, J.; Wang, Z. Bay-Linked Perylene Bisimides as Promising Non-Fullerene Acceptors for Organic Solar Cells. Chem. Commun. 2014, 50, 1024-1026.

(20) Su, Y.-W.; Lan, S.-C.; Wei, K.-H. Organic Photovoltaics. Mater. Today 2012, 15, 554-562.

(21) Li, G.; Zhu, R.; Yang, Y. Polymer Solar Cells. Nat. Photonics 2012, 6, 153-161.

(22) Roncali, J.; Leriche, P.; Blanchard, P. Molecular Materials for Organic Photovoltaics: Small Is Beautiful. Adv. Mater. 2014, 26, 3821-3838.

(23) Lin, Y.; Zhan, X. Non-Fullerene Acceptors for Organic Photovoltaics: An Emerging Horizon. Mater. Horiz. 2014, 1, 470-488.

(24) Eftaiha, A. F.; Sun, J.-P.; Hill, I. G.; Welch, G. C. Recent Advances of Non-Fullerene, Small Molecular Acceptors for Solution Processed Bulk Heterojunction Solar Cells. J. Mater. Chem. A 2014, 2, 1201-1213.

(25) Chochos, C. L.; Tagmatarchis, N.; Gregoriou, V. G. Rational Design on N-Type Organic Materials for High Performance Organic Photovoltaics. RSC Adv. 2013, 3, 7160-7181.

(26) Anthony, J. E. Small-Molecule, Nonfullerene Acceptors for Polymer Bulk Heterojunction Organic Photovoltaics. Chem. Mater. 2011, 23, 583-590.

(27) Zhan, C.; Zhang, X.; Yao, J. New Advances in Non-Fullerene Acceptor Based Organic Solar Cells. RSC Adv. 2015, 5, 93002-93026.

(28) McAfee, S. M.; Topple, J. M.; Hill, I. G.; Welch, G. C. Key Components to the Recent Performance Increases of Solution Processed Non-Fullerene Small Molecule Acceptors. J. Mater. Chem. A 2015, 3, 16393-16408.

(29) Zhan, C.; Yao, J. More than Conformational "Twisting" or "Coplanarity": Molecular Strategies for Designing High-Efficiency Nonfullerene Organic Solar Cells. Chem. Mater. 2016, 28, 1948-1964.

(30) Lin, Y.; Wang, J.; Dai, S.; Li, Y.; Zhu, D.; Zhan, X. A Twisted Dimeric Perylene Diimide Electron Acceptor for Efficient Organic Solar Cells. Adv. Energy Mater. 2014, 4, 1400420.

(31) Lin, Y.; Wang, Y.; Wang, J.; Hou, J.; Li, Y.; Zhu, D.; Zhan, X. A Star-Shaped Perylene Diimide Electron Acceptor for High-Performance Organic Solar Cells. Adv. Mater. 2014, 26, 5137-5142.

(32) Chen, W.; Yang, X.; Long, G.; Wan, X.; Chen, Y.; Zhang, Q. A Perylene Diimide (PDI)-Based Small Molecule with Tetrahedral Configuration as a Non-Fullerene Acceptor for Organic Solar Cells. J. Mater. Chem. C 2015, 3, 4698-4705.

(33) Zhan, X.; Tan, Z.; Domercq, B.; An, Z.; Zhang, X.; Barlow, S.; Li, Y.; Zhu, D.; Kippelen, B.; Marder, S. R. A High-Mobility Electron-Transport Polymer with Broad Absorption and Its Use in Field-Effect Transistors and All-Polymer Solar Cells. J. Am. Chem. Soc. 2007, 129, 7246-7247.

(34) Liu, X.; Luo, G.; Cai, X.; Wu, H.; Su, S.-J.; Cao, Y. Pyrene Terminal Functionalized Perylene Diimide as Non-Fullerene Acceptors for Bulk Heterojunction Solar Cells. RSC Adv. 2015, 5, 83155-83163.

(35) Yan, Q.; Zhou, Y.; Zheng, Y.-Q.; Pei, J.; Zhao, D. Towards Rational Design of Organic Electron Acceptors for Photovoltaics: A Study Based on Perylenediimide Derivatives. Chem. Sci. 2013, 4, 4389-4394.

(36) Sun, D.; Meng, D.; Cai, Y.; Fan, B.; Li, Y.; Jiang, W.; Huo, L.; Sun, Y.; Wang, Z. Non-Fullerene Acceptor-Based Bulk Heterojunction Organic Solar Cells with Efficiency over 7%. J. Am. Chem. Soc. 2015, 137, 11156-11162.

(37) Zang, Y.; Li, C.-Z.; Chueh, C.-C.; Williams, S. T.; Jiang, W.; Wang, Z.-H.; Yu, J.-S.; Jen, A. K.-Y. Integrated Molecular, Interfacial, and Device Engineering towards High-Performance Non-Fullerene Based Organic Solar Cells. Adv. Mater. 2014, 26, 5708-5714.

(38) Demmig, S.; Langhals, H. Leichtlösliche, Lichtechte Perylen-Fluoreszenzfarbstoffe. Chem. Ber. 1988, 121, 225-230.

(39) Langhals, H.; Kirner, S. Novel Fluorescent Dyes by the Extension of the Core of Perylenetetracarboxylic Bisimides. Eur. J. Org. Chem. 2000, 2000, 365-380.

(40) Freeman, A. W.; Urvoy, M.; Criswell, M. E. Triphenylphosphine-Mediated Reductive Cyclization of 2-Nitrobiphenyls: A Practical and Convenient Synthesis of Carbazoles. J. Org. Chem. 2005, 70, 5014-5019.

(41) Marrocchi, A.; Facchetti, A.; Lanari, D.; Petrucci, C.; Vaccaro, L. Current Methodologies for a Sustainable Approach to [Capital Pi]-Conjugated Organic Semiconductors. Energy Environ. Sci. 2016, 9, 763-786.

(42) McAfee, S. M.; Cann, J. R.; Josse, P.; Blanchard, P.; Cabanetos, C.; Welch, G. C. The Optimization of Direct Heteroarylation and Sonogashira Cross-Coupling Reactions as Efficient and Sustainable Synthetic Methods to Access π-Conjugated Materials with Near-Infrared Absorption. ACS Sustainable Chem. Eng. 2016, 4, 3504-3517.

(43) McAfee, S. M.; McCahill, J. S. J.; Macaulay, C. M.; Hendsbee, A. D.; Welch, G. C. Utility of a Heterogeneous Palladium Catalyst for theSynthesis of a Molecular Semiconductor via Stille, Suzuki, and Direct Heteroarylation Cross-Coupling Reactions. RSC Adv. 2015, 5, 26097-26106.

(44) Burke, D. J.; Lipomi, D. J. Green Chemistry for Organic Solar Cells. Energy Environ. Sci. 2013, 6, 2053-2066.

(45) Rajasingh, P.; Cohen, R.; Shirman, E.; Shimon, L. J. W.; Rybtchinski, B. Selective Bromination of Perylene Diimides under Mild Conditions. J. Org. Chem. 2007, 72, 5973-5979.

(46) Hendsbee, A. D.; McAfee, S. M.; Sun, J.-P.; McCormick, T. M.; Hill, I. G.; Welch, G. C. Phthalimide-Based [Small Pi]-Conjugated Small Molecules with Tailored Electronic Energy Levels for Use as Acceptors in Organic Solar Cells. J. Mater. Chem. C 2015, 3, 8904-8915.
(47) Ding, L.; Li, H.-B.; Lei, T.; Ying, H.-Z.; Wang, R.-B.; Zhou, Y.; Su, Z.-M.; Pei, J. Alkylene-Chain Effect on Microwire Growth and Crystal Packing of 7-Moieties. Chem. Mater. 2012, 24, 1944-1949.
(48) Anthony, J. E.; Eaton, D. L.; Parkin, S. R. A Road Map to Stable, Soluble, Easily Crystallized Pentacene Derivatives. Org. Lett. 2002, 4, 15-18.
(49) Fitzner, R.; Elschner, C.; Weil, M.; Uhrich, C.; Körner, C.; Riede, M.; Leo, K.; Pfeiffer, M.; Reinold, E.; Mena-Osteritz, E.; Bauerle, P. Interrelation between Crystal Packing and Small-Molecule Organic Solar Cell Performance. Adv. Mater. 2012, 24, 675-680.
(50) Kim, C.; Liu, J.; Lin, J.; Tamayo, A. B.; Walker, B.; Wu, G.; Nguyen, T.-Q. Influence of Structural Variation on the Solid-State Properties of Diketopyrrolopyrrole-Based Oligophenylenethiophenes: Single-Crystal Structures, Thermal Properties, Optical Bandgaps, Energy Levels, Film Morphology, and Hole Mobility. Chem. Mater. 2012, 24, 1699-1709.
(51) Namepetra, A.; Kitching, E.; Eftaiha, A. F.; Hill, I. G.; Welch, G. C. Understanding the Morphology of Solution Processed Fullerene-Free Small Molecule Bulk Heterojunction Blends. Phys. Chem. Chem. Phys. 2016, 18, 12476-12485.
(52) Sun, J.-P.; Hendsbee, A. D.; Dobson, A. J.; Welch, G. C.; Hill, I. G. Perylene Diimide Based All Small-Molecule Organic Solar Cells: Impact of Branched-Alkyl Side Chains on Solubility, Photophysics, Self-Assembly, and Photovoltaic Parameters. Org. Electron. 2016, 35, 151-157.
(53) Qian, H.; Yue, W.; Zhen, Y.; Di Motta, S.; Di Donato, E.; Negri, F.; Qu, J.; Xu, W.; Zhu, D.; Wang, Z. Heterocyclic Annelated Di(perylene Bisimide): Constructing Bowl-Shaped Perylene Bisimides by the Combination of Steric Congestion and Ring Strain. J. Org. Chem. 2009, 74, 6275-6282.
(54) Forrest, S. R. The Path to Ubiquitous and Low-Cost Organic Electronic Appliances on Plastic. Nature 2004, 428, 911-918.
(55) Mei, J.; Bao, Z. Side Chain Engineering in Solution-Processable Conjugated Polymers. Chem. Mater. 2014, 26, 604-615.
(56) Li, M.; Liu, J.; Cao, X.; Zhou, K.; Zhao, Q.; Yu, X.; Xing, R.; Han, Y. Achieving Balanced Intermixed and Pure Crystalline Phases in PDI-Based Non-Fullerene Organic Solar Cells via Selective Solvent Additives. Phys. Chem. Chem. Phys. 2014, 16, 26917-26928.
(57) Chen, Z.; Stepanenko, V.; Dehm, V.; Prins, P.; Siebbeles, L. D. A.; Seibt, J.; Marquetand, P.; Engel, V.; WUrthner, F. Photoluminescence and Conductivity of Self-Assembled Π-π Stacks of Perylene Bisimide Dyes. Chem.-Eur. J. 2007, 13, 436-449.
(58) Bredas, J.-L. Mind the Gap! Mater. Horiz. 2014, 1, 17-19.
(59) Cardona, C. M.; Li, W.; Kaifer, A. E.; Stockdale, D.; Bazan, G. C. Electrochemical Considerations for Determining Absolute Frontier Orbital Energy Levels of Conjugated Polymers for Solar Cell Applications. Adv. Mater. 2011, 23, 2367-2371.
(60) Li, J.; Dierschke, F.; Wu, J.; Grimsdale, A. C.; Mullen, K. Poly(2,7-Carbazole) and Perylene Tetracarboxydiimide: A Promising Donor/acceptor Pair for Polymer Solar Cells. J. Mater. Chem. 2006, 16, 96-100.
(61) Lu, L.; Yu, L. Understanding Low Bandgap Polymer PTB7 and Optimizing Polymer Solar Cells Based on It. Adv. Mater. 2014, 26, 4413-4430.
(62) Chang, L.; Jacobs, I. E.; Augustine, M. P.; Moulé, A. J. Correlating Dilute Solvent Interactions to Morphology and OPV Device Performance. Org. Electron. 2013, 14, 2431-2443.
(63) Liao, H.-C.; Ho, C.-C.; Chang, C.-Y.; Jao, M.-H.; Darling, S. B.; Su, W.-F. Additives for Morphology Control in High-Efficiency Organic Solar Cells. Mater. Today 2013, 16, 326-336.
(64) Chen, K.-Y.; Chow, T. J. Tetrahedron Lett. 2010, 51 (45), 5959.
(65) Qiu, S.; Liu, L.; Wang, B.; Shen, F.; Zhang, W.; Li, M.; Ma, Y. Macromolecules 2005, 38 (16), 67.
(66) Hendsbee, A. D.; Sun, J-P.; Law W. K.; Yan, H.; Hill, I. G.; Denis M. Spasyuk, D. M. and Welch, G. C. Synthesis, Self-Assembly, and Solar Cell Performance of N-AnnulatedPerylene Diimide Non-Fullerene Acceptors. Chem. Mater, September 2016, 28, 7098-7109.
(67) McAfee, S. M.; Dayneko, S. V.; Josse, P.; Blanchard, P.; Cabanetos, C.; and Welch, G. C. Simply Complex: The Efficient Synthesis of an Intricate Molecular Acceptor for High-Performance Air-Processed and Air-Tested Fullerene-Free Organic Solar Cells, Chem. Mater., January 2017, 29, 1309-1314.
(68) Dayneko, S. V.; Hendsbee, A. D.; and Welch, G. C. Fullerene-free polymer solar cells processed from non-halogenated solvents in air with PCE of 4.8% Chem. Comm. 53, 1164-1167.
(69) Liao, S-H.; Jhuo, H.-J.; Cheng, Y.-S. and Chen, S.-A., Adv. Mater., 2013, 25, 4766-4771.
(70) Zhao, D.; Wu, Q.; Cai, Z.; Zheng, T.; Chen, W.; Lu J.; and Yu, L., Chem. Mater., 2016, 28, 1139-1146.
(71) Liu, Z.; Wu, Y.; Zhang, Q.; and Gao, X.; J. Mater. Chem. A, 2016, 4, 17604-17622.
(72) Zhan, C.; Yao, J. More than Conformational "Twisting" or "Coplanarity": Molecular Strategies for Designing High-Efficiency Nonfullerene Organic Solar Cells. Chem. Mater. 2016, 28, 1948-1964.
(73) Zhao, J.; Li, Y.; Lin, H.; Liu, Y.; Jiang, K.; Mu, C.; Ma, T.; Lai, J. Y. L.; Hu, H.; Yu, D.; Yan, H. High-Efficiency Non-Fullerene Organic Solar Cells Enabled by a Difluoro-benzothiadiazole-Based Donor Polymer Combined with a Properly Matched Small Molecule Acceptor. Energy Environ. Sci. 2015, 8, 520-525.
(74) Zhang, X.; Zhan, C.; Yao, J. Non-Fullerene Organic Solar Cells with 6.1% Efficiency through Fine-Tuning Parameters of the Film-Forming Process. Chem. Mater. 2015, 27, 166-173.
(75) Zhang, X.; Yao, J.; Zhan, C. A Selenophenyl Bridged Perylene Diimide Dimer as an Efficient Solution-Processable Small Molecule Acceptor. Chem. Commun. 2015, 51, 1058-1061.
(76) Zhang, X.; Li, W.; Yao, J.; Zhan, C. High-Efficiency Nonfullerene Polymer Solar Cell Enabling by Integration of Film-Morphology Optimization, Donor Selection, and Interfacial Engineering. ACS Appl. Mater. Interfaces 2016, 8, 15415-15421.
(77) Hendsbee, A. D.; Sun, J.-P.; Rutledge, L. R.; Hill, I. G.; Welch, G. C. Electron Deficient Diketopyrrolopyrrole Dyes for Organic Electronics: Synthesis by Direct Arylation, Optoelectronic Characterization, and Charge Carrier Mobility. J. Mater. Chem. A 2014, 2 (12), 4198-4207.

The invention claimed is:

1. A compound of formula:

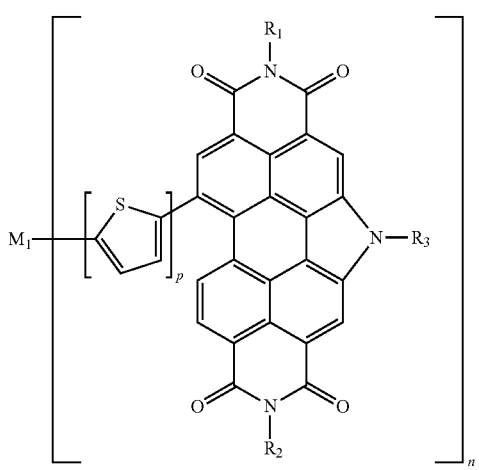

where p is 0 or 1;

n is 2, 3 or 4;

$R_1$ and $R_2$ are independently selected from a straight-chain alkyl having 1-30 carbon atoms and a branched alkyl having 3-30 carbon atoms;

$R_3$ is independently selected from a straight-chain alkyl having 1-30 carbon atoms and a branched alkyl group having 3-30 carbon atoms; and $M_1$ is selected from an arylene (—Ar—), a heteroarylene (—HAr—), an alkynylene (-≡-), a dialkynylene (-≡-≡-), and an organic dye moiety.

2. The compound of claim 1, wherein p is 0 and n is 2.

3. The compound of claim 1, wherein p is 1 and n is 2.

4. The compound of claim 1, wherein $M_1$ is an alkynylene or a dialkynylene.

5. The compound of claim 1, wherein $M_1$ is an arylene.

6. The compound of claim 1, wherein $M_1$ is heteroarylene.

7. The compound of claim 1, wherein $M_1$ is a phenylene, a naphthylene or an anthracenylene.

8. The compound of claim 1, wherein $M_1$ is selected from any one of:

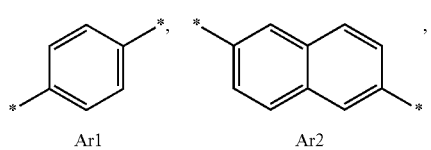

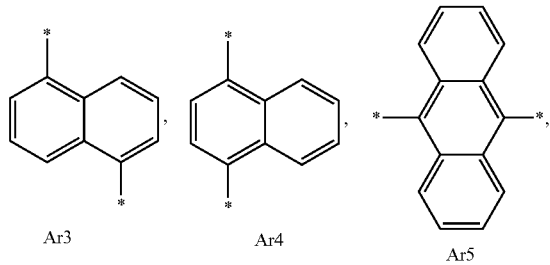

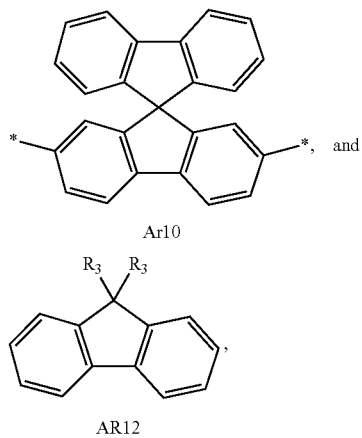

wherein each $R_3$ is independently selected from alkyl groups having 1-30 carbon atoms.

9. The compound of claim 1, wherein $M_1$ is selected from any one of:

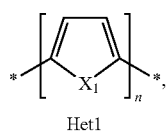

where $X_1$ is O, S or Se and n=1-6;

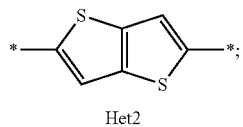

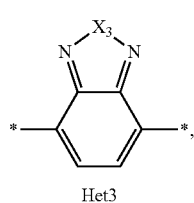

where $X_3$ is O, S or Se;

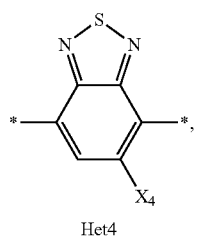

where $X_4$ is F or CN;
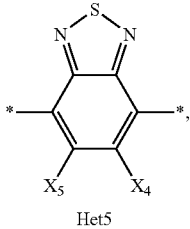
Het5
where $X_5$ is F or CN;
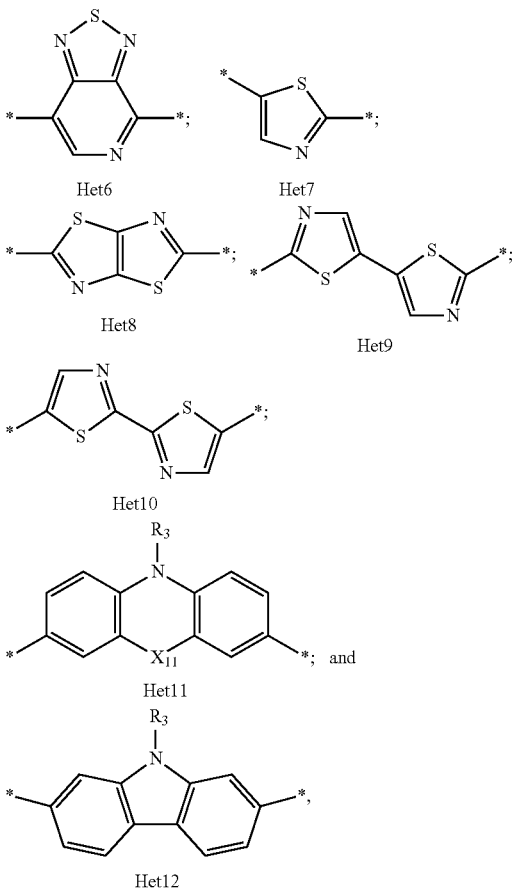
Het6   Het7
Het8   Het9
Het10
Het11
Het12
wherein each $R_3$ is independently selected from alkyl groups having 1-30 carbon atoms and X11 is S or O.
10. The compound of claim 1, wherein $M_1$ is selected from any one of:
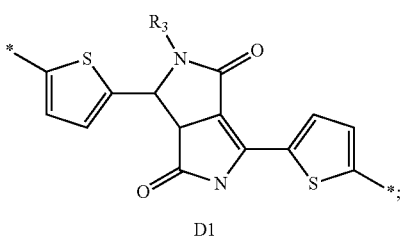
D1
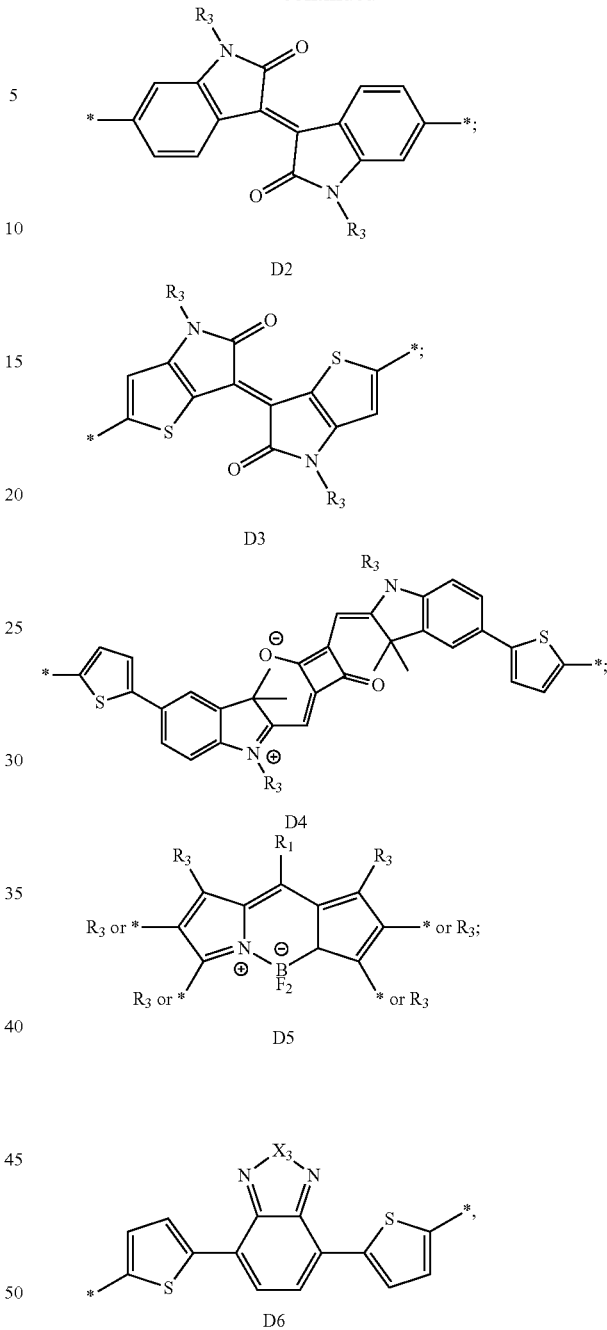
D2
D3
D4
D5
where $X_3$ is O, S or Se;
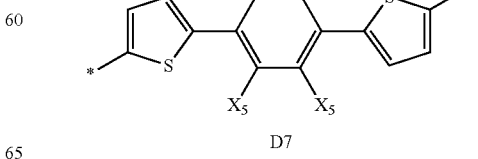
D7 where $X_5$ is CN or F;

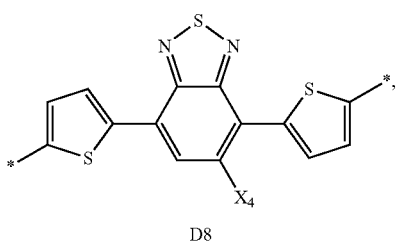
D8 where $X_4$ is CN or F;

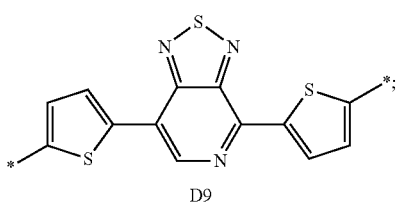
D9

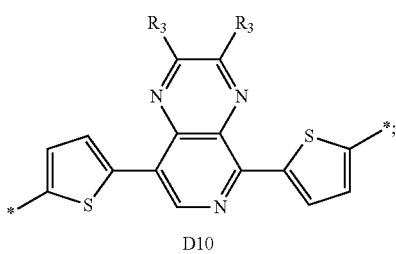
D10 and

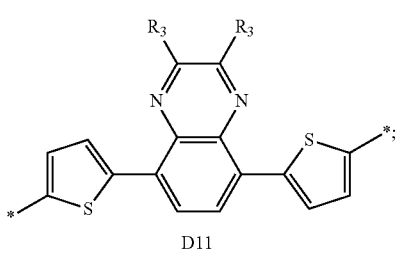
D11

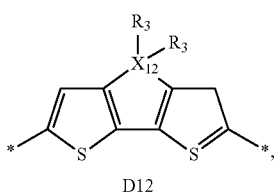
D12 where $X_{12}$ is C, Si or Ge, and
wherein each $R_1$ and each $R_3$ is independently selected from alkyl groups having 1-30 carbon atoms.

11. The compound of claim 1, wherein $M_1$ is

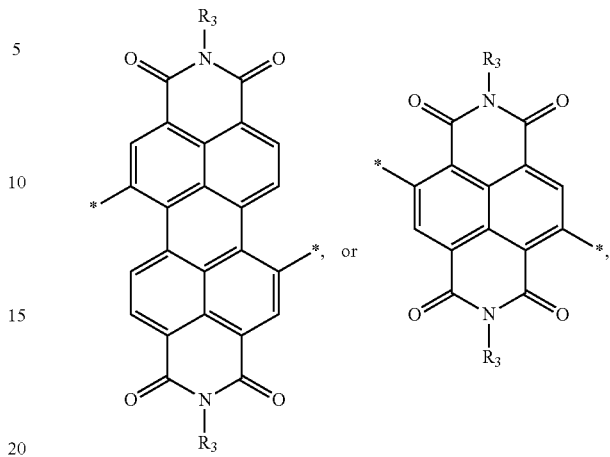

wherein each $R_3$ is independently selected from alkyl groups having 1-30 carbon atoms.

12. The compound of claim 1, wherein $M_1$ is

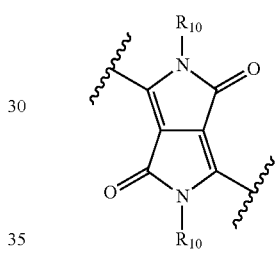

where each $R_{10}$ independently is a straight-chain alkyl having 1-30 carbon atoms or a branched alkyl group having 3 to 20 carbon atoms.

13. The compound of claim 12, wherein each $R_{10}$ is a straight-chain alkyl group having 6-12 carbon atoms.

14. The compound of claim 1 having formula:

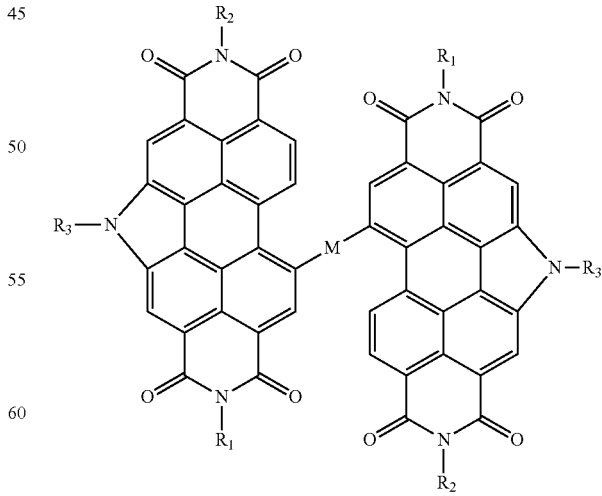

where $R_1$ and $R_2$ are independently selected from a straight-chain alkyl having 1-30 carbon atoms and a branched alkyl having 3-30 carbon atoms;

R₃ is independently selected from a straight-chain alkyl having 1-30 carbon atoms and a branched alkyl group having 3-30 carbon atoms; and M is selected from an arylene (—Ar—), a heteroarylene (—HAr—), an alkynylene (-≡-), and a dialkynylene (-≡-≡-).

15. The compound of claim 14, wherein M is an alkynylene (-≡-), or a dialkynylene (-≡-≡-).

16. An electronic device employing an electron acceptor wherein the electron acceptor is one or more compounds of claim 1.

17. The electronic device of claim 16 which is an organic solar cell, an organic thin film transistor or a redox flow battery.

18. A compound of formula I:

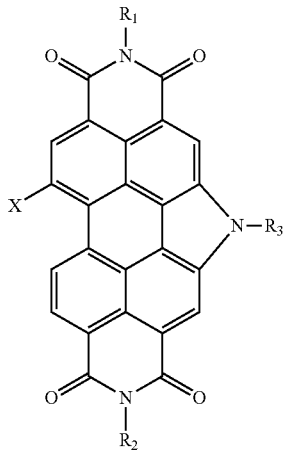

where:

X is a halogen, triflyl, tosyl or mesyl group;

R₁ and R₂ are independently selected from a straight-chain alkyl having 1-30 carbon atoms or a branched alkyl having 3-30 carbon atoms and R₃ is independently selected from a straight-chain alkyl having 1-30 carbon atoms or a branched alkyl group having 3-30 carbon atoms.

19. The compound of claim 18, wherein X is Br, R₁ and R₂ are branched alkyl groups having 3-12 carbon atoms and R₃ is a straight-chain alkyl having 3-8 carbon atoms.

20. A method for making the compound of claim 18, where X is bromine, which comprises the step of bromination of a compound of formula V:

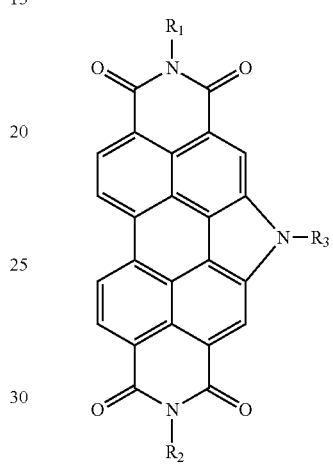

in an organic solvent in which the compound of formula V is soluble at room temperature in a molar excess of Br₂ with respect to the compound of formula V.

* * * * *